(12) United States Patent
Wang et al.

(10) Patent No.: US 9,746,468 B2
(45) Date of Patent: Aug. 29, 2017

(54) BIOAFFINITY SENSORS BASED ON SURFACE MONOLAYERS

(75) Inventors: Joseph Wang, San Diego, CA (US); Susana Campuzano-Ruiz, Madrid (ES)

(73) Assignee: The Regents of the University of California, Oakland, CA (US)

( * ) Notice: Subject to any disclaimer, the term of this patent is extended or adjusted under 35 U.S.C. 154(b) by 183 days.

(21) Appl. No.: 13/982,258

(22) PCT Filed: Jan. 27, 2012

(86) PCT No.: PCT/US2012/023039
§ 371 (c)(1),
(2), (4) Date: Jan. 2, 2014

(87) PCT Pub. No.: WO2012/148516
PCT Pub. Date: Nov. 1, 2012

(65) Prior Publication Data
US 2014/0106441 A1    Apr. 17, 2014

Related U.S. Application Data

(60) Provisional application No. 61/437,557, filed on Jan. 28, 2011.

(51) Int. Cl.
*G01N 33/543* (2006.01)
*C12Q 1/68* (2006.01)
(Continued)

(52) U.S. Cl.
CPC ....... *G01N 33/54386* (2013.01); *C12Q 1/689* (2013.01); *G01N 27/30* (2013.01); *G01N 27/327* (2013.01); *G01N 27/3277* (2013.01)

(58) Field of Classification Search
CPC ......... G01N 33/54386; G01N 27/3277; G01N 27/327; G01N 27/30
See application file for complete search history.

(56) References Cited

U.S. PATENT DOCUMENTS

| 3,363,983 A | 1/1968 | Roberts |
| 7,087,148 B1 * | 8/2006 | Blackburn ............ B82Y 30/00 204/403.06 |

(Continued)

FOREIGN PATENT DOCUMENTS

| WO | 03099112 | 12/2003 |
| WO | 2011031463 | 3/2011 |

OTHER PUBLICATIONS

Arya, S.K.et al., "Recent advances in self-assembled monolayers based biomolecular electronic devices", Biosens. Bioelectron, 24, 2009, pp. 2810-2817.

(Continued)

*Primary Examiner* — Melanie Y Brown
(74) *Attorney, Agent, or Firm* — Perkins Coie LLP

(57) ABSTRACT

Methods, systems, devices and materials are disclosed for implementing a bioaffinity sensor having a self-assembled monolayer interface for detection of a target molecule. In one aspect, a sensor device for detecting a target molecule includes a surface capable of attaching a thiol and a molecular monolayer formed on the surface that includes a molecular capture probe having a thiol region, a linear alkanethiol molecule having one thiol region, and a linear alkanedithiol molecule having two thiol regions, in which the molecular capture probe includes a region for receiving a target substance having a complimentary region that couples with the region of the molecular capture probe to generate a detectable signal.

8 Claims, 17 Drawing Sheets

(51) Int. Cl.
*G01N 27/30* (2006.01)
*G01N 27/327* (2006.01)

(56) References Cited

U.S. PATENT DOCUMENTS

| | | | |
|---|---|---|---|
| 7,347,974 B1* | 3/2008 | Snow et al. | 422/90 |
| 7,357,018 B2 | 4/2008 | Curry et al. | |
| 7,516,759 B2 | 4/2009 | Paxton et al. | |
| 2002/0146745 A1 | 10/2002 | Natan et al. | |
| 2002/0192722 A1* | 12/2002 | Stolowitz | B82Y 15/00 435/7.9 |
| 2004/0158051 A1* | 8/2004 | Ozkan | B82Y 5/00 536/23.1 |
| 2004/0209376 A1 | 10/2004 | Natan et al. | |
| 2005/0123937 A1 | 6/2005 | Thorp et al. | |
| 2005/0164402 A1* | 7/2005 | Belisle | B01L 3/502707 436/174 |
| 2005/0176029 A1 | 8/2005 | Heller et al. | |
| 2005/0266416 A1 | 12/2005 | Guo | |
| 2005/0281682 A1 | 12/2005 | Paxton | |
| 2007/0105119 A1* | 5/2007 | Gao et al. | 435/6 |
| 2008/0156654 A1 | 7/2008 | Wang et al. | |
| 2008/0187764 A1 | 8/2008 | Jung et al. | |
| 2009/0212275 A1 | 8/2009 | Park et al. | |
| 2010/0129656 A1 | 5/2010 | Zussman et al. | |
| 2010/0276302 A1* | 11/2010 | Raguse | G01N 27/127 205/775 |

OTHER PUBLICATIONS

Batchelor-McAuley, C. et al., "The physicochemical aspects of DNA sensing using electochemical methods", Biosens. Bioelectron. 24, 2009, pp. 3183-3190.

Campuzano, J.C. et al., "Photoemission in the High Tc Superconductors", Sep. 19, 2002, 109 pages.

Campuzano, S. et al., "Ternary monolayers as DNA recognition interfaces for direct and sensitive electrochemical detection in untreated clnical samples", Biosensors and Bioelectronics, Feb. 2011, vol. 26, pp. 3577-3583.

Chumbimuni-Torres, K.Y. et al., "Amplified potentiometric transduction of DNA hybridization using ion-loaded liposomes", Analyst, 2010, 135, pp. 1618-1623.

Das, J. et al., "Ultrasensitive Detection of DNA in Diluted Serum Using NaBH4 Electrooxidation Mediated by [Ru(NH3)6]3+ and Indium—Tin Oxide Electrodes, Langmuir 2010, 26(9), pp. 6804-6808.

Dharuman V. et al., "Ternary mixed monolayers for simultaneous DNA orientation control and surface passivation for label free DNA hybridization electrochemical sensing", Biosensors and Bioelectornics, 2010, vol. 25, pp. 2129-2134.

Harpster, M. H. et al., SERS detection of indirect viral DNA capture using colloidal gold and methylene blue as a Raman label, Biosensors and Bioelectronics, 2009, vol. 25, pp. 674-681.

Janek, R. P. et al., "Impedance Spectroscopy of Self-Assembled Monolayers on Au(111): Sodium Ferrocyanide Charge Transfer at Modified Electrodes", Langmuir 1998, 14, pp. 3011-3018.

Keighley, S. D. et al., "Optimization of label-free DNA detection with electrochemical impedance spectroscopy using PNA probes", Biosensors and Bioelectronics 24, 2008, pp. 906-911.

Kim, Y.-K., Authorized Officer, Korean Intellectual Property Office, International Search Report, International Application No. PCT/US2012/023039, Nov. 20, 2012.

Kuralay, F. et al., "Highly sensitive disposable nucleic acid biosensors for direct bioelectronics detection in raw biological samples", Talanta, Jun. 2011, vol. 85, pp. 1330-1337.

Levicky, R. et al., "Using Self-Assembly to Control the Structure of DNA Monolayers on Gold: A Neutron Reflectivity Study", J. Am. Chem. Soc., 1998, 120, pp. 9787-9792.

Liao, J.C. et al., "Development of an Advanced Electrochemical DNA Biosensor for Bacterial Pathogen Detection", J. Mol. Diagn. vol. 9, No. 2, Apr. 2007, pp. 158-168.

Liao, J.C. et al., "Use of Electrochemical DNA Biosensors for Rapid Molecular Identification of Uropathogens in Clinical Urine Specimens", J. Clin. Microbiol. Feb. 2006, pp. 561-570.

Luong, J. H.T. et al., "Biosensor technology: Technology push versus market pull", Biotechnology Advances 26 (2008) pp. 492-500.

Miranda-Castro, R. et al., "Structured Nucleic Acid Probes for Electrochemical Devices", Electroanalysis 2009, 21, No. 19, pp. 2077-2090.

Park, S.-M. et al., "Electrochemical Impedance Spectroscopy for Better Electrochemical Measurements", Analytical Chemistry, Nov. 1, 2003, pp. 455-461.

Patterson, A. et al., "Using Triplex-Forming Oligonucleotide Probes for the Reagentless, Electrochemical Detection of Double-Stranded DNA", Anal. Chem. 2010, 82, pp. 9109-9115.

Piela, B. et al., "Capacitance of the gold electrode in 0.5 M H2SO4 solution: a.c. impedance studies", Journal of Electroanalytical Chemistry 388 (1995) pp. 69-79.

Sadik, O.A. et al., "Status of biomolecular recognition using electrochemical techniques", Biosens. Bioelectron. 24, 2009, pp. 2749-2765.

Sassolas, A. et al., "DNA Biosensors and Microarrays", Chem. Rev. 2008, 108, pp. 109-139.

Seifert, M. et al., Characterization of streptavidin binding to biotinylated, binary self assembled thiol monolayers—Influence of component ration and solvent, Langmuir, 2010, vol. 26, No. 9, pp. 6386-6393.

Steel, G. J. et al., "A Screen for Dominant Negative Mutants of SEC18 Reveals a Role for the AAA Protein Consensus Sequence in ATP Hydrolysis", Molecular Biology of the Cell, vol. 11, Apr. 2000, pp. 1345-1356.

Steel, M. et al., "Gene-Trapping to Identify and Analyze Genes Expressed in the Mouse Hippocampus", Hippocampus 8, 1998, pp. 444-457.

Tosar, J.P. et al., "Electrochemical DNA hybridization sensors applied to real and complex biological samples", Bioelectron. 26, 2010, pp. 1205-1217.

Wang, J., "Electrochemical biosensors: Towards point-of-care cancer diagnostics", Biosens. Bioelectron. 21, 2006, pp. 1887-1892.

Wu, Beili et al., "Structures of the CXCR4 Chemokine GPCR with Small-Molecule and Cyclic Peptide Antagonists", Science, 2010, vol. 330, pp. 1066-1071.

Wu, J. et al., "Ternary Surface monolayers for Ultrasensitive (Zeptomole) Amperometric Detection of Nucleic Acid Hybridization without Signature Amplification", Anal. Chem., 2010, 82, pp. 8830-8837.

Zhang, J. et al., "Design of an Oligonucleotide-Incorporated Nonfouling Surface and Its Application in Electrochemical DNA Sensors for Highly Sensitive and Sequence-Specific Detection of Target DNA", Anal. Chem. 2008, 80, pp. 9029-9033.

Wang, Y. et al., "Bipolar Electrochemical Mechanism for the Propulsion of Catalytic Nanomotors in Hydrogen Peroxide Solutions", Langmuir 2006, 22, pp. 10451-10456.

Watanabe, M. et al., "Electronic detection of DNA mutation based on strand exchange reaction", Biorg. Medicinal Chemistry, 2009, 17, pp. 1494-1497.

Whitesides, G.M., "The Once and Future Nanomachine," Scientific American, Sep. 2001, 285(3):70-75.

Wildgoose, G.G. et al., "High-Temperature Electrochemistry: A Review", Electroanalysis 2004, 16, No. 16, pp. 421-432.

Wouters, D., et al., "Nanolithography and Nanochemistry: Probe-Related Patterning Techniques and Chemical Modification for Nanometer-Sized Devices," Angewandte Chemie International Edition, May 2004, 43(19):2480-2495.

Yamazaki, S. et al., "A fuel cell with selective electrocatalysts using hydrogen peroxide as both an electron acceptor and a fuel", J. Power Sources 2008, 178, pp. 20-25.

York, J. et al., "Single-molecule detection of DNA via sequence-specific links between F1-ATPase motors and gold nanorod sensors", Lab on Chip 8, 2008, pp. 415-419.

Zacharia, N. S. et al., "Enhanced speed of bimetallic nanorod motors by surface roughening", Chem. Commun., 2009, pp. 5856-5858.

(56) References Cited

OTHER PUBLICATIONS

Zerihun, T. et al., "Oxidation of formaldehyde, methanol, formic acid and glucose at ac heated cylindrical Pt microelectrodes", J. Electroanal. Chem. 1998, 441, pp. 57-63.
Zhang, L. et al., "Artificial bacterial flagella: Fabrication and magnetic control", Appl. Phys. Lett. 2009, 94, 064107.
Zhang, L. et al., Controlled propulsion and cargo transport of rotating nick el nanowires near a patterned solid surface, ACS Nano vol. 4, No. 10, pp. 6228-6234.
Adhikari, B. et al., "Polymers in sensor applications", Progress in Polymer Science, 2004, vol. 29, pp. 699-766.
Alon, U. et al., "Robustness in bacterial chemotaxis", Nature, 1999, vol. 397, pp. 168-171.
Anderson, J., "Colloid Transport by Interfacial Forces", Annu. Rev. Fluid Mec. 1989, vol. 21, pp. 61-99.
Balasubramanian, S, et al., "Thermal Modulation of Nanomotor Movement," Small, 5(13):1569-1574, Mar. 2009.
Beckmann, A. et al., "Modeling Hot Wire Electrochemistry. Coupled Heat and Mass Transport at a Directly and continuously Heated Wire", J. Phys. Chem B 2000, 104, pp. 764-769.
Behkam, B. et al., "Bacterial Flagella-Based Propulsion and On/Off Motion Control of Microscale Objects", Appl. Phys. Lett. 2007, 90, 023902.
Berg, H.C. et al., "The Rotary Motor of Bacterial Flagella", Annu. Rev. Biochem, 2003, 72, pp. 19-54.
Burdick, J., et al., "Synthetic Nanomotors in Microchannel Networks: Directional Microchip Motion and Controlled Manipulation of Cargo," Journal of the American Chemical Society, 130(26):8164-8165, Jun. 2008.
Byun, S. C., Authorized Officer, Korean Intellectual Property Office, Interntational Search Report and Written Opinion, PCT Application No. PCT/US2012/000269, Nov. 23, 2012, 10 pages.
Calvo-Marzal, P., et al., "Electrochemically-triggered motion of catalytic nanomotors," The Royal Society of Chemistry: Chemical Communications, 14(30):4509-4511, Jun. 2009.
Campuzano, S. et al., "Bacterial Isolation by Lectin-Modified Microengines", Nano Lett. 12, 2012, 396-401.
Cao, Y. W. C., Jin, R. C. & Mirkin, C. A. Nanoparticles with Raman spectroscopic fingerprints for DNA and RNA detection Science 297, 1536-1540 (2002).
Cartwright, J., "Nanomotors detect trace silver," Royal Society of Chemistry, published Aug. 14, 2009, obtained online Apr. 2015 <http://www.rsc.org/chemistryworld/News/2009/August/14080901.asp>.
Catchmark, J. M., et al., "Directed Rotational Motion of Microscale Objects Using Interfacial Tension Gradients continually Generated via Catalytic Reactions", Small 2005, 1, No. 2, pp. 202-206.
Chang, T. S. et al., "Remotely powered self-propelling particles and micropumps based on miniature diodes", Nature Mat. 2007, vol. 6, pp. 235-240.
Choi, J. W., Authorized Officer, Korean Intellectual Property Office, Interntational Search Report and Written Opinion, PCT Application No. PCT/US2012/023410, Sep. 21, 2012, 9 pages.
Choi, S., Authorized Officer, Korean Intellectual Property Office, Interntational Search Report and Written Opinion, PCT Application No. PCT/US2011/053783, May 4, 2012, 8 pages.
Demirok, U.K., et al., "Ultrafast Catalytic Alloy Nanomotors," Angewandte Chemie International Edition, 47 (48):9349-9351, Oct. 2008.
Fischer, T., Agarwal, A. & Hess, H. "A smart dust biosensor powered by kinesin motors", Nature Nanotech. 4, 2009, pp. 162-166.
Flechsig, G. -U. et al., Investigation of Deposition and Stripping Phenomena at the Heated Gold Wire Electrode in Comparison to the Rotating Disk Electrode: Copper(II), Mercury(II), and Arsenic(III), Electroanalysis 2001, 13, 786.
Fournier-Bidoz, S. et al., "Synthetic self-propelled nanorotors", Chem. Commun. 2005, pp. 441-443.
Frischmuth, K. et al., "On Modelling Heat Transfer in Chemical Microsensors", Int. J. Eng. Sci. vol. 34, No. 5, pp. 523-530.

Gao, W. et al., "Highly Efficient Catalytic Microengines: Template Electrosynthesis of Polyaniline/Platinum Microtubes", J. Am. Chem. Soc., Jul. 2011, vol. 133, No. 31, pp. 11862-11864.
Gao, W. et al., "Magnetically Powered Flexible Metal Nanowire Motors", J. Am. Chem. Soc., 2010, 132, pp. 14403-14405.
Ghosh, A. et al., "Controlled Propulsion of Artificial Magnetic Nanostructured Propellers", Nano Lett. 2009, vol. 9, No. 6, pp. 2243-2245.
Gibbs, J. G. et al., "Autonomously motile catalytic nanomotors by bubble propulsion", Appl. Phys. Lett. 2009, 94, 163104.
Gibbs, J. G. et al., "Design and Characterization of Rotational Multicomponents Catalytic Nanomotors", Small 2009, 5, No. 20, pp. 2304-2308.
Goel, A. et al., "Harnessing biological motors to engineer systems for nanoscale transport and assembly", Nature Nanotechnology 2008, vol. 3, pp. 465-475.
Gooding, J.J., "Electrochemical DNA hybridization biosensors", Electroanalysis 2002, 14, No. 17, pp. 1149-1156.
Goszner K. et al., "The Decomposition of Hydrogen Peroxide on Silver-Gold Alloys", J. Catal. 32, 1974, pp. 175-182.
Gründler, P. et al., "Principles and Analytical Applications of Heated Electrodes", Microchim. Acta 154, 2006, pp. 175-189.
Gründler, P. et al., "The Technology of Hot-Wire Electrochemistry", Electroanalysis 1999, 11, No. 4, pp. 223-228.
Gründler, P. et al., Hot-wire Electrodes: Voltammetry Above the Boiling Point, Analyst, 1996, vol. 121, pp. 1805-1810.
Hall, S.B. et al., "Electrochemical oxidation of hydrogen peroxide at platinum electrodes. Part III: Effect of temperature", Electrochim. Acta 44, 1999, pp. 2455-2462.
He, Y. et al., "Designing Catalytic Nanomotors by Dynamic Shadowing Growth", Nano Lett. 2007, vol. 7, No. 5, 1369-1375.
Herr, J.K. et al., "Aptamer-conjugated nanoparticles for selective collection and detection of cancer cells", Anal. Chem. 2006, 78, pp. 2918-2924.
Hess, H. et al., "Light-Controlled Molecular Shuttles Made from Motor Proteins Carrying Cargo on engineered Surfaces", Nano. Letters, 2001, vol. 1, No. 5, pp. 235-239.
Hess, H. et al., "Biomolecular motors", nanotoday, 2005, pp. 22-29.
Hianik, T. et al."Influence of ionic strength, pH and aptamer configuration for binding affinity to thrombin" Bioelectrochemistry 70, 2007, pp. 127-133.
Hill, H.D. et al., "The bio-barcode assay for the detection of protein and nucleic acid targets using DTT-induced ligand exchange" Nature Protocols 1, 2006, pp. 324-336.
Honda et al., "Electrochemical Behavior of H2O2 AT Ag In HClO4 Aqueous Solution", Electrochim. Acta, vol. 31, No. 3, 1986, pp. 377-383.
Hong, S. R., Authorized Officer, Korean Intellectual Property Office, Interntational Search Report and Written Opinion, PCT Application No. PCT/US2013/026757, Jul. 25, 2013, 14 pages.
Hong, Y. et al., "Chemotaxis of Nonbiological Colloidol Rods", Phys. Rev. Lett. 2007, 99, 178103.
Howse, J. R. et al., "Self-Motile Colloidal Particles: From Directed Propulsion to Random Walk", Phys. Rev. Lett 2007, 99, 048102.
Huang, S. L. et al., "Acoustically active liposomes for drug encapsulation and ultrasound-triggered release", Biochimia et Biophysica Acta., Aug. 12, 2004, vol. 1665, pp. 134-141.
Ibele, M. et al., "Schooling Behavior of Light-Powered Autonomous Micromotors in Water", Angew. Chem. Int. Ed. 2009, 48, pp. 3308-3312.
Ibsen, S. et al., "A Novel Nested Liposome Drug Delivery Vehicle Capable of Ultrasound Triggered Release of its Payload", J Control Release, Nov. 7, 2011, vol. 155, No. 3, pp. 358-366.
Ismagilov, R. F. et al., "Autonomous Movement and Self-Assembly", Angew. Chem. Int. Ed. 2002, 41, No. 4, pp. 352-654.
Kagan, D., et al., "Chemical Sensing Based on Catalytic Nanomotors: Motion-Based Detection of Trace Silver," Journal of the American Chemical Society, Aug. 2009, 131(34):12082-12083.
Keating, C.D. et al., "Striped metal nanowires as building blocks and optical tags", Adv. Materials, 2003, 15, pp. 451-454.

(56) References Cited

OTHER PUBLICATIONS

Klibanov, A. L. et al., "Ultrasound-triggered release of materials entrapped in microbubble-liposome constructs: a tool for targeted drug delivery", J Control Release, Nov. 20, 2010, vol. 148, No. 1, pp. 13-17.
Kline, T. R. et al., "Catalytic nanomotors: remote-controlled autonomous movement of striped metallic nanorods", Angew. Chem. Int., 2005, Ed 44, pp. 744-746.
Lahav, M. et al., "Core-Shell and Segmented Polymer-Metal Composite Nanostructures", Nano Letters, 2006, vol. 6, No. 9, pp. 2166-2171.
Laocharoensuk, R., et al., "Carbon-Nanotube-Induced Acceleration of Catalytic Nanomotors," ACS Nano, 2008, 2 (5):1069-1075.
Lee, D.-W., Authorized Officer, Korean Intellectual Property Office, Interntational Search Report and Written Opinion, PCT Application No. PCT/US2011/030211, Jan. 2, 2012, 8 pages.
Lee, J. S. et al., "Silver Nanoparticle-oligonucleotide conjugates based on DNA with triple cyclic disulfide moieties", Nano Letters 2007, 7, pp. 2112-2115.
Liu, W., et al., "Enzymatically Synthesized Conducting Polyaniline," Journal of the American Chemical Society, 1998, 121(1):71-78.
Luo, X., et al., "Enzymatic Nanolithography of Polyaniline Nanopatterns by Using Peroxidase-Modified Atomic Force Microscopy Tips," Chemistry—A European Journal, 2009, 15(21):5191-5194.
Manesh, K. et al., "Motion control at the nanoscale", Small 2010, 6, pp. 338-345.
Manesh, K. M., et al., "Nanomotor-based writing of surface microstructures," The Royal Society of Chemistry: Chemical Communications, 2010, 46(31):5704-5706.
Mano, N. et al., "Bioelectrichemical Propulsion", J. Am. Chem. Soc. 2005, 127, pp. 11574-11575.
Mascaro, L.H. et al., "Underpotential deposition of silver on polycrystalline platinum studied by cyclic voltammetry and rotating ring-disc techniques", J. Chem. Soc., Faraday Trans., 1997, 93(22), pp. 3999-4003.
Mei, Y. et al., "Versatile Approach for Integrative and Functionalized Tubes by Strain Engineering of Nanomembranes on Polymers", Adv. Mater., Oct. 15, 2008, vol. 20, No. 21, pp. 4085-4090.
Mihajlovic, G. et al., "All-electrical switching and control mechanism for actomyosin-powered nanoactuators", Appl. Physics Lett. 2004, 85, 1060.
Mirkovic, T. et al., "Nanolocomotion: catalytic nanomotors and nanorotors", Small 2010, 6, No. 2, 159-167.
Miyamoto, Y. et al., "Direct Inhibition of Microtubule-Based Kinesin Motility by Local Anesthetics", Biophys. J. 2000, 78, pp. 940-949.
Niidome, Y. et al., "Characterization of silver ions adsorbed on gold nanorods: surface analysis by using surface-assisted laser desorption/ionization time-of-flight mass spectrometry", Chem. Commun, 2009, pp. 1754-1756.
Okahata, Y. et al., "Hybridization of nucleic-acids immobilized on a quartz crystal microbalance", J. Am. Chem. Soc., 1992, 114, pp. 8299-8300.
Orendorff, C. J. et al., "Quantitation of Metal Content in the Silver-Assisted Growth of Gold Nanorods", J. Phys. Chem. B, 2006, 110, pp. 3990-3994.
Orozco, J. et al., "Dynamic Isolation and Unloading of Target Proteins by Aptamer-Modified Microtransporters", Anal. Chem., 83, 2011, pp. 7962-7969.
Ozin, G.A., et al., "Dream Nanomachines," Advanced Materials, Dec. 2005, 17(24):3011-3018.
Pal, S., et al., "Stable silver nanoparticle-DNA conjugates for directed self-assembly of core-satellite silver-gold nanoclusters", Chem. Commun., 2009, 40, pp. 6059-6061.
Palecek, E. et al., "Detecting DNA hybridization and damage", Anal. Chem. 2001, 73, pp. 74A-83A.
Park, Jong Chul, Authorized Officer, Korean Intellectual Property Office, International Search Report and Written Opinion mailed on Jun. 3, 2011 for International Application No. PCT/US2010/046558, 10 pages.
Parsons et al., "The oxidation of small organic molecules", J. Electroanal. Chem., 1988, 257, pp. 9-45.
Paxton et al., "Chemical Locomotion", Angew. Chemie. Int. Ed. 2006, 45, pp. 5420-5429.
Paxton, W. F. et al., "Catalytically Induced Electrokinetics for Motors and Micropumps", J. Am. Chem. Soc. 2006, 128, pp. 14881-14888.
Paxton, W.F. et al., "Catalytic Nanomotors: Autonomous Movement of Striped Nanorods", J. Am Chem. Soc. 2004, 126, pp. 13424-13431.
Paxton, W.F. et al., "Motility of Catalytic Nanoparticles through Self-Generated Forces", Chem. Eur. J. 2005, 11, pp. 5462-6470.
Piner, R.D., et al., "Dip-Pen Nanolithography", Science, 1999, 283(5402):661-663.
Piunno, P. A. E. et al., "Fiber optic DNA sensor for fluorometric nuclei acid determination", Anal. Chem. 1995, 67, pp. 2635-2643.
Prieve, D. C., "Changes in zeta potential caused by a dc electric current for thin double layers", Colloids Surf. A: Physicochem. Eng. Aspects, 2004, 250, pp. 67-77.
Rosi, N. L. et al., "Nanostructures in biodiagnostics", Chem. Rev. 2005, 105, pp. 1547-1562.
Salaita, K., et al., "Applications of dip-pen nanolithography," Nature Nanotechnology, Feb. 2007, 2(3):145-155.
Solovev, A. A. et al., Catalytic Microtubular Jet Engines Self-Propelled by Accumulated Gas Bubbles, Small, Jul. 17, 2009, vol. 5, No. 14, pp. 1688-1692.
Strohmeier, R. et al., "Control of Cell Shape and Locomotion by External Calcium", Exp. Cell Res. 1984, 154, pp. 412-420.
Sundararajan, S., et al., "Catalytic Motors for Transport of Colloidal Cargo", Apr. 2008, Nano Letters, 8 (5):1271-1276.
Suwansa-Ard, S. et al., "Prussian blue dispersed sphere catalytic labels for amplified electronic detection of DNA", Electroanalysis, 2008, 20, pp. 308-312.
Takeda, S., et al., "Lithographing of Biomolecules on a Substrate Surface Using an Enzyme-Immobilized AFM Tip," Nano Letters, Oct. 2003, 3(11):1471-1474.
Taton, T. A. et al., "Scanometric DNA Array Detection with Nanoparticle Probes", Science 2000, 289, pp. 1757-1759.
Thompson, D. G. et al., "Ultrasensitive DNA detection using oligonucleotide-silver nanoparticle conjugates", Anal. Them., 2008, 80, 2805-2810 (2008).
Tokareva, I. et al., "Hybridization of oligonucleotide-modified silver and gold nanoparticles in aqueous dispersions and on gold films", J. Am. Chem. Soc. 2004, 126, pp. 15784-15789.
Tseng, A. A. et al., Nanofabrication by scanning probe microscope lithography: A review, J. Vac. Sci. Technol., 2005, B, 23, pp. 877-894.
Van Den Heuvel, M.G.L et al., "Motor Proteins at Work for Nanotechnology", Science 2007, 317, pp. 333-336.
Wachholz, F. et al., "Temperature pulse modulated amperometry at compact electrochemical sensors", Electrochem. Commun. 2007, 9, pp. 2346-2352.
Wang, J. et al., "Motion Control at the Nanoscale", Small, 2010, 6, No. 3, pp. 338-345.
Wang, J. et al., "Silver-enhanced colloidal gold electrochemical stripping detection of DNA hybridization", Langmuir 2001, 17, pp. 5739-5741.
Wang, J., "Can man-made nanomachines compete with nature biomotors?" ACS Nano, Jan. 2009, 3(1):4-9.
Wang, J., "From DNA biosensors to gene chips", Nucl. Acids Res., 2000, 28, pp. 3011-3016.
Wang, J., "Nanomaterial-based amplified transduction of biomolecular interactions", Small 2005, 1, pp. 1036-1043.
Wu et al., "Potentiometric Detection of DNA Hybridization using Enzyme-induced Metallization and a Silver Ion Selective Electrode," Analytical Chemistry, vol. 81, No. 24, Dec. 15, 2009, pp. 1007-1012.

(56) References Cited

OTHER PUBLICATIONS

Carpini et al., "Oligonucleotide-modified screen-printed gold electrodes for enzyme-amplified sensing of nucleic acids," Biosensors and Bioelectronics. 2004, 20: 167-175,.
Mallouk, T. E. & Sen, A. "Powering nanorobots." Sci. Amer. 300, 72-77 (2009).
Ferguson, J. A., Boles, T. C., Adams, C. P. & Walt, D. R. "A fiber-optic DNA biosensor microarray for the analysis of gene expression," Nat. Biotechnol. 14, 1681-1684 (1996).
"Transducer" definition from dictionary.com, retrieved from the Internet on Oct. 4, 2016: http://www.dictionary.com/browse/transducer., 4 pages.

\* cited by examiner

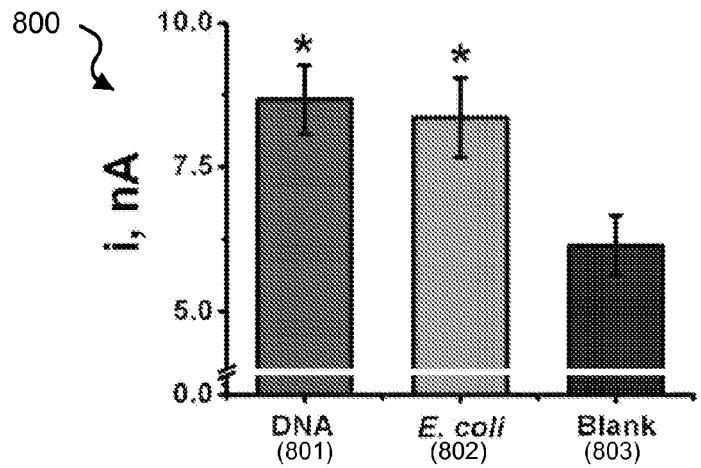
FIG. 8
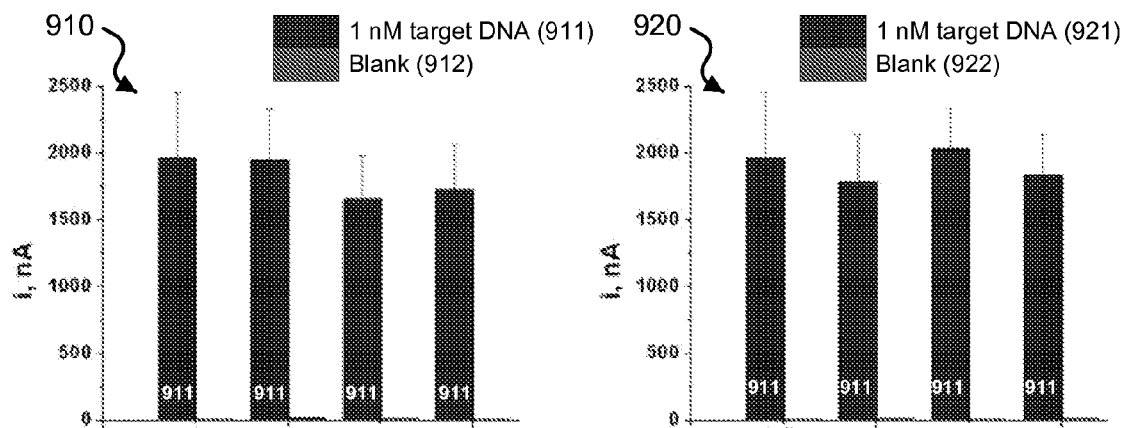
FIG. 9A
FIG. 9B
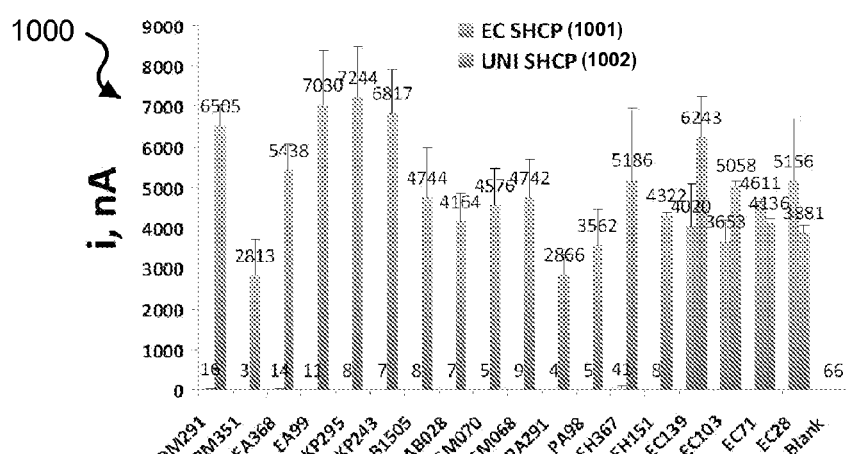
FIG. 10

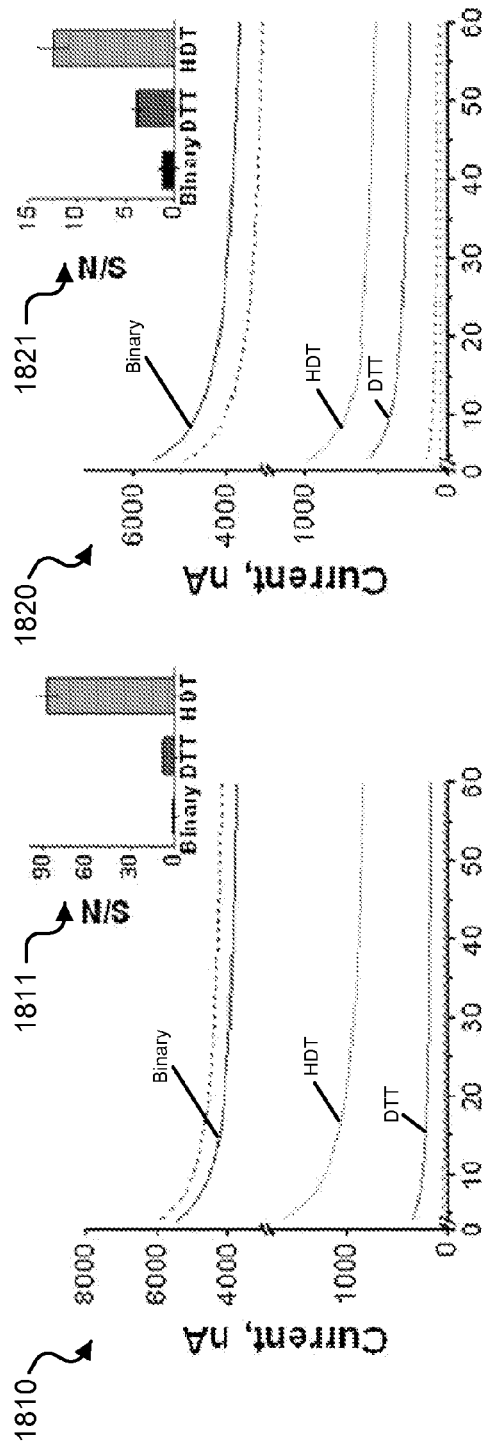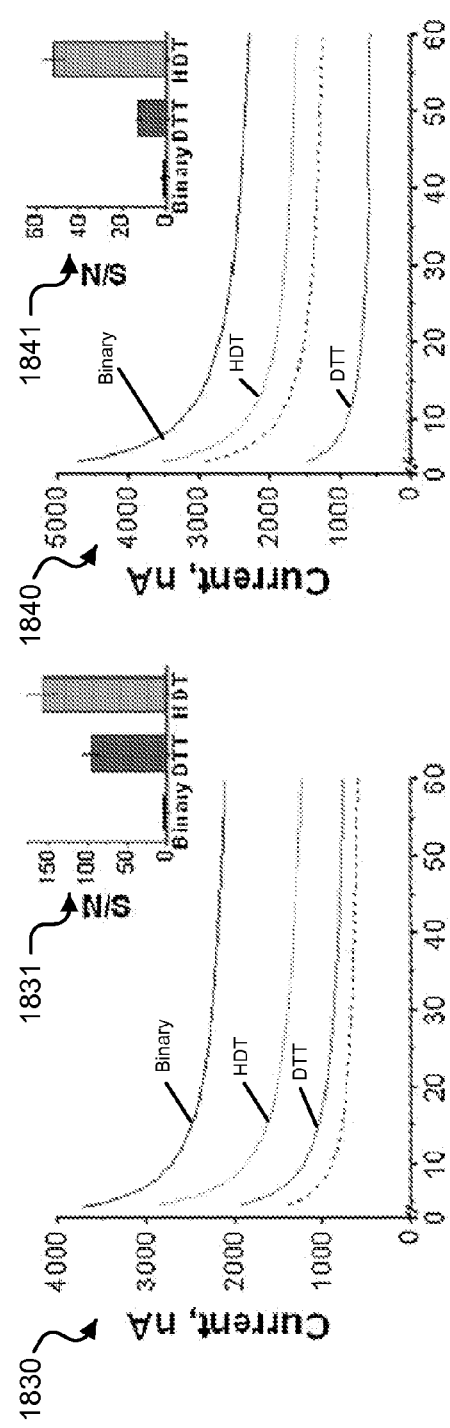

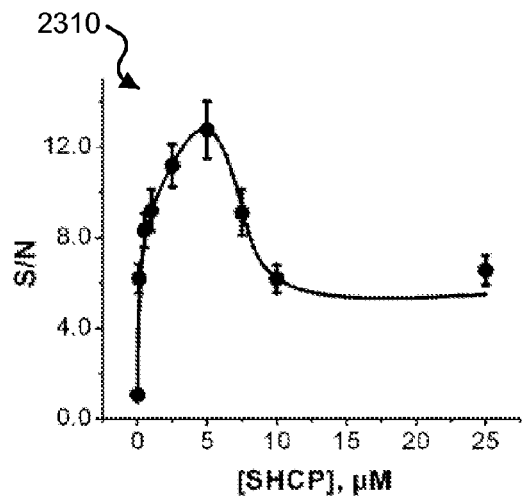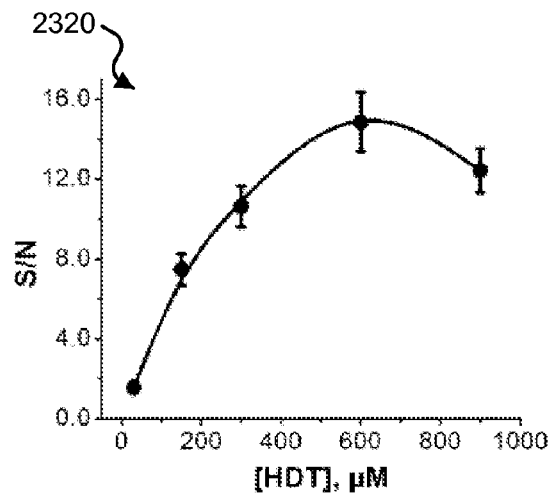
FIG. 23A  FIG. 23B
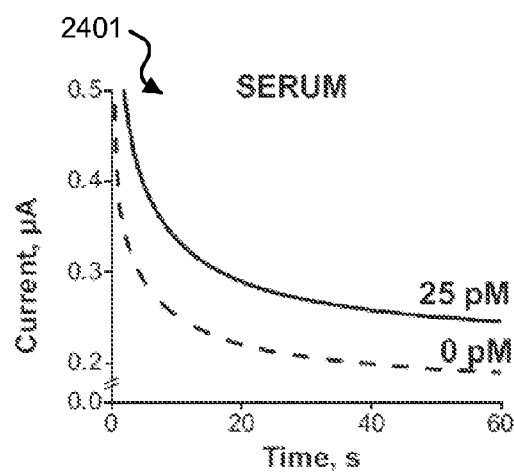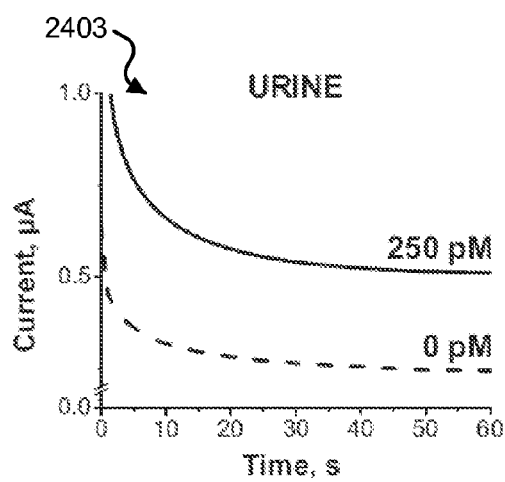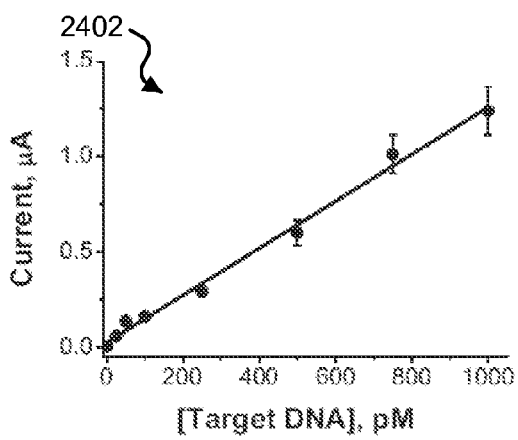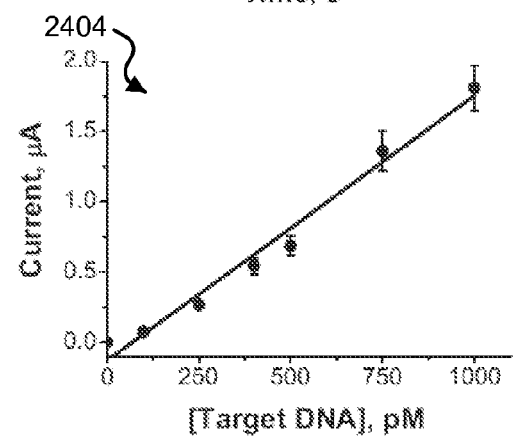
FIG. 24

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide: EC SHCP
<220> FEATURE:
<221> NAME/KEY: misc_feature
<222> LOCATION: (1)..(1)
<223> OTHER INFORMATION: Thiol at 5'-end

<400> SEQUENCE: 1
``` tattaactttt actcc                                                     15

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide: UNI SHCP
<220> FEATURE:
<221> NAME/KEY: misc_feature
<222> LOCATION: (1)..(1)
<223> OTHER INFORMATION: Thiol at 5'-end

<400> SEQUENCE: 2
gttcccctac ggttaccttt                                                 19

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide: EC FITC-DP
<220> FEATURE:
<221> NAME/KEY: misc_feature
<222> LOCATION: (15)..(15)
<223> OTHER INFORMATION: FITC at 3'-end

<400> SEQUENCE: 3
cttcctcccc gctga                                                      15

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide: UNI FITC-DP
<220> FEATURE:
<221> NAME/KEY: misc_feature
<222> LOCATION: (18)..(18)
<223> OTHER INFORMATION: FITC at 3'-end

<400> SEQUENCE: 4
gttacgactt caccccag                                                   18

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide: Complementary target
      EC DNA

<400> SEQUENCE: 5
tcagcgggga ggaagggagt aaagttaata                                      30

<210> SEQ ID NO 6
<211> LENGTH: 37
<212> TYPE: DNA
<213> ORGANISM: Artificial Sequence
<220> FEATURE:
<223> OTHER INFORMATION: Synthetic oligonucleotide: Non-complementary
      target EC DNA

<400> SEQUENCE: 6
ctggggtgaa gtcgtaacaa ggtaaccgta ggggaac                              37

<210> SEQ ID NO 7

```
<211> LENGTH: 30
<212> TYPE: DNA
<213> ORGANISM: Artificial Sequence
<220> FEATURE:
<223> OTHER INFORMATION: Synthetic oligonucleotide: 2-Base mismatched EC

<400> SEQUENCE: 7
tcagcgggga ggaagggagt caagtgaata                                            30

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide: 3-Base mismatched EC

<400> SEQUENCE: 8
tcaacgagga gcaagggagt aaagttaata                                            30
```

BIOAFFINITY SENSORS BASED ON SURFACE MONOLAYERS

CROSS-REFERENCE TO RELATED APPLICATIONS

This patent document is a 35 USC §371 National Stage application of International Application No. PCT/US2012/023039 filed Jan. 27, 2012, which claims priority of U.S. Provisional Patent Application No. 61/437,557, entitled "DNA HYBRIDIZATION BIOSENSORS BASED ON TERNARY SURFACE MONOLAYERS" and filed Jan. 28, 2011; the entire disclosures of which are incorporated herein by reference for all purposes.

STATEMENT REGARDING FEDERALLY SPONSORED RESEARCH OR DEVELOPMENT

This invention was made with government support under grant/contract U01 AI075565 awarded by the National Institutes of Health (NIH), along with grant/contract CHE 0506529, awarded by the National Science Foundation (NSF). The government has certain rights in the invention.

BACKGROUND

This patent document relates to systems, devices, and processes related to biosensor technologies.

A biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

SUMMARY

Techniques, systems, devices and materials are disclosed for implementing a bioaffinity sensor based on ternary self-assembled monolayers surface interfaces.

In one aspect of the disclosed technology, a sensor device for detecting a target molecule includes a surface capable of attaching a thiol and a molecular monolayer formed on the surface, the molecular monolayer including a molecular capture probe having a thiol region, a linear alkanethiol molecule having one thiol region, and a cyclic alkanedithiol molecule having two thiol regions, in which the molecular capture probe includes a region for receiving a target substance having a complimentary region that couples with the molecular capture probe to generate a detectable signal indicating a coupling event.

In another aspect, a sensor device for detecting a target molecule includes a surface capable of attaching a thiol and a molecular monolayer formed on the surface, the molecular monolayer including a molecular capture probe having a thiol region, a linear alkanethiol molecule having one thiol region, and a linear alkanedithiol molecule having two thiol regions, in which the molecular capture probe includes a region for receiving a target substance having a complimentary region that couples with the region of the molecular capture probe to generate a detectable signal.

In another aspect, a sensor device for detecting a target molecule includes a detecting electrode having a surface capable of attaching a thiol, a sensor chip substrate on which the detecting electrode is located, a reference electrode located on the sensor chip substrate that is electrically coupled to the detecting electrode, and a self-assembled monolayer formed on the surface that includes a molecular capture probe having a thiol region, a linear alkanethiol molecule having one thiol region, and a linear alkanedithiol molecule having two thiol regions, in which the molecular capture probe includes a region for receiving a target substance having a complimentary region that couples with the region of the molecular capture probe to generate a detectable electrical signal measured between the detecting electrode and the reference electrode during a coupling event.

In another aspect, a method of producing a self-assembled monolayer surface interface for detection of a target substance includes immobilizing a linear alkanedithiol molecule having two thiol regions and a molecular capture probe having a thiol region concurrently on a surface capable of attaching a thiol to form a co-immobilized monolayer and immobilizing a linear alkanethiol molecule having one thiol region to the surface having the co-immobilized monolayer to form a self-assembled monolayer surface interface, in which the self-assembled monolayer surface interface detects a target substance at a coupling region on the molecular capture probe and generates a signal.

In another aspect, a self-assembled monolayer surface for detecting a target molecule includes a surface capable of attaching a thiol, a linear alkanethiol molecule having one thiol region that attaches to the surface at the one thiol region, a cyclic alkanedithiol molecule having two thiol regions that attaches to the surface at each of the two thiol regions, and a molecular capture probe having a thiol region and a capture region for receiving a target substance having a complimentary region that couples with the molecular capture probe at the capture region to generate a detectable signal, in which the molecular capture probe attaches to the surface at the thiol region with an orientation that presents the capture region.

In another aspect, a self-assembled monolayer surface for detecting a target molecule includes a surface capable of attaching a thiol, a linear alkanethiol molecule having one thiol region that attaches to the surface at the one thiol region, a linear alkanedithiol molecule having two thiol regions that attaches to the surface at each of the two thiol regions, and a molecular capture probe having a thiol region and a capture region for receiving a target substance having a complimentary region that couples with the molecular capture probe at the capture region to generate a detectable signal, in which the molecular capture probe attaches to the surface at the thiol region with an orientation that presents the capture region.

The subject matter described in this patent document can be implemented in specific ways that provide one or more of the following features. For example, the described techniques can be used for determination of a single copy of a specific nucleic acid sequence in biological fluids without polymer chain reaction (PCR) amplification. Also, the described techniques can be used to detect the probe-target duplex in presence of a large excess of non-complementary nucleic acid. In addition, the described techniques can be used for direct measurement of nucleic acids in undiluted biological matrices. The disclosed nucleic acid hybridization biosensors can be used as genosensor interfaces with greatly improved signal-to-noise ratio (S/N) and non-fouling characteristics. The sensitivity and high specificity of the disclosed biosensors can be implemented a wide range of applications including nucleic acid testing, including clinical diagnostics, biothreat detection, food safety, and forensic analysis.

BRIEF DESCRIPTION OF THE DRAWINGS

FIG. 8 shows a data graph showing the detection ability of exemplary ternary monolayer-based biosensors for E. coli target DNA and E. coli target rRNA.

FIGS. 9A and 9B show graphs of data from ternary monolayer-based DNA biosensors spiked in pure buffer and human serum and urine.

FIG. 10 shows a graph of chronoamperometric data from exemplary ternary monolayer-based sensors after hybridization with uropathogenic clinical isolates.

FIGS. 18A-18D show data plots of exemplary chronoamperometric signal responses of binary and ternary SAM interfaces to target DNA in clinical samples.

FIGS. 23A and 23B show data plots demonstrating the relationship of the S/N ratio with the concentration of the molecular capture probe and the dithiol of the ternary interface on rough gold surface printed electrodes.

FIG. 24 shows data plots of chronoamperometric response data obtained of target DNA on ternary interface-based biosensors after hybridization in serum or urine.

Like reference symbols and designations in the various drawings indicate like elements.

DETAILED DESCRIPTION

Figure 1:
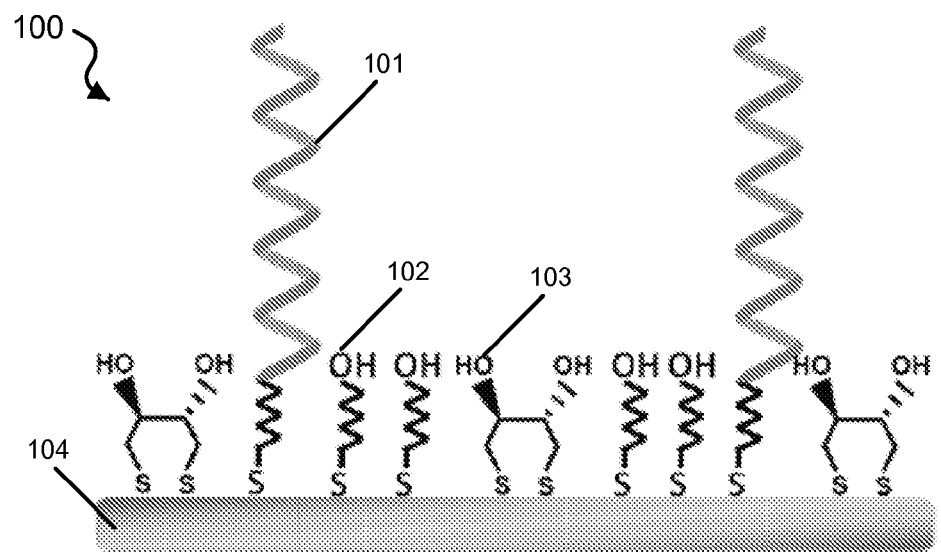
FIG. 1 shows a schematic illustration of an exemplary ternary SAM interface.

A self-assembled monolayer (SAM) is a self-organized layer of typically amphiphilic molecules in which one end of the molecule shows a specific affinity for a substrate material. SAM molecules can include a head group that anchors the molecule to the substrate, as well as a tail or functional group at the terminal end. SAM layers can be formed by the chemisorption of head groups onto a substrate material from the vapor or liquid phase. Alkanethiols are commonly used molecules to form SAM surfaces on gold substrates. Alkanethiols are molecules with an alkyl chain as the back bone and a S—H head group. For example, a sulfur head of an alkanethiol can exhibit a strong affinity to a gold substrate. Sulfur-gold interactions, which are semi-covalent, can facilitate the formation of an alkanethiol SAM on a gold substrate. SAMs can be used in a variety of applications to engineer the properties of materials, e.g., molecular adhesion, chemical resistance, molecular recognition, and biocompatibility, among others.

Surface chemistry can play an important role in the overall performance of biosensor technologies. For example, surface chemistry involving SAMs formed over substrates can influence the reactivity, accessibility, and stability of biosensor devices. For example, SAM assemblies can also be used to prevent nonspecific adsorption of undesired substances and reduce unrelated background noise from an acquired signal by a biosensor.

Techniques, systems, devices and materials are disclosed for implementing a bioaffinity sensor based on self-assembled monolayer (SAM) surface interfaces that use ternary and other monolayers.

The detection and determination of a target biomolecules and biological materials, e.g., single copies of a specific nucleic acid sequence, in fluids and biological matrices can pose a significant challenge in many applications. For example, background contributions (e.g., noise) and non-specific adsorption effects at the interface between the biologically sensitive component and the transducer element of a biosensor can lead to poor or inaccurate results in bioaffinity assays.

In some examples, the disclosed technology can include electrochemical nucleic acid hybridization biosensors based on engineered surface interfaces having a ternary self-assembled monolayer. For example, techniques, systems, and devices are described for implementing bioaffinity assays using electrochemical nucleic acid hybridization (also referred to as 'genosensors') incorporating a ternary SAM interface between a detecting surface of a working electrode and a target nucleic acid substance. In other examples, the disclosed technology can include other electrochemical immunoassay-, protein-, and cell-based biosensors for different target biomolecules (e.g., lipids, carbohydrates, enzymes, hormones, glycoproteins, glycolipids, proteins, organelles, cells, endotoxins, viruses, and other biological materials and living organisms) using the described ternary SAM interface. Also, for example, the disclosed technology can include non-electrochemical bioaffinity detection schemes incorporating the described ternary SAM interface, e.g., surface plasmon resonance (SPR) and quartz crystal microbalance characterization techniques. Some exemplary applications can include clinical diagnostics, biothreat detection, food safety, and forensic analysis. Implementation of the disclosed ternary SAM-based bioaffinity sensor technology can provide advantages including large signal-to-noise ratio (S/N), high sensitivity and specificity, low cost, minimal power consumption, independence from sample turbidity, portability, and non-fouling characteristics.

Exemplary genosenors and implementations of gene-based assays including ternary SAM interfaces are described for detection and testing applications of target nucleic acids in complex biological matrices, e.g., without PCR amplification, providing large S/N characteristics with minimal background contributions and high reproducibility. In some examples, detection of a nucleic acid target can be implemented by the ternary SAM based genosensor in the presence of non-complementary targets (e.g., other nucleic acids in complex biological matrices such as serum, urine, blood, etc.) without employing hybridization buffers or ancillary signal amplification means, e.g., thereby minimizing interference created by of other biomolecules.

In one aspect of the disclosed technology, a molecular monolayer can include a ternary SAM assembly on a sensor interface that can be implemented to dramatically improve the signal-to-noise characteristics and hence greatly lower the detection limits of bioaffinity sensing devices, systems and techniques.

FIG. 1 shows a schematic illustration of an exemplary ternary SAM interface 100, which can be implemented in a bioaffinity sensor of the disclosed technology, e.g., a ternary SAM-based electrochemical DNA hybridization biosensor. The ternary SAM interface 100 can include three self-assembled monolayers that self-assemble on a surface 104 that can attach to a thiol group. This thiol reactive surface can include gold or other materials. In some examples, the three self-assembled monolayers can include a thiolated capture probe (SHCP) 101, a short chain thiol 102, and a ternary thiol substance 103. As shown in FIG. 1, the exemplary thiolated capture probe 101 can include a thiol-derivatized single-stranded oligonucleotide probe. The thiolated capture probe 101 can include other thiolated nucleic acid capture probes, e.g., aptamers, peptide nucleic acids (PNA), and hairpin probes. The thiolated capture probe 101 can include other thiolated compounds (e.g., mercapto-carboxylic acid compounds) having a terminal functional group that can attach a biomolecule (e.g., a nucleic acid-, lipid-, carbohydrate-, or protein-based biomolecule) to form the capture probe. The exemplary short chain thiol 102 can include a linear alkanethiol, e.g., 6-mercapto-1-hexanol (MCH). For example, MCH can self-assemble on a gold surface at a thiol region of MCH. The ternary thiol substance 103 can include a dithiol, e.g., an alkanedithiol, which can chemisorb onto a gold surface via two Au—S bonds. For example, the exemplary ternary thiol substance 103 can be configured as a cyclic alkanedithiol, e.g., the α,ω-alkanedithiol dithiothreitol (DTT) as shown in FIG. 1. For example, DTT can self-assemble on a gold surface at the thiol regions of DTT and expose two hydroxyl groups at the outer surface. The ternary SAM interface 100 that can be prepared by an exemplary one-step co-immobilization of SHCP and DTT and subsequent assembly of MCH, e.g., to form a ternary SAM interface SHCP/DTT+MCH. Exemplary techniques to produce ternary SAM interface 100 are described later in this patent document.

The exemplary ternary SAM interface 100 can produce functionalized surfaces with highly compact SAMs exhibiting low pinhole density. For example the low pinhole density of the disclosed ternary SAM interfaces can be attributed to the coupling of the cyclic- and linear-configuration of "backfillers" into pinhole defects. For example, pinhole defects may be often found in binary and other monolayer surface interfaces, which can be associated with higher background noise and poor target signal detection of electrochemical biosensors. Electrochemical biosensor devices and systems implementing the disclosed ternary SAM interface 100 include the ternary thiol substance 103, such as DTT, which can provide effective backfilling and result in remarkably low background noise and highly sensitive target signal detection, even in the presence of complex sample matrixes. Additionally, non-electrochemical biosensor devices and systems implementing the disclosed ternary SAM interface 100, e.g., using SPR and microbalance characterization techniques, can exhibit remarkably low background signal perturbations and highly sensitive target signal detection due to the effective back-filling of the surface interface.

The exemplary ternary surface monolayers interface 100 can includes the thiolated capture probe 101 co-assembled with the ternary thiol substance 103 and subsequent assembly of the short chain thiol 102, e.g., SHCP/DTT+MCH. Exemplary SHCP/DTT+MCH interfaces can produce substantially large signal-to-noise characteristics, e.g., in electrochemical nucleic acid hybridization biosensors. Additionally, remarkably low detection limits can be achieved using the disclosed ternary monolayer based bioaffinity sensors. For example, DNA hybridization biosensor devices employing the disclosed ternary SAM interface can obtain signal detection at the zeptomole level without additional target or signal amplification substances, such as horseradish peroxidase (HRP) tags and 3,3',5,5'-tetramethylbenzidine (TMB) co-substrates. For example, bioaffinity sensors of the disclosed technology can detect targets on the order of 40 zeptomoles (in 4 μL samples), as well as on the order of 1 colony forming unit (CFU) per sensor for exemplary *Escherichia coli* based hybridization sensors, shown later in this patent document. These sensitive detection limits produced by the disclosed technology can be attributed, for example, to lower pinhole defects in the monolayer and higher resistance to nonspecific adsorption to the capture probe.

For example, biosensors having a ternary SAM interface, e.g., configured to have SHCP/DTT+MCH surface assemblies, showed superior signal sensitivity and signal-to-noise characteristics as compared to biosensors with binary and monocomponent surface assemblies. The exemplary ternary SAM interfaces were shown to have lower pinhole defects in the monolayer and greater resistance to nonspecific adsorption, e.g., by the OH-richer hydrophilic environment of the dithiol backfiller DTT, which can minimize undesirable background contributions. The exemplary ternary SAM interfaces can achieve high target specificity without any deliberate signal amplification, e.g., such as using amplification techniques involving horseradish peroxidase (HRP) tag and its 3,3',5,5'-tetramethylbenzidine (TMB) co-substrate.

Exemplary implementations were performed that demonstrate the disclosed bioaffinity sensors employing ternary SAM interfaces in biosensing applications. Results of these exemplary implementations are described herein. For example, implementations were performed comparing exemplary ternary SAM interfaces of the disclosed technology with binary and monocomponent monolayer interfaces. Exemplary characterizations that include impedance spectroscopy and cyclic voltammetric techniques were performed to characterize surface coverage. Exemplary materials, apparatuses, and techniques to produce and implement bioaffinity sensors including ternary SAM interfaces of the disclosed technology are described herein.

Materials used in the exemplary implementations included dithiothreitol (DTT), 6-mercapto-1-hexanol (MCH), 3-mercaptopropionic acid (MPA), Trizma® hydrochloride (Tris-HCl), ethylenediaminetetraacetic acid, human serum (from human male AB plasma), and bovine serum albumin (BSA), which were obtained from Sigma-Aldrich (St. Louis, Mo.) and used without further purification. Ethylene glycol-terminated thiol (HS—$(CH_2)_{11}$-$EG_2$-OH, OEG) was acquired from ProChimia (Sopot, Poland). The blocking agent casein was obtained from Pierce (Rockford, Ill.). Anti-fluorescein-horseradish peroxidase (anti-FITC-HRP) Fab fragments were acquired from Roche (Mannheim, Germany). Tetramethyl benzidine (TMB) solution was acquired from Neogen (Lexington, Ky.) in a ready-to-use reagent format (e.g., K-Blue enhanced-activity substrate, also containing $H_2O_2$). A solution of $K_3Fe(CN)_6$ and $K_4Fe(CN)_6$ (Sigma-Aldrich), 5 mM in each component and prepared in 0.1 M KCl, was used for electrochemical impedance spectroscopy (EIS) and cyclic voltammetry (CV) measurements.

Synthetic oligonucleotides used in the exemplary implementations were acquired from Thermo Fisher Scientific (Ulm, Germany), which are listed in Table 1. It is noted, for example, that the exemplary sequence of the 30-mer complementary target *E. coli* (EC) DNA listed in Table 1 is a copy of a partial region of the *E. coli* 16S rRNA gene (e.g., position 432-461 according to the 5'→3' nucleotide sequence). Also, for example, the *E. coli* probe pair (EC SHCP and EC FITC-DP) was designed to be fully complementary to both synthetic EC DNA and the partial region of the *E. coli* 16S rRNA targets. The universal probe pair (UNI SHCP and UNI FITC-DP) can detect, for example, *Citrobacter freundii, Enterobacter aerogenes, Escherichia coli, E. faecium, E. cloacae, Enterococcus faecalis, Proteus mirabilis, Klebsiella oxytoca, Klebsiella pneumoniae, Pseudomonas aeruginosa, Morganella morganii, Staphylococcus aureus,* and *S. saprophyticus*.

TABLE 1

| Oligonucleotide | SEQ ID NO | Sequence (5'→3') |
|---|---|---|
| Thiolated Capture Probes (SHCP) | | |
| EC SHCP | 1 | Thiol-TAT TAA CTT TAC TCC |
| UNI SHCP | 2 | Thiol-GTT CCC CTA CGG TTA CCT T |
| Detector Probes (DP) | | |
| EC FITC-DP | 3 | CTT CCT CCC CGC TGA-FITC |
| UNI FITC-DP | 4 | GTT ACG ACT TCA CCC CAG-FITC |
| Complementary target EC DNA | 5 | TCA GCG GGG AGG AAG GGA GTA AAG TTA ATA |
| Non-complementary target EC | 6 | CTG GGG TGA AGT CGT AAC AAG GTA ACC GTA |
| 2-Base mismatched EC | 7 | TCA GCG GGG AGG AAG GGA GT<u>C</u> AAG T<u>GA</u> ATA |
| 3-Base mismatched EC | 8 | TCA <u>A</u>CG <u>A</u>GG AG<u>C</u> AAG GGA GTA AAG TTA ATA |

Bacterial strains of *E. coli* NEB 5-α (New England Biolabs) and clinical isolate *Klebsiella pneumoniae* (KP210) used in the exemplary implementations were obtained from the Clinical Microbiology Laboratory, University of California-Los Angeles (UCLA), with approval from the UCLA and Veterans Affairs institutional review boards and appropriate Health Insurance Portability and Accountability Act exemptions. The isolates were received in centrifuge tubes and were stored at −80° C. until use. Overnight bacterial cultures were freshly inoculated into Luria broth (LB) and grown to logarithmic phase as measured by the optical density at 600 nm. Concentrations in the logarithmic-phase specimens were determined by serial plating.

Buffer solutions used in the exemplary implementations included a DNA immobilization buffer (IB), e.g., which contained 10 mM Tris-HCl, 1 mM ethylenediaminetetraacetic acid, and 0.3 M NaCl (pH 8.0); a hybridization buffer (HB), e.g., which was a 1 M phosphate buffer solution containing 2.5% bovine serum albumin (pH 7.2); and a binding buffer (BB), e.g., for association with anti-FITC-HRP was 1×PBS (pH 7.2) containing 0.5% casein.

Amperometric measurements performed in the exemplary implementations used, for example, a PalmSens hand-held potentiostat equipped with an eight-channel PalmSens Multiplexer (CH8) (Palm Instruments BV, Electrochemical Sensor Interfaces, Houten, The Netherlands). Exemplary 16-sensor Au electrode arrays used in the exemplary nucleic acid hybridization implementations were acquired from GeneFluidics Inc. (Monterey Park, Calif.). For example, each sensor included a central Au working electrode (e.g., 2.5 mm diameter) surrounded by a quasi Au reference electrode and an Au auxiliary electrode. An electrochemical analyzer was used in the exemplary implementations for the EIS and CV experiments, e.g., the CHI 660D electrochemical analyzer (CH Instruments, Austin, Tex.). For example, the exemplary CHI 660D electrochemical analyzer was connected to a Au disk working electrode (e.g., AuE, ∅=2 mm), a Ag/AgCl reference electrode, and a Pt wire auxiliary electrode. Pretreatment to the electrode was applied to clean the AuE.

Preparation of the capture-probe-modified gold surface performed in the exemplary implementations is described. For example, appropriate concentrations of the EC SHCP in IB, e.g., with and without 200 µM freshly prepared DTT (also in IB buffer), were prepared and allowed to stand for 10 min. Aliquots (6 µL) of this EC SHCP/DTT solution were drop cast to cover each Au working electrode in the 16-sensor Au array and were incubated overnight at 4° C. in humidified surroundings. The EC SHCP/DTT SAM-modified Au sensors were washed with water and dried with nitrogen. The EC SHCP/DTT SAM-modified Au sensors were subsequently treated with 6 µL of 1 mM MCH, OEG, or MPA aqueous solution (in IB buffer) for 50 min, e.g., to obtain different mixed SAMs. The sensors were thoroughly rinsed with water and dried under nitrogen.

EIS and CV measurements performed in the exemplary implementations are described. For example, faradic impedimetric and CV measurements were carried out in a 0.1 M KCl solution containing the $[Fe(CN)_6]^{3-/4-}$ redox probe (5 mM concentration of each component). Impedance spectra were obtained over the frequency range of 0.01-10000 Hz at +0.25 V (vs. Ag/AgCl). The amplitude of the alternating voltage was 0.01 V. Exemplary experimental spectra was presented in the form of complex plane diagrams (e.g., Nyquist plots), e.g., which were analyzed by nonlinear least-squares (NLLS) using the EQUIVCTR.PAS (EQU) program. The impedance (Z) was expressed in terms of a real component (Z') and an imaginary (Z") component.

An exemplary experimental implementation procedure of DNA hybridization assays is described. In one example, a DNA detection protocol involved a sandwich-type hybridization assay and the capture of the HRP enzyme tag. For example, different concentrations of the exemplary target EC DNA were mixed with the EC FITC-DP (0.25 µM) in the HB. Aliquots (4 µL) of this target EC DNA/EC FITC-DP hybrid solution were cast onto each of the SAM-modified gold sensors and were incubated for 15 min. After the array was washed and dried, 4 µL of a 0.5 U mL$^{-1}$ anti-FITC-HRP solution (prepared in BB) was cast onto each of the working electrodes for 15 min. Subsequently, the array was washed and dried. An exemplary prefabricated plastic 16-well manifold (GeneFluidics) was bonded to the sensor array. The sensor array was connected to the exemplary eight-channel PalmSens Multiplexer, and 50 µL of the TMB-$H_2O_2$ K-Blue reagent solution was placed sequentially on each of the sensors in the array, e.g., covering the three-electrode area. Chronoamperometric detection was performed sequentially for all 16 sensors after each TMB-$H_2O_2$ drop was placed on the corresponding sensor. For example, the potential was stepped to −200 mV (vs. the quasi Au reference electrode), and the current was sampled at 60 s.

An exemplary experimental implementation procedure of bacterial 16S rRNA hybridization assays is described. For example, the bacteria were lysed by resuspension of the appropriate pellet containing ~$10^7$ CFU bacteria in 10 µL of 1 M NaOH and incubation for 5 min. A 50 µL aliquot of EC FITC-DP (0.25 µM) in HB was added to this 10 µL bacterial lysate, leading to genetic material corresponding to ~$10^7$ CFU per 60 µL. This solution was serially diluted in the EC FITC-DP (0.25 µM), e.g., to provide different concentrations of bacterial genetic material (16S rRNA). Aliquots (4 µL) of this raw bacterial lysate target solution were cast onto each capture-probe-modified sensor and incubated for 15 min, which was followed by the same capture of anti-FITC-HRP and the electrochemical detection steps described earlier for the synthetic target EC DNA. The exemplary experimental procedures were carried out at room temperature.

Figure 2A:
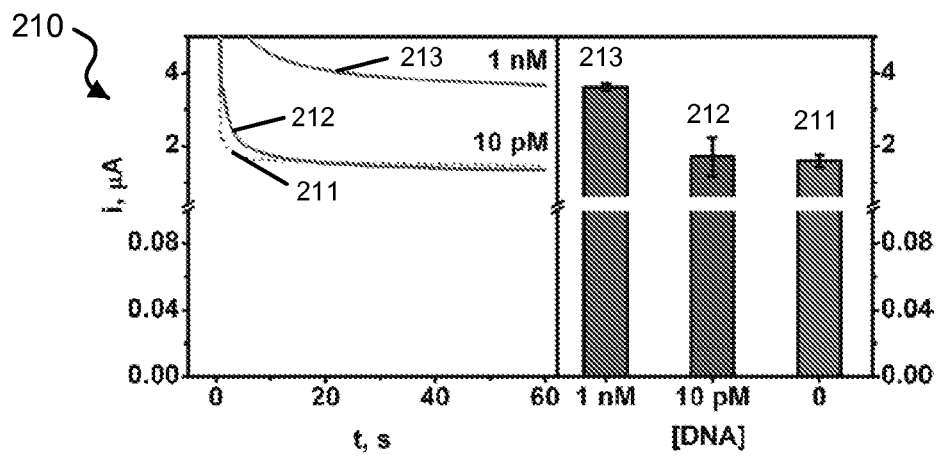
FIGS. 2A and 2B show data plots comparing detectable signal strength of an exemplary ternary SAM interface of the disclosed technology and a binary SAM interface.
Figure 2B:
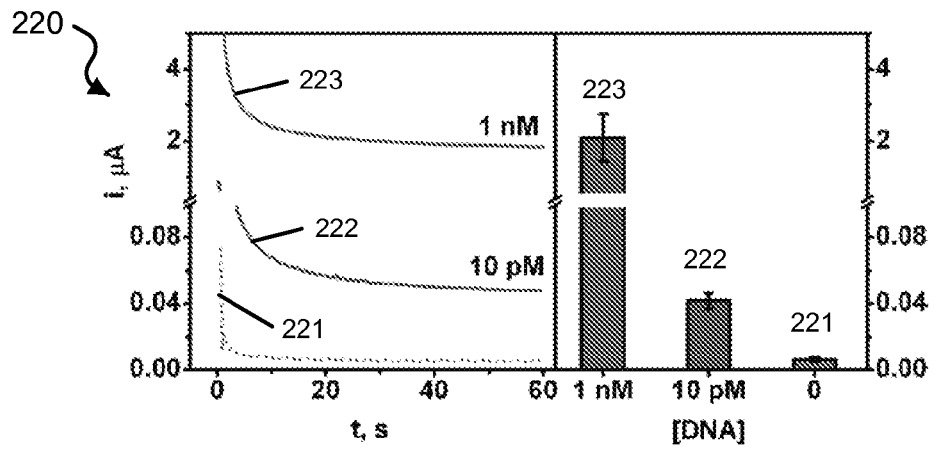

Exemplary experimental data is described that demonstrates the disclosed ternary monolayer interfaces implemented in electrochemical DNA hybridization biosensing applications. FIGS. 2A-2B show exemplary data plots comparing hybridization discrimination effects at two different concentrations of target EC DNA on exemplary surfaces employing the ternary SAM interface of the disclosed technology and exemplary surfaces having a binary SAM interface. FIG. 2A shows a data plot 210 that displays data (in µA) for surfaces modified with a binary SAM configuration (e.g., serving as a control) that includes EC SHCP+MCH surfaces. For example, data (dotted) line and data bar 211 in the plot 210 represent the nonspecific background contribution of the EC SHCP+MCH binary surfaces in the absence of target EC DNA. Also shown in the plot 210 are exemplary DNA hybridization chronoamperometric responses that were determined for target EC DNA concentrations of 10 pM (shown as data line and data bar 212) and 1 nM (shown as data line and data bar 213) using the EC SHCP+MCH binary interface. As shown in FIG. 2A, the measured signal of the nonspecific background contribution and the 10 pM concentration of target EC DNA was substantially the same. This can imply that the signal-to-noise strength of a binary SAM interface is not sufficient to detect a target analyte such concentrations.

FIG. 2B shows a data plot 220 that displays data (in µA) for surfaces modified with a ternary SAM configuration (e.g., ternary SAM interface 100) that includes EC SHCP/DTT+MCH surfaces. For example, data (dotted) line and data bar 221 in plot 220 represent the nonspecific background contribution of the EC SHCP/DTT+MCH ternary surfaces in the absence of target EC DNA. Also shown in the plot 220 are exemplary DNA hybridization chronoamperometric responses that were determined for target EC DNA concentrations of 10 pM (shown as data line and data bar 222) and 1 nM (shown as data line and data bar 223) using the EC SHCP/DTT+MCH ternary interface. As shown in FIG. 2B, the exemplary ternary SAM surfaces produced a substantially lower nonspecific background contribution (dotted line and data bar 221) than the detected signals of 10 pM and 1 nM target EC DNA (data line and data bar 222 and data line and data bar 223, respectively). This resulted in a substantially higher signal-to-noise ratio (S/N) of the disclosed ternary SAM interface compared to the binary SAM interface. For example, a 260-fold decrease in the background current (e.g., 6 nA vs. 1569 nA) was observed at the exemplary ternary SAM interface. Also for example, the ternary monolayer surface was shown to exhibit a substantially 100-fold improved in the S/N characteristics. For example, the exemplary ternary layer interface was capable to detect target DNA at a 10 pM concentration; the exemplary binary layer interface was not capable to detect target DNA at a picomolar level. The ternary interfaces of the disclosed technology can increase S/N characteristic of biosensor devices.

Examples are described for various structures and platforms implementing ternary SAM interfaces, e.g., an EC SHCP/DTT+MCH platform for sequence-specific nucleic acid detection. For example, ultrasensitive DNA hybridization assays and biosensors are described with femtomolar and zeptomole detection limits. In some examples, different interfaces are described using a dithiol-based ternary SAM assembly platform, e.g., a biosensor. In some examples, different binary and ternary SAM interfaces are implemented to comparatively show the influence of different backfillers (e.g., MCH, MPA, DTT, and OEG) on the hybridization efficiency and minimization of the background noise, and hence the overall S/N characteristics of corresponding DNA electrochemical sensors. For example, highly sensitive genosensors can be designed and implemented based on the disclosed ternary SAM interface, e.g., the SHCP/DTT+MCH interface.

Various exemplary binary and multi-component ternary SAM interfaces prepared with the different backfillers are described and shown in exemplary experimental implementations. Table 2 displays the signal-to-noise characteristics of exemplary monocomponent, binary, ternary, and quaternary SAM interfaces for hybridization assays using 1 nM target EC DNA, e.g., using the exemplary HRP/TMB system. As shown in the table, the hybridization efficiency on a pure EC SHCP layer is low, e.g., indicated from its signal, among the lowest of the exemplary interfaces. The introduction of a "dilution" molecule to a surface having a DNA oligonucleotide probe can be included on a modified surface to improve DNA hybridization with a complimentary DNA target. For example, a dilution molecule, e.g., MCH, can be used to assist a monocomponent DNA oligonucleotide probe to stand up and repel nonspecific adsorption, e.g., nonspecific adsorption of the HRP tag on the surface by the negative OH headgroups of the dilution molecule. In Table 2, A/B chemical schemes refers to simultaneous co-immobilization of A and B, and A+B chemical schemes refers to sequential immobilization of A and B. Thus, the exemplary multi-component interfaces shown in Table 2 also demonstrate the effects of using one-step co-assembly and two-step sequential assembly processes on the S/N characteristics.

TABLE 2

| SAM Interface | Monolayer Composition | S | N | S/N |
|---|---|---|---|---|
| Mono-component | SHCP | 203.6 | 110.2 | 1.8 |
| Binary | SHCP + MCH | 3600.1 | 1569 | 2.3 |
| | SHCP + OEG | 151 | 3.4 | 44.4 |
| | SHCP + MPA | 1487.8 | 27.3 | 54.4 |
| | SHCP/MCH | 1043 | 549 | 1.9 |
| | SHCP/DTT | 2904 | 52.8 | 55.0 |
| Ternary | SHCP/DTT + MCH | 1963.2 | 6.0 | 327.2 |
| | SHCP/DTT + OEG | 2355.4 | 5.6 | 420.6 |
| | SHCP/DTT + MPA | 1466.6 | 8.3 | 176.7 |
| | SHCP/DTT + MCH | 1514.7 | 10.6 | 142.9 |
| | SHCP + DTT + MCH | 1452.4 | 8.4 | 172.9 |
| | SHCP + MPA + MCH | 531.8 | 6.8 | 78.2 |
| Quaternary | SHCP/DTT + MPA + MCH | 2270 | 6.4 | 354.7 |

As shown in Table 2, fabrication of ternary and quaternary SAM interfaces using a dithiol (e.g., DTT) backfiller substantially improved S/N characteristics. For example, the ternary EC SHCP/DTT+MCH surface exhibited an S/N of 327 for 1 nM target EC DNA, which was shown ~140 and 6-fold higher than the S/N of binary surfaces such as EC SHCP+MCH and EC SHCP/DTT surfaces, respectively. For example, the ternary EC SHCP/DTT+OEG surface provided an S/N of 421 for 1 nM DNA, which was shown to be ~10 times higher than the binary EC SHCP+OEG and EC SHCP/DTT surfaces. The DTT-based ternary SAM interfaces can exhibit large S/N characteristics attributed to the coupling of cyclic- and linear-configuration backfillers. For example, the cyclic- and linear-configuration backfillers can overcome the incomplete backfilling and related surface defects that exist with binary SAM interfaces. Self-assembled monolayers configured in the ternary SAM interfaces of the disclosed technology can form compact and complete surface coverage on the substrates.

As shown in Table 2, a quaternary SAM interface (e.g., EC SHCP/DTT+MPA+MCH interface) exhibited an S/N of 355 for 1 nM target EC DNA, which was substantially similar to the 327 S/N value exhibited by the corresponding ternary SAM (EC SHCP/DTT+MCH) layer. This exemplary result can indicate that the additional quaternary MPA backfiller offered limited, if any, improvement to S/N characteristics produced by ternary SAM interfaces. The fabrication techniques to produce the disclosed ternary SAM interfaces also can affect the surface performance, e.g., in biosensor devices employing the ternary SAM interfaces of the disclosed technology. For example, SHCP, DTT, and MCH were assembled sequentially to form the EC SHCP+DTT+MCH sequentially-assembled ternary surface, which exhibited an S/N of 173 for 1 nM target EC DNA (shown in Table 2). This exemplary S/N value is nearly half of the S/N value (e.g., 327) exhibited by the EC SHCP/DTT+MCH co-assembled ternary surface. These exemplary results can indicate that co-immobilization fabrication techniques of ternary SAM interfaces can lead to greater performance than sequential assembly techniques.

For example, differential discrimination effects for the exemplary interfaces may be related to the nature of the diluent interactions (e.g., hydrophobic and/or hydrophilic) along with differences in the EC SHCP coverage while forming either compact or defective mixed monolayers, as well as to the different chain lengths and head-group functionalities. For example, a dithiol co-immobilized with an SHCP and a short chain thiol can form highly compact ternary SAM interfaces with minimal pinhole defects and assemblies of the capture probe with sufficient spacing for optimal hybridization. For example, a dithiol (e.g., DTT) can chemisorb onto a gold surface via two Au—S bonds (with no free thiol), e.g., with the two hydroxyl groups of DTT exposed at the outer surface. This orientation, illustratively shown in the schematic of FIG. 1, can provide a hydrophilic microenvironment favorable for hybridization, which can also enhance the nonfouling properties of the monolayer interface.

Figure 3:
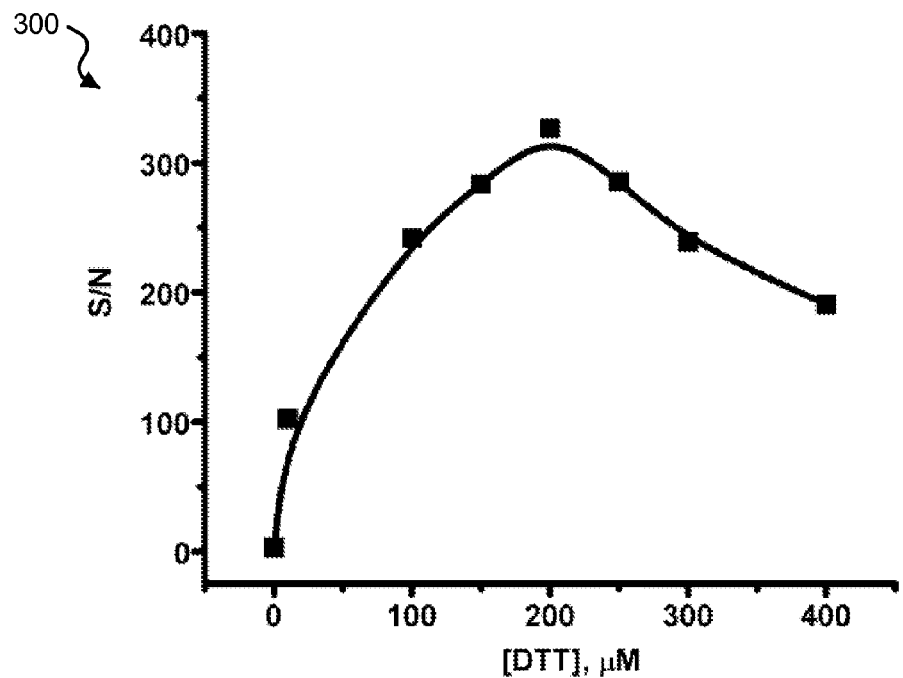
FIG. 3 shows a data plot of the effect of dithiol concentration on the signal-to-noise ratio of an exemplary ternary SAM interface.

FIG. 3 shows a data plot 300 that shows the concentration effects of the exemplary dithiol DTT on the S/N characteristics of the ternary SAM interface EC SHCP/DTT+MCH to detect a 1 nM target EC DNA (e.g., using 0.05 µM EC SHCP and 1 mM MCH). In this exemplary experimental implementation, EC SHCPs were assembled onto a surface by a co-immobilization step with DTT, which can lead to competition between the EC SHCP and DTT for the exposed gold surface. Thus, both the surface coverage and the spacing of the EC SHCP may be dependent on this competition. As indicated in plot 300, increasing the concentration of DTT resulted in a greater S/N ratio. For example, an increase in the DTT concentration can result in more DTT molecules assemble on the surface, thereby efficiently increasing the surface compactness and improving the probe spacing and resistance to nonspecific adsorption, resulting in a greatly improved signal-to-noise ratio. The plot 300 also indicated that increasing the DTT concentration above 200 µM in this example (e.g., 0.05 µM EC SHCP, 1 mM MCH) may lead to gradually reduced performance, e.g., as DTT may begin to dominate the surface and reduce EC SHCP surface coverage.

Figure 4A:
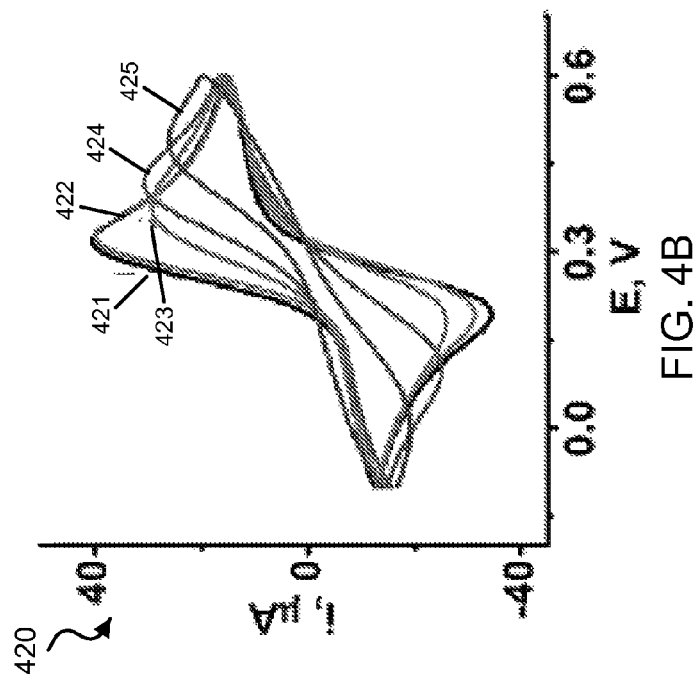
FIGS. 4A and 4B show data plots of exemplary electrochemical impedance spectroscopy and cyclic voltammogram data.
Figure 4B:
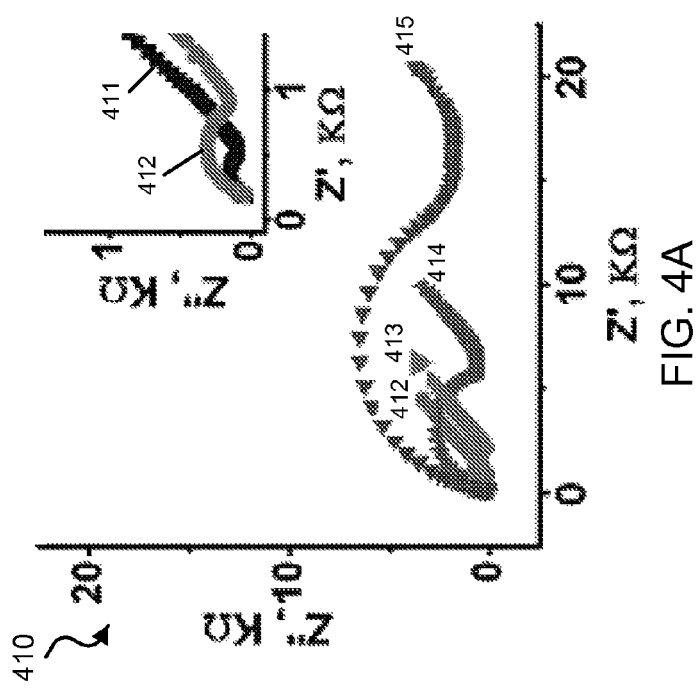

Exemplary electrochemical characterizations of the DTT-based ternary SAM interfaces were performed using electrochemical impedance spectroscopy (EIS) and cyclic voltammetric (CV) characterization techniques. The implementation of EIS and CV techniques can provide insights into the SAM coverage and compactness on the surface, e.g., the ternary monolayer interface in comparison to a binary SAM interface. FIG. 4A shows a Nyquist plot 410 that features exemplary EIS data (e.g., 411, 412, 413, 414, and 415) for monocomponent, binary, and ternary SAM interfaces obtained in the presence of equimolar [Fe(CN)$_6$]$^{4-/3-}$. The data 411 represents exemplary EIS data acquired for bare AuE electrodes. The data 412 represents exemplary EIS data acquired for monocomponent SAM-modified Au electrodes (e.g., EC SHCP). The data 413 represents exemplary EIS data acquired for binary SAM-modified Au electrodes (EC SHCP+MCH), and the data 414 represents exemplary EIS data acquired for binary SAM-modified Au electrodes (EC SHCP/DTT). The data 415 represents exemplary EIS data acquired for ternary SAM-modified Au electrodes (EC SHCP/DTT+MCH). FIG. 4B shows a Nyquist plot 420 that features exemplary CV data (e.g., 421, 422, 423, 424, and 425) for monocomponent, binary, and ternary SAM interfaces obtained in the presence of equimolar [Fe(CN)$_6$]$^{4-/3-}$. The data 421 represents exemplary CV data acquired for bare AuE electrodes. The data 422 represents exemplary CV data acquired for monocomponent SAM-modified Au electrodes (e.g., EC SHCP). The data 423 represents exemplary CV data acquired for binary SAM-modified Au electrodes (EC SHCP+MCH), and the data 424 represents exemplary CV data acquired for binary SAM-modified Au electrodes (EC SHCP/DTT). The data 425 represents exemplary CV data acquired for ternary SAM-modified Au electrodes (EC SHCP/DTT+MCH). Operating conditions of the exemplary EIS implementations include: 5 mM [Fe(CN)$_6$]$^{4-/3-}$ (1:1) in 0.1 M KCl, 0.01-10000 Hz frequency range with a 0.01 V$_{rms}$ signal at +0.25 V (vs. Ag/AgCl). Operating conditions of the exemplary CV implementations include v=100 mV s$^{-1}$. As indicated by the exemplary data in FIG. 4A, the bare AuE displayed fast electron transfer process with a diffusional limiting step. Increased electron transfer resistance occurred for electrodes coated with the different monolayers.

Figure 4C:
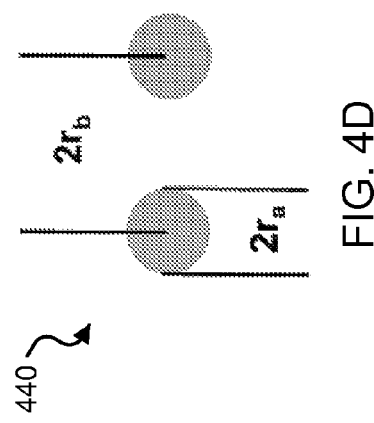
FIG. 4C shows an exemplary Randles modified equivalent circuit schematic to fit the exemplary EIS data.

FIG. 4C shows a Randles modified equivalent circuit schematic 430 that was used to fit the exemplary EIS data (e.g., 411, 412, 413, 414, and 415) and to determine electrical parameters of the monolayers. Table 3 shows a summary of exemplary EIS data extracted and calculated from exemplary experimental data modeling using the Randles equivalent circuit (e.g., EC SHCP). For example, Table 3 summarizes values calculated for electrolyte resistance (R$_S$), Warburg impedance resulting from ion diffusion from the electrolyte bulk (Z$_W$), electron transfer resistance (R$_{et}$), and constant phase element Q (instead of the double layer capacitance, C$_{dl}$, to account for the fact that the frequency dispersion is often related directly to the electrode roughness). The exemplary Nyquist plot 410 illustrates the increased electron transfer resistance value upon changing from a naked surface (e.g., data 411) to the various binary SAMs (e.g., data 413 and 414) and ternary SAMs (e.g., data 415). For example, Table 3 shows that an R$_{et}$ value of 366.9Ω of bare AuE electrodes increased to an R$_{et}$ value of 14698.1Ω of the ternary SAM interface SHCP/DTT+MCH. For example, the change in the R$_{et}$ value can reflect the greatly increased surface coverage values associated with the binary and ternary layers. Also for example, electrodes modified with different monolayers exhibited a decreased cyclic voltammetric peak current and an increased peak potential separation compared to the voltammetric behavior observed at the bare electrode (as shown in FIG. 4B). The exemplary voltammetric data (e.g., "blocking" behavior) were shown to be consistent with the exemplary data of the EIS experiments.

TABLE 3

| Surface | Q (µF) | Z$_W$ (Ω · s$^{-1/2}$) | R$_{et}$ (Ω) | R$_S$ (Ω) | θ$_{IS}^R$ | θ$_{IS}^P$ | r$_a$ (µm) | r$_b$ (µm) |
|---|---|---|---|---|---|---|---|---|
| Bare | 2.12 | 7.81 × 10$^{-4}$ | 366.9 | 166.4 | | | | |
| SHCP | 1.93 | 8.17 × 10$^{-4}$ | 751.4 | 175.9 | 0.5117 | | | |
| SHCP + MCH | 0.268 | 6.67 × 10$^{-4}$ | 5877.3 | 171.0 | 0.9376 | 0.9847 | 1.1 | 8.7 |
| SHCP/DTT | 0.849 | 5.90 × 10$^{-4}$ | 1866.6 | 187.8 | 0.8034 | | | |
| SHCP/DTT + MCH | 0.466 | 4.64 × 10$^{-4}$ | 14698.1 | 186.4 | 0.9750 | 0.9895 | 2.3 | 22.6 |

For example, the charge transfer resistance (R$_{et}$) can be related to the coverage of the electrode (θ$_{IS}^R$), as described in Equation (1), e.g., which can assume that electron transfer reactions occur only at bare surface spots and that the diffusion to these defect sites is planar:

$$\theta_{IS}^R = 1 - \left(\frac{R_{et}^{AuE}}{R_{et}^{SAM}}\right) \quad (1)$$

where R$_{et}^{AuE}$ and R$_{et}^{SAM}$ are the charge transfer resistances measured at the bare and monolayer-covered electrodes, respectively. When the (θ$_{IS}^R$) value approaches 1 (θ>0.9), the coverage can be estimated using a model based on the pinhole size, e.g., described in Equation (2):

$$\theta_{IS}^P = 1 - \left(\frac{\sigma_W}{m - \sigma_W}\right) \quad (2)$$

where σ$_W$ is the Warburg coefficient (calculated from the characterization of the bare AuE) and m is the slope of the linear interval observed in the high-frequency region of the Z' vs. ω$^{-1/2}$ function obtained at the SAM-modified electrode.

As shown in Table 3, the exemplary θ$_{IS}^P$ values of EC SHCP/DTT, EC SHCP+MCH, and EC SHCP/DTT+MCH were determined to be 0.8034, 0.9847, and 0.9895, respectively. These exemplary data can indicate that the surface coverage follows the order EC SHCP/DTT+MCH EC SHCP+MCH>EC SHCP/DTT. For example, the co-assembly of the dithiol DTT molecule, e.g., via two Au—S bonds, can lead to a ternary monolayer with a high packing density and surface coverage. For example, the exemplary EC SHCP/DTT interface can demonstrate superior performance characteristics compared to a common SAM interface prepared with a linear-configuration backfiller, e.g., EC SHCP+MCH. In addition, for example, the surface coverage of the exemplary interface EC SHCP/DTT can be increased by complementary backfilling with a linear-configuration backfiller (e.g., MCH). As a result, a high surface coverage (e.g., $\theta_{IS}^p$ of 0.9895) can be achieved for the ternary EC SHCP/DTT+MCH SAM interface.

Figure 4D:
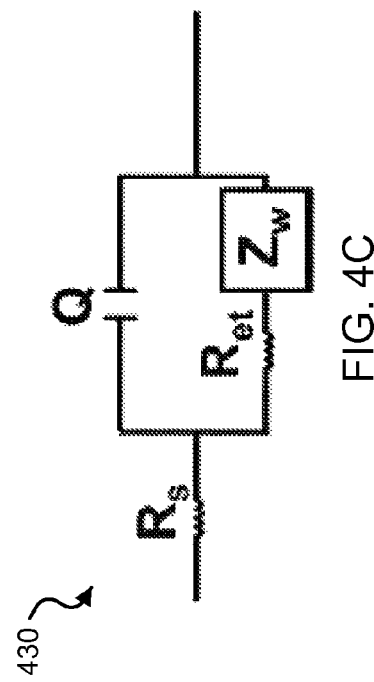
FIG. 4D shows an exemplary model illustrating pinhole radii and spacing.

Moreover, the fraction of the pinhole area $(1-\theta_{IS}^p)$ can be related to the size of the pinholes $(r_a)$ and the distance between the centers of adjacent pinholes $(r_b)$. FIG. 4D shows a pinhole model 440 that includes illustrates a pinhole radius $r_a$ and a pinhole separation length $r_b$, which is half the distance between the centers of adjacent pinholes. The relationship between the surface coverage area and pinhole radius and area are described in Equation (3):

$$1 - \theta_{IS}^p = \frac{r_a^2}{r_b^2} \quad (3)$$

As shown in Table 3, the exemplary $r_a$ and $r_b$ values for binary EC SHCP+MCH and ternary EC SHCP/DTT+MCH interfaces were determined to be ca. 0.1-10 and 1-100 μm, respectively for the pinhole radii and separation, e.g., which can be consistent with microelectrode array behavior of gold electrodes modified with these SAMs. For example, compared to the binary EC SHCP+MCH surface, the ternary EC SHCP/DTT+MCH surface exhibited greater $r_b$ values, which can indicate substantially fewer pinholes on the ternary SAM. As was discussed earlier, the reduced amount of pinholes can reflect a compact and nearly complete surface coverage, e.g., offered by the ternary SAM interface. For example, the exemplary EIS data indicate that the ternary EC SHCP/DTT+MCH interface scheme can offer the following advantages compared with a binary EC SHCP+MCH SAM interface. First, for example, the larger EIS capacitance value of the DTT-based ternary surface indicates that the inclusion of this short spacer provides a compact self-assembled monolayer with high electron permeability and very good overall surface coverage, making the system suitable for electrochemical sensing. Also, for example, the high $\theta_{IS}^p$ value of the ternary SAM interface (e.g., its high surface coverage) leads to a greater resistance to surface fouling. Additionally, for example, the higher $r_b$ value indicates that the ternary SAM interface possesses fewer pinholes, which can produce optimal spacing of the capture probe, thereby providing freedom for the target coiling.

Figures 5A, 5B:
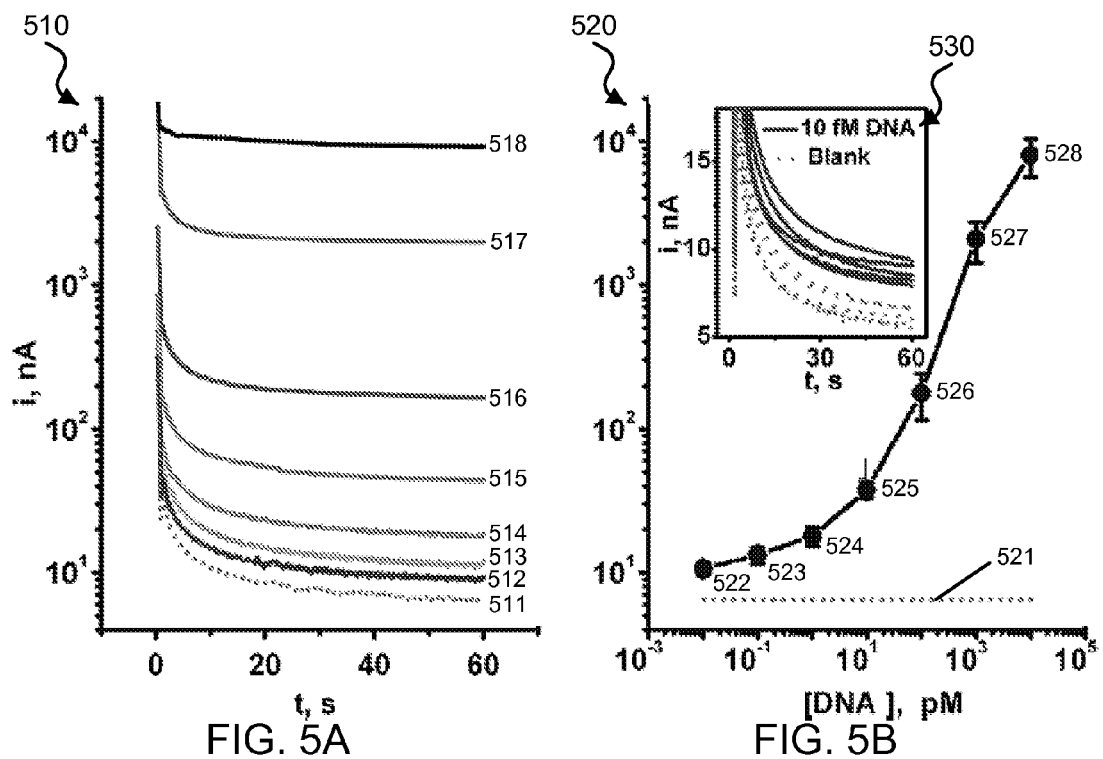
FIGS. 5A and 5B show data plots exhibiting exemplary chronoamperometric responses for different concentrations of E. coli target DNA.

Exemplary implementations were performed to demonstrate electrochemical detection of DNA hybridization using the exemplary ternary SAM interfaces. Exemplary biosensor chips were modified with a ternary EC SHCP/DTT+MCH monolayer at various concentrations. For example, the analytical performance of the DNA hybridization assay based on the optimal EC SHCP/DTT+MCH interface was characterized using microliter (4 μL) samples. For example, the potential was stepped to −0.2 V. FIG. 5A shows a data plot 510 exhibiting exemplary chronoamperometric responses of data 511, 512, 513, 514, 515, 516, 517, and 518 for different concentrations of the target EC DNA over a time course. Data line 511 (shown as a dotted red line) corresponds to 0 M of the target EC DNA. Data line 512 corresponds to 10 fM of the target EC DNA. Data line 513 corresponds to 100 fM of the target EC DNA. Data line 514 corresponds to 1 pM of the target EC DNA. Data line 515 corresponds to 10 pM of the target EC DNA. Data line 516 corresponds to 100 pM of the target EC DNA. Data line 517 corresponds to 1 nM of the target EC DNA. Data line 518 corresponds to 10 nM of the target EC DNA.

FIG. 5B shows an exemplary calibration plot 520 on a logarithmic scale exhibiting exemplary current data vs. target EC DNA concentration data. For example, the plot 520 indicates a nonlinear logarithmic dependence between the amperometric signal and the target EC DNA concentration over such a wide (nanomolar to femtomolar) range. Data point 521 (shown as a dotted red line) corresponds to 0 M of the target EC DNA. Data point 522 corresponds to 10 fM of the target EC DNA. Data point 523 corresponds to 100 fM of the target EC DNA. Data point 524 corresponds to 1 pM of the target EC DNA. Data point 525 corresponds to 10 pM of the target EC DNA. Data point 526 corresponds to 100 pM of the target EC DNA. Data point 527 corresponds to 1 nM of the target EC DNA. Data point 528 corresponds to 10 nM of the target EC DNA.

For example, the lowest detectable concentration, 10 fM, was shown to correspond to 40 zeptomoles in the 4 μL sample. The inset within FIG. 5B shows a data plot 530 exhibiting exemplary data of five chronoamperometric signals for 10 fM target EC DNA (blue solid lines) along with the corresponding blank (no target EC DNA) signals (red dotted lines). For example, differences between the exemplary samples containing the 10 fM target EC DNA and the negative control (without target EC DNA) were shown to be statistically significant ($P<0.05$). The five exemplary repetitive runs for the background and 10 fM target EC DNA solutions (plot 530 of FIG. 5B inset) can indicate that the disclosed DNA hybridization biosensors employing ternary SAM interfaces can detect ultra-low (e.g., femtomolar and lower) target concentrations. Additionally, for example, ternary SAM interfaces can enhance the overall reproducibility of signal detection, e.g., of DNA hybridization biosensors.

Figure 6:
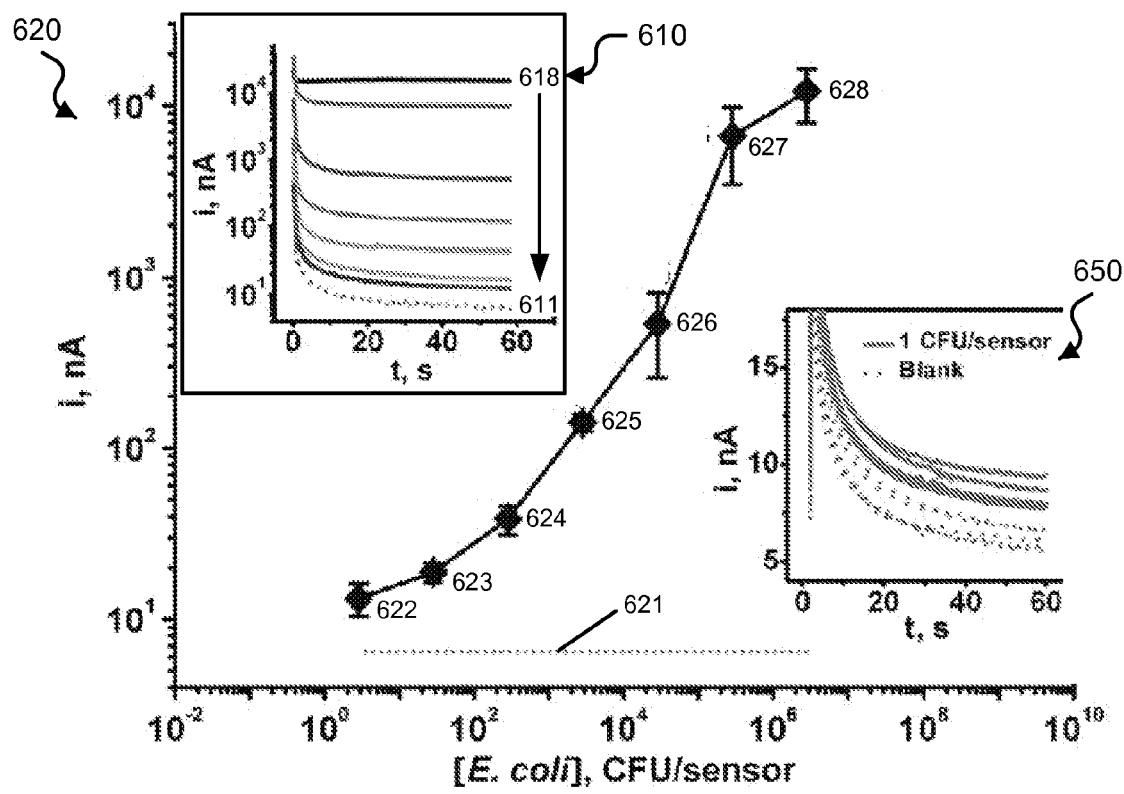
FIG. 6 shows data plots displaying exemplary chronoamperometric signals for various bacterial lysate solutions corresponding to E. coli concentrations.

Exemplary genosensor devices are described, e.g., the utility of exemplary nucleic acid hybridization assay biosensor employing the ternary surface interface for the detection of *E. coli* pathogenic 16S rRNA is illustrated. For example, biosensor chips were modified with the EC SHCP/DTT+MCH monolayer. FIG. 6 shows a logarithmic calibration plot 620 of *E. coli* 16S rRNA corresponding to different pathogen bacterial concentrations. The data shown in the plot 620 includes: data line 621 corresponding to 0 CFU/sensor (dotted red line), data point 622 corresponding to 3 CFU/sensor, data point 623 corresponding to 30 CFU/sensor, data point 624 corresponding to 300 CFU/sensor, data point 625 corresponding to $3 \times 10^3$ CFU/sensor, data point 626 corresponding to $3 \times 10^4$ CFU/sensor, data point 627 corresponding to $3 \times 10^5$ CFU/sensor, and data point 628 corresponding to $3 \times 10^6$ CFU/sensor.

The left inset of FIG. 6 shows a chronoamperogram data plot 610 displaying exemplary chronoamperometric signals obtained for different bacterial lysate solutions corresponding to *E. coli* cell concentrations. The data shown in the plot 610 includes: data line 611 corresponding to 0 CFU/sensor (dotted red line), data line 612 corresponding to 3 CFU/sensor, data line 613 corresponding to 30 CFU/sensor, data line 614 corresponding to 300 CFU/sensor, data line 615 corresponding to $3 \times 10^3$ CFU/sensor, data line 616 corresponding to $3 \times 10^4$ CFU/sensor, data line 617 corresponding to $3 \times 10^5$ CFU/sensor, and data line 618 corresponding to $3 \times 10^6$ CFU/sensor.

The right inset of FIG. 6 shows a chronoamperogram data plot 650 displaying exemplary chronoamperometric response for 16S rRNA of 1 CFU per sensor (shown as the green solid data lines) and for the corresponding blank (0 CFU) signals (shown as the red dotted lines). For example, a series of five exemplary measurements of 16S rRNA corresponding to 1 CFU per sensor were carried out along with five control experiments (e.g., blank signals).

The resulting calibration plot 620 indicated a nonlinear logarithmic dependence between the current signal and the level of *E. coli* 16S rRNA down to 3 CFU per sensor. Differences between samples containing 1 CFU of *E. coli* per 4 µL and the negative control (without target nucleic acid) were significant (P<0.05). The resulting chronoamperogram data plot 650 indicated that repetitive signals obtained for the exemplary 1 CFU per 4 µL samples can be distinguished from those observed without the bacterial rRNA target. Considering the 4 µL sample volume, a detection limit can correspond to 250 CFU mL$^{-1}$. Taking into account that *E. coli* contains approximately 2×10$^4$ copies of 16S rRNA per cell, the exemplary detection limit of 250 CFU mL$^{-1}$ can be translated to the detection of 8 fM ribosome copies. This exemplary result is consistent with the exemplary 10 fM detection limit shown in FIGS. 5A and 5B for the target EC DNA.

Exemplary implementations of exemplary ternary SAM biosensors are described that demonstrate precision, specificity, and validation of the disclosed technology. For example, the precision of the disclosed biodetection platform was examined in connection to ultra-low target concentrations. Reproducible signals were obtained, e.g., ten parallel measurements of 10 fM target EC DNA (shown in the data plot 530 of FIG. 5B) and five 16S rRNA measurements corresponding to 1 CFU per sensor (shown in the data plot 650 of FIG. 6). The exemplary data can provide relative standard deviations (RSDs) of 9.9% and 10.3%, respectively.

Figure 7:
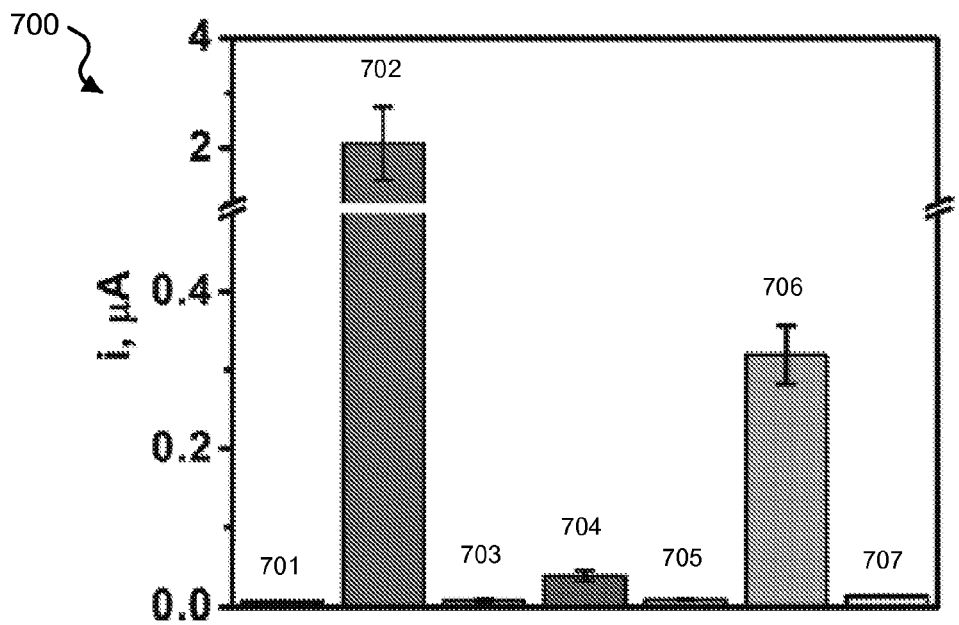
FIG. 7 shows a graph showing the detection specificity of exemplary ternary monolayer-based biosensors.

For example, specificity of the sensing protocol and the disclosed ternary SAM biosensors was examined by challenging the ternary SAM biosensor system with various noncomplementary and mismatched oligonucleotides. For example, exemplary ternary SAM biosensor chips were produced, e.g., EC SHCP/DTT+MCH interface sensors. FIG. 7 shows a column bar graph 700 of chronoamperometric responses obtained for 1 nM sample solutions of noncomplementary and different mismatched oligonucleotides. The exemplary chronoamperometric response data in graph 700 was obtained with 0 nM of the EC target EC DNA (bar 701), 1 nM concentration of the target EC DNA (bar 702), noncomplementary EC DNA (bar 703), two-base-mismatched EC oligonucleotide (bar 704), three-base-mismatched EC oligonucleotide (bar 705), 16S rRNA corresponding to 2.2×10$^4$ CFU of *E. coli* per sensor (bar 706), and 16S rRNA corresponding to 2.9×10$^4$ CFU of *K. pneumoniae* per sensor (bar 707). Exemplary data shown in noncomplementary bar 703 and three-base-mismatched oligonucleotides bar 705 displayed a negligible change in the response, e.g., as compared to the control signal without the nucleic acid (bar 701). Exemplary data of the two-base-mismatched DNA (bar 704) was shown to yield a poorly defined signal of 39 nA. The target EC DNA concentration (bar 702) was shown to yield a strongly defined signal of 2087 nA, e.g., which reflected the partial duplex formation of the double mismatch. The specificity of the disclosed bioaffinity assay technology was also examined using as the no-target biological control *K. pneumoniae*, another Gram-negative pathogenic member of Enterobacteriaceae. As shown in FIG. 7, the response detected in the presence of *K. pneumoniae* 16S rRNA (bar 707) was similar to response detected for the negative control without target nucleic acid (bar 701). The chronoamperometric signal detected for *E. coli* 16S rRNA (bar 706) was shown to be substantial. The data of in graph 700 can indicate that the disclosed ternary interface bioaffinity sensor technology can produce high specificity to target nucleic acids (e.g., EC DNA and *E. coli* 16S rRNA targets). The data of in graph 700 can also indicate that the disclosed ternary interface bioaffinity sensor technology can prevent nonspecific adsorption to the detection probe.

For example, FIG. 8 shows a data graph 800 that includes exemplary experimental data showing the detection limit of exemplary ternary SHCP/DTT+MCH-based biosensor for EC target DNA and *E. coli* rRNA. The exemplary data in the column graph plot corresponding to the chronoamperometric signals were obtained after hybridization with 10 fM of target EC DNA (data bar 801), 1 CFU/sensor (data bar 802) and 0 nM target DNA (data bar 803). The asterix (*) shown in FIG. 8 indicates a significance value of P<0.005.

Exemplary implementations were performed, for example, to evaluate the applicability of the disclosed electrochemical DNA biosensors to biological fluids. For example, ternary EC SHCP/DTT+MCH-based DNA biosensors were implemented in pure HB buffer and in complex biological samples. The exemplary data shown in FIGS. 9A and 9B indicate that the EC SHCP/DTT+MCH interfaces were highly resistant to nonspecific adsorption and exhibited minimal changes in background noise and substantially similar hybridization signal detection capability, e.g., for the 1 nM target EC DNA even in the presence of 25% human serum (FIG. 9A) or human urine (FIG. 9B). Data graph 910 of FIG. 9A shows exemplary data represented by data bars 911 and 912 that were obtained in implementations of ternary EC SHCP/DTT+MCH-based DNA biosensors spiked in pure buffer (HB) and 5%, 10%, and 25% human serum. Data bars 911 represent the detection signal of 1 nM target DNA (blue columns), and data bar 912 represent the corresponding blank (0 M target DNA) signals (red columns). Data graph 920 of FIG. 9B shows exemplary data represented by data bars 921 and 922 that were obtained in implementations of ternary EC SHCP/DTT+MCH-based DNA biosensors spiked in pure buffer (HB) and 5%, 10%, and 25% human urine. Data bars 921 represent the detection signal of 1 nM target DNA (blue columns), and data bar 922 represent the corresponding blank (0 M target DNA) signals (red columns). The exemplary %, 10%, and 25% human serum and human urine samples diluted to different percentages by HB buffer.

Exemplary implementations were performed, for example, to evaluate practicability and specificity of the disclosed bioaffinity platform by using 18 well-characterized uropathogenic isolates. Exemplary implementations produced results that indicated the disclosed sensor array is capable to identify *E. coli* clinical isolates with 100% sensitivity and specificity within 45 min. The exemplary data demonstrates that the disclosed DNA hybridization biosensor system can provide a rapid tool for the identification of clinical isolates. For example, uropathogenic clinical isolates of the uropathogens included: *Escherichia coli* (EC139, EC103, EC71 and EC28), *Klebsiella pneumoniae* (KP295 and KP243), *Pseudomonas aeruginosa* (PA291 and PA98), *Enterobacter aerogenes* (EA368 and EA99), *Proteus mirabilis* (PM291 and PM351), *Serratia marcescens* (SM070 and SM068), *Enterobacter hormaechei* (EH367 and EH151) and *Acinetobacter baumannii* (AB1505 and AB028). It is noted that these exemplary uropathogenic clinical isolates were handled in vials containing brucella broth with 15% glycerol (BBL, Maryland) and were stored at −70° C. For example, overnight bacterial cultures were freshly inoculated into Luria broth (LB) and grown to logarithmic phase as measured by the optical density at 600 nm. Concentrations in the logarithmic-phase specimens were determined by serial plating, typically yielding $10^7$ to $10^8$ bacteria/mL. The uropathogens grown in LB were stored as frozen pellets at −70° C. until the time of experimentation.

The disclosed ternary SAM interface was applied to the determination of these 18 clinical isolates. For these exemplary analytical implementations, both the UNI and EC capture probes (previously defined in Table 1) were tested in duplicates. For example, each clinical isolate pellet was lysed by resuspension in 10 μL of 1 M NaOH and incubation for 5 min. For example, a 500 μL aliquot of both detector probes (EC and UNI FITC-DP, 0.25 μM) in HB was added to the 10 μL bacterial lysate. For example, 40 μL of the resulting 600 μL lysate-probe mixture were cast on each capture-probe modified sensor and incubated for 15 min, followed by the same capture of anti-FITC-HRP and the electrochemical detection steps, described previously.

FIG. 10 shows a column graph 1000 of chronoamperometric signals obtained using the ternary monolayer sensor interface after hybridization with 0 nM target DNA (blank) and each of the 18 clinical isolates. Exemplary biosensor chips were modified to produce with *E. coli* probe pair ternary SAM interfaces (e.g., EC SHCP/DTT+MCH monolayers shown in blue data columns 1001) and universal probe pair ternary SAM interfaces (e.g., UNI SHCP/DTT+MCH monolayers red data columns 1002). As illustrated in graph 1000, the evaluation with the exemplary 18 uropathogenic clinical isolates showed that the EC SHCP/DTT+MCH monolayer platform is highly specific in identifying and discriminating only the *E. coli* isolates (EC139, EC103, EC71 and EC28) from closely related uropathogens. Graph 1000 shows that the UNI SHCP/DTT+MCH platform detected hybridization signals for all 18 clinical isolates.

Only a few exemplary embodiments have been described to show systems, devices, techniques and materials of the disclosed ternary SAM interface, e.g., which can incorporate a thiolated capture probe, MCH, and DTT. The disclosed ternary SAM interface can address challenges associated with incomplete backfilling and related surface defects, e.g., which can be observed in the binary and monocomponent SAM interfaces. The disclosed ternary SAM interface can produce large signal-to-background characteristics, e.g., which can be employed in SAM- and HRP/TMB-based electrochemical DNA biosensors. The disclosed ternary SAM interface can produce biosensor detecting surfaces with substantially lower pinhole defects and significantly higher resistance to nonspecific adsorption, e.g., of nucleic acids, proteins (such as the HRP tag), etc. For example, the disclosed ternary SAM interface can detect signals with negligible background current contributions, e.g., even in the presence of complex biological samples such as serum or urine. For example, the disclosed ternary SAM interface can detect signals with high signal-to-background characteristics, e.g., a zeptomole detection limit. The disclosed technology can be employed in a bioaffinity sensor platform that does not require any deliberate signal or target amplification systems or protocols. Thus, the disclosed technology can be used in a variety of applications, e.g., nucleic acid-based sensor platforms to directly detect raw bacterial rRNA (without additional isolation or purification steps) and directly determine pathogen antibiotic susceptibility directly from clinical samples. The disclosed technology can be used to reduce the consumption of the thiolated probe and be used in applications that require reproducibility.

In another aspect of the disclosed technology, a thiolated capture probe can be co-immobilized with a linear dithiol on a thiol reactive surface, also with subsequent immobilization of a short chain thiol, to form a ternary SAM interface. For example, linear alkanedithiols of different lengths can be utilized, e.g., a propanedithiol (PDT), hexanedithiol (HDT), and nonanedithiol (NDT), to produce ternary SAM interfaces on gold surfaces that produce bioaffinity sensor devices with excellent analytical performance. In some examples using undiluted human serum, an HDT-incorporated ternary SAM interface can provide 50-fold and 5-fold S/N improvements over binary and the DTT-incorporated ternary SAM assemblies, respectively. For example, the HDT-incorporated ternary SAM recognition interface can allow direct quantification of a target EC DNA down to 7 pM (28 amol) in undiluted/untreated serum. The HDT-incorporated ternary SAM interface can also exhibit excellent antifouling properties and high storage stability, e.g., under dry conditions.

Various exemplary implementations are described for a bioaffinity recognition interface based on linear dithiols that can enable direct electrochemical measurements of trace DNA sequences in undiluted samples in a reproducible manner, e.g., human serum and urine samples within 30 min. The disclosed biodetection platform also exhibits excellent antifouling properties and large S/N ratio after prolonged exposure (e.g., a 24 hr exposure) to undiluted biological matrices. The disclosed biodetection platform also exhibits long-term storage stability, e.g., under dry conditions.

Figure 11A:
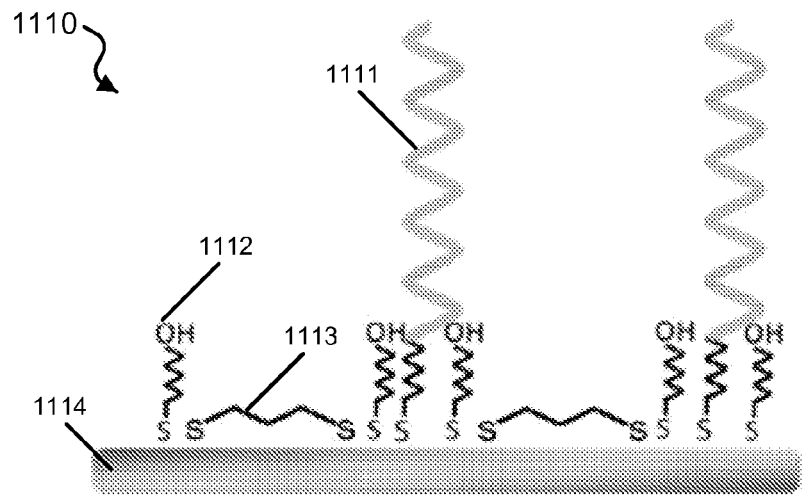
FIGS. 11A-11C show schematic illustrations of exemplary linear dithiol-based ternary monolayer interfaces.
Figure 11B:
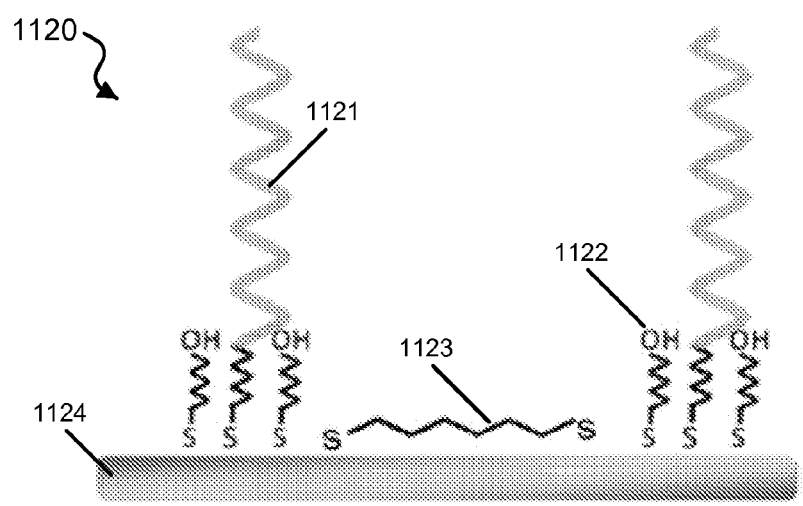
Figure 11C:
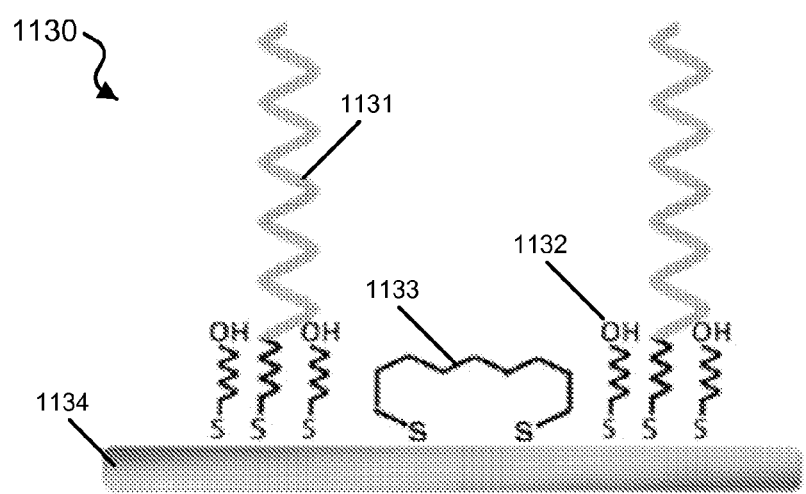

FIGS. 11A-11C show schematic illustrations of an exemplary linear dithiol-based ternary SAM interfaces, which can be implemented in a bioaffinity sensor of the disclosed technology, e.g., a ternary SAM-based electrochemical DNA hybridization biosensor. FIG. 11A shows a ternary SAM interface 1110 that includes three self-assembled monolayers that self-assemble on a gold surface 1114. For example, the three self-assembled monolayers can include a thiolated capture probe (SHCP) 1111, a short chain thiol 1112, and a linear dithiol 1113. As shown in FIG. 11A, the exemplary SHCP 1111 can include a thiol-derivatized single-stranded oligonucleotide probe. The SHCP 1111 can include other thiolated nucleic acid capture probes, e.g., such as aptamers, PNAs, and hairpin probes. The SHCP 1111 can include other thiolated compounds (e.g., mercaptocarboxylic acid compounds) having a terminal functional group that can attach a biomolecule (e.g., a nucleic acid-, lipid-, carbohydrate-, or protein-based biomolecule) to form the capture probe. The exemplary short chain thiol 1112 can include 6-mercapto-1-hexanol (MCH). For example, MCH can self-assemble on a gold surface at a thiol region of MCH. The linear dithiol 1113 can include 1,3-propanedithiol (PDT). PDT can chemisorb onto the gold surface 1114 via two Au—S bonds. For example, when PDT self-assembles on the gold surface 1114, an alkane chain can be exposed at the outer surface of the gold surface 1114. Ternary SAM interface 1110 that can be prepared by a one-step co-immobilization of SHCP and PDT and subsequent assembly of MCH, e.g., SHCP/PDT+MCH.

FIG. 11B shows a ternary SAM interface 1120 that includes three self-assembled monolayers that self-assemble on a gold surface 1124. For example, the three self-assembled monolayers can include a SHCP 1121, a short chain thiol 1122, and a linear dithiol 1123. As shown in FIG. 11B, the exemplary SHCP 1121 can include a thiol-derivatized single-stranded oligonucleotide probe. The SHCP 1121 can include other thiolated nucleic acid capture probes, e.g., such as aptamers, PNAs, and hairpin probes. The SHCP 1121 can include other thiolated compounds (e.g., mercaptocarboxylic acid compounds) having a terminal functional group that can attach a biomolecule (e.g., a nucleic acid-, lipid-, carbohydrate-, or protein-based biomolecule) to form the capture probe. The exemplary short chain thiol 1122 can include 6-mercapto-1-hexanol (MCH). For example, MCH can self-assemble on a gold surface at a thiol region of MCH. The linear dithiol 1123 can include 1,6-hexanedithiol (HDT). HDT can chemisorb onto the gold surface 1124 via two Au—S bonds. For example, when HDT self-assembles on the gold surface 1124, an alkane chain can be exposed at the outer surface of the gold surface 1124. Ternary SAM interface 1120 that can be prepared by a one-step co-immobilization of SHCP and HDT and subsequent assembly of MCH, e.g., SHCP/HDT+MCH.

FIG. 11C shows a ternary SAM interface 1130 that includes three self-assembled monolayers that self-assemble on a gold surface 1134. For example, the three self-assembled monolayers can include a SHCP 1131, a short chain thiol 1132, and a linear dithiol 1133. As shown in FIG. 11C, the exemplary SHCP 1131 can include a thiol-derivatized single-stranded oligonucleotide probe. The SHCP 1131 can include other thiolated nucleic acid capture probes, e.g., such as aptamers, PNAs, and hairpin probes. The SHCP 1131 can include other thiolated compounds (e.g., mercapto-carboxylic acid compounds) having a terminal functional group that can attach a biomolecule (e.g., a nucleic acid-, lipid-, carbohydrate-, or protein-based biomolecule) to form the capture probe. The exemplary short chain thiol 1132 can include 6-mercapto-1-hexanol (MCH). For example, MCH can self-assemble on a gold surface at a thiol region of MCH. The linear dithiol 1133 can include 1,9-nonanedithiol (NDT). NDT can chemisorb onto the gold surface 1134 via two Au—S bonds. For example, when NDT self-assembles on the gold surface 1134, an alkane chain can be exposed at the outer surface of the gold surface 1134. Ternary SAM interface 1130 that can be prepared by a one-step co-immobilization of SHCP and NDT and subsequent assembly of MCH, e.g., SHCP/NDT+MCH.

Figure 12A:
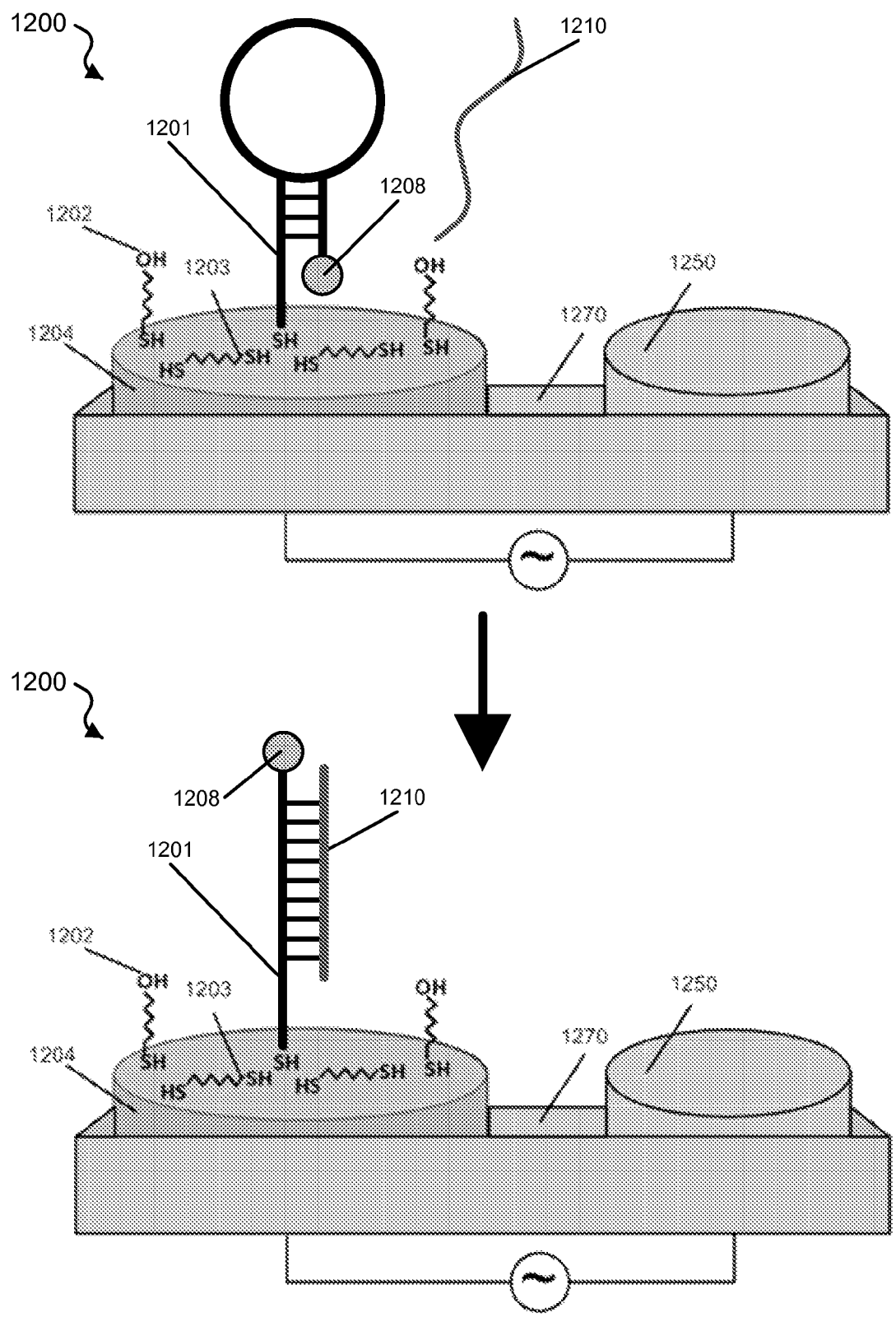
FIGS. 12A and 12B show exemplary schematic illustrations of a biosensor to detect a target substance using a dithiol-based ternary monolayer interface.

FIG. 12A shows an exemplary schematic illustration of an electrochemical detection scheme using a linear dithiol-based ternary monolayer interface biosensor 1200 of the disclosed technology. For example, the biosensor 1200 can include sensor chip substrate 1270 that can include at least one detecting electrode 1204 having a thiol reactive surface, e.g., a gold surface. The sensor chip substrate 1270 can include a reference electrode 1250. In some examples, an auxiliary electrode is also included in the biosensor 1200. The biosensor 1200 can include a dithiol-based ternary monolayer interface that can be prepared, for example, by a one-step co-immobilization of a thiolated molecular capture probe 1201 (e.g., an EC SHCP) and an alkanedithiol 1203 (e.g., a linear dithiol HDT, PDT, or NDT or a cyclic dithiol DTT), followed by the assembly of a linear single-thiol alkane chain 1202 (e.g., MCH) on the thiol reactive surface 1204. The immobilized capture probe 1201 can detect and bind a target 1210 (e.g., a target DNA oligonucleotide) to the biosensor 1200. In some examples, the biosensor 1200 is an electrochemical sensor having the SHCP 1201, linear alkanedithiol 1203, and alkanethiol chain 1202 assembled on a thiol reactive surface of detecting electrode 1204 without additional molecular components conjugated to the probe. For example, the SHCP 1201 can be configured as a dual labeled hairpin probe (e.g., with one end having a thiolated group and the end having a redox or enzymatic label, e.g., label 1208) that changes the conformation after hybridization with a target. For example, the label 1208 can be attached to or incorporated as a region of a hairpin capture probe actuating a signal upon coupling of the exemplary target 1210. For example, the change in conformation can result in a different electrochemical response. For example, the exemplary electrochemical biosensor 1200 can be electronically addressed (e.g., using electrochemical impedance spectroscopy) to transduce a detected signal from a coupling event at the hybridization region of the probe.

Figure 12C:
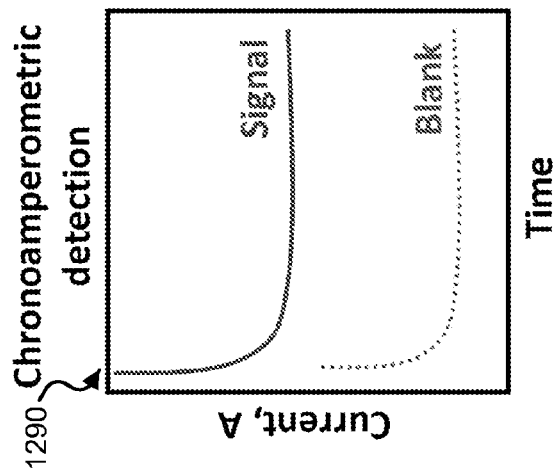
FIG. 12C shows data plot of chronoamperometric detection output in the presence and absence of target DNA.
Figure 12B:
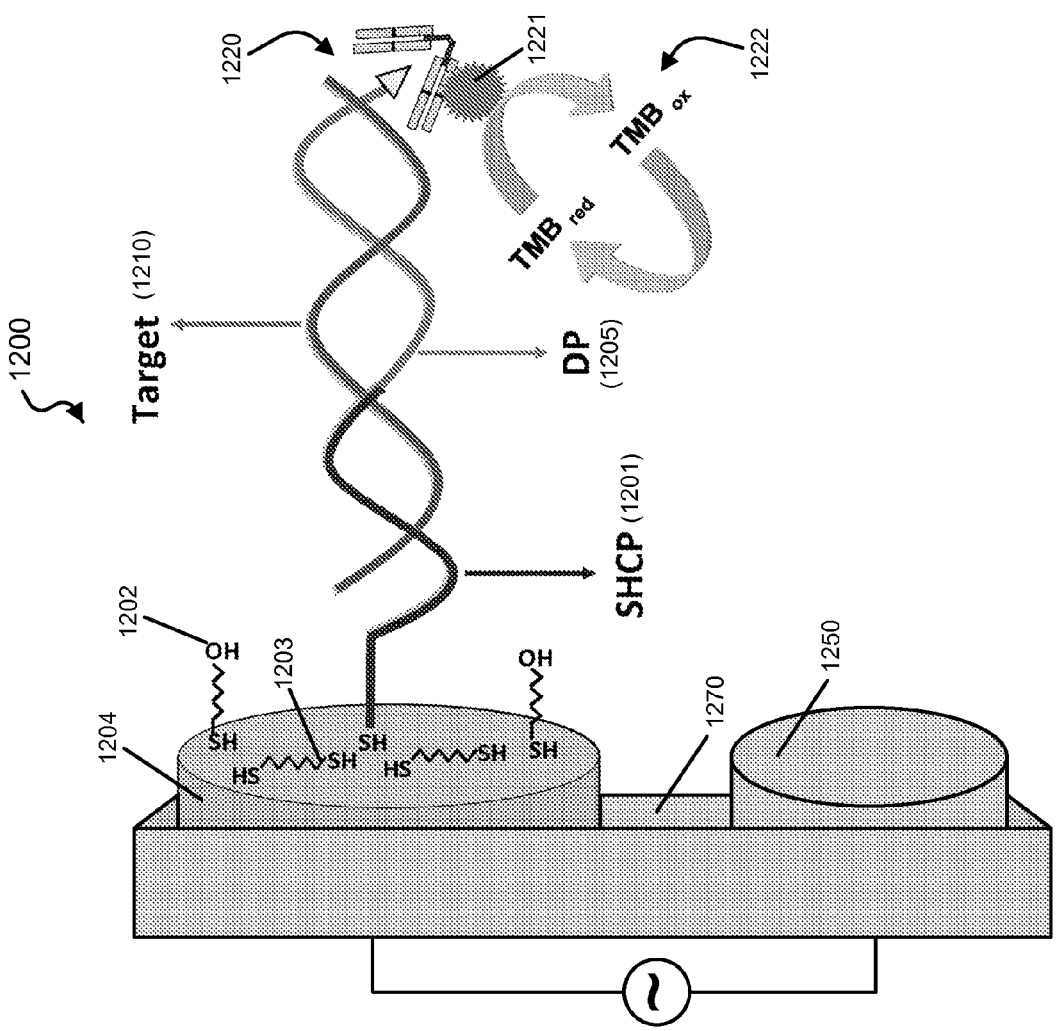

FIG. 12B shows another exemplary schematic illustration of an electrochemical detection scheme using the linear dithiol-based ternary SAM interface biosensor 1200. The biosensor 1200 is an electrochemical sensor having the SHCP 1201 (e.g., as a single-stranded oligonucleotide), the linear alkanedithiol 1203, and the alkanethiol chain 1202 assembled on the detecting electrode 1204 that can bind the target 1210. In some examples, a reporter molecule 1220 can be attached to or incorporated as a region of a detector probe (DP) 1205 actuating a signal upon coupling of the exemplary target. For example, the hybridization regions of the target 1210 with the SHCP 1201 and the DP 1205 can be contiguous. For example, binding of the target 1210 to the corresponding hybridization regions of the capture probe 1201 and the detector probe 1205 can create a three-component "sandwich" complex on the sensor surface. For example, the biosensor 1200 can include a fluorophore-modified detector probe, e.g., where the reporter molecule 1220 is a fluorophore is located at the external end of DP 1205. In some examples, the fluorophore-modified detector probe can be a fluorescein-modified detector probe that can enable binding of an anti-reporter-conjugated molecule 1221, e.g., an antifluorescein-conjugated molecule such as horseradish peroxidase (anti-HRP) reporter enzyme, to the target probe "sandwich" complex. For example, biosensor 1200 can also include a redox enzyme co-substrate 1222, e.g., 3,3',5,5' tetramethylbenzidine (TMB). The exemplary biosensor 1200 can include an application of a fixed potential between an exemplary working sensor electrode (e.g., the electrode 1204) and the reference electrode 1250, thereby creating a horseradish peroxidase-mediated redox cycle that can detected by the electrochemical biosensor 1200, e.g., as a current signal. For example, the coupling event can be transduced by use of detector probes (e.g., DP 1205) labeled with markers, e.g., redox and/or enzymatic as shown in FIG. 12B, or different markers than reporter molecule 1220 and anti-reporter-conjugated molecule 1221. In other examples, biosensor devices employing the disclosed linear dithiol-based ternary SAM interface (e.g., SHCP/HDT+MCH) can be implemented in a non-electrochemical sensor system (e.g., SPR and microbalance) to detect target biomolecules, e.g., providing highly sensitive target signal detection and low background signal perturbations.

FIG. 12C shows a data plot 1290 of the current output in an exemplary implementation of biosensor 1200 involving the presence and absence of target DNA 1210. For example, in this exemplary design, the magnitude of the electroreduction current can reflect the concentration of the target-probe hybrids on the sensor surface. The exemplary data in plot 1290 was obtained by an exemplary sensor like that of biosensor 1200 that used low sample volumes, e.g., 40 µL of sample for the analysis. The exemplary biosensor 1200 can include other linear dithiols (e.g., PDT or NDT) and can produce similar results in connection to different enzyme or non-enzyme tags.

Figure 13:
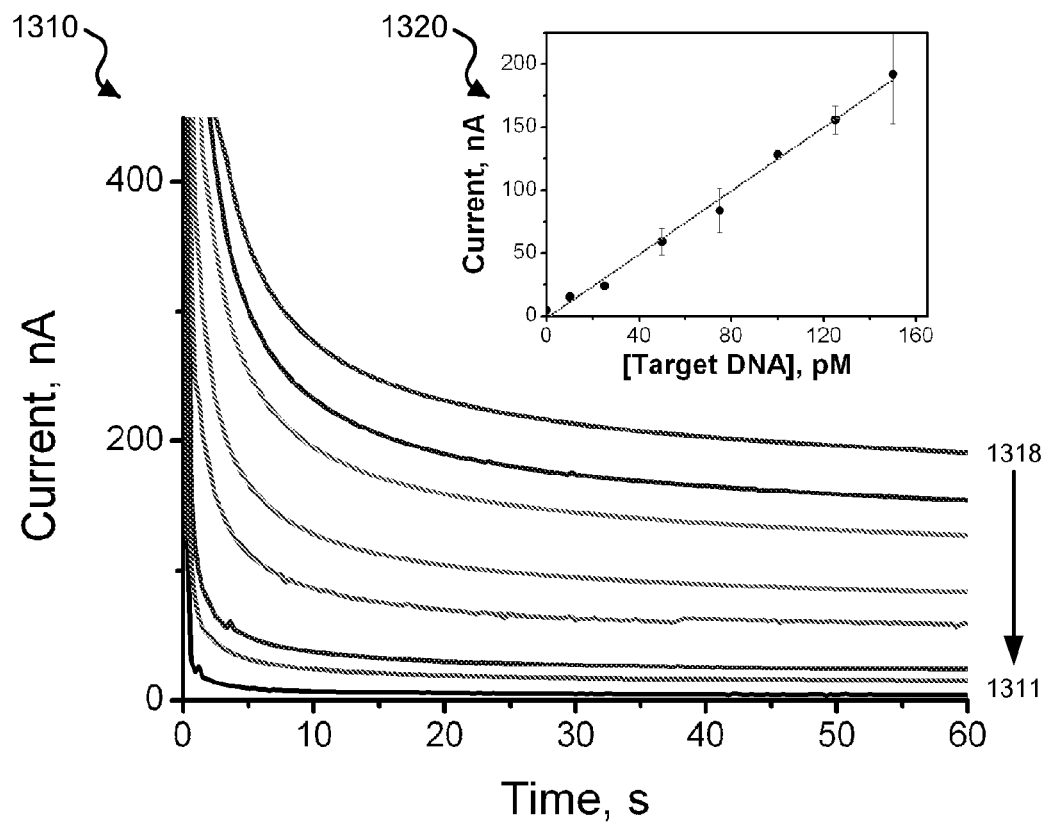
FIG. 13 shows a data plot exhibiting chronoamperometric responses of an exemplary ternary SAM interface for different concentrations of E. coli target DNA in human serum.

FIG. 13 shows an exemplary data plot 1310 of chronoamperometric response data for different target EC DNA concentrations obtained from biosensor 1200 at −0.2 V to detect target EC DNA hybridization in untreated and undiluted human serum. The exemplary biosensor chips were modified with a linear dithiol based ternary monolayer, e.g., EC SHCP/HDT+MCH. For example, FIG. 13 shows a data plot 1310 exhibiting exemplary chronoamperometric responses of data 1311, 1312, 1313, 1314, 1315, 1316, 1317, and 1318 for different concentrations of the target EC DNA over a time course. Data line 1311 corresponds to 0 M of the target EC DNA. Data line 1312 corresponds to 10 pM of the target EC DNA. Data line 1313 corresponds to 25 pM of the target EC DNA. Data line 1314 corresponds to 50 pM of the target EC DNA. Data line 1315 corresponds to 75 pM of the target EC DNA. Data line 1316 corresponds to 100 pM of the target EC DNA. Data line 1317 corresponds to 125 pM of the target EC DNA. Data line 1318 corresponds to 150 pM of the target EC DNA. The inset of FIG. 13 shows calibration data plot 1320 obtained in the same range of concentrations. The exemplary calibration plot 1320 indicates a linear dependence between the output signal and the target EC DNA concentration over the picomolar range. For example, the lowest detectable concentration in this exemplary implementation, 7 pM, corresponds to 28 attomoles in the 4 µL sample analyzed.

The techniques, systems, devices and materials described in this aspect of the disclosed technology can provide control of the surface chemistry and coverage achieved with the disclosed platform to ensure high reactivity, orientation/accessibility, and stability of exemplary surface-bound nucleic acid probes. The techniques, systems, devices and materials described in this aspect of the disclosed technology can be used to avoid non-specific adsorption and related background contributions, e.g., displaying reproducible probe-modified surfaces with high hybridization efficiency even in the presence of pure complex biological samples. Thus, the disclosed linear dithiol-based ternary SAM interfaces can offer the detection capabilities, e.g., in short time durations (e.g., 30 min) and with high sensitivity (e.g., low picomolar levels of target EC DNA, e.g., down to 7 pM or 28 amol and 17 pM or 68 amol in serum and urine, respectively) directly in undiluted and untreated biological samples. The techniques, systems, devices and materials of the disclosed technology can be implemented in the absence of any signal or target amplification protocol and without pretreatment or dilution of a clinical sample under study.

In another aspect of the disclosed technology, a thiolated capture probe can be co-immobilized with a linear dithiol on a thiol reactive surface, also with subsequent immobilization of a short chain thiol, to form a ternary SAM interface. For example, the disclosed technology can include the exemplary ternary SAM interfaces 1110, 1120, and 1130 shown in FIGS. 11A-11C. Various exemplary implementations of electrochemical genosensors are described for direct detection and measurement of nucleic acid targets, e.g., specific DNA sequences in undiluted and untreated biological samples. The disclosed genosensors can incorporate ternary SAM interfaces. For example, exemplary ternary SAM interfaces can include linear dithiol based ternary monolayers, e.g., HDT co-immobilized with a thiolated capture probe (e.g., EC SHCP) on gold surfaces and subsequent immobilization of a short chain thiol (e.g., 6-mercapto-1-hexanol (MCH)) as diluent.

In some examples, the disclosed technology can include bioaffinity assays that are implemented using electrochemical genosensors incorporating the disclosed ternary SAM interfaces (e.g., linear dithiol SHCP/HDT+MCH) to detect and measure nucleic acid targets. In other examples, the disclosed technology can include electrochemical immunoassay-, protein-, and cell-based sensors for different target biomolecules (e.g., lipids, carbohydrates, proteins, glycogens, organelles, cells, viruses, and other biological materials and living organisms). Also, for example, the disclosed technology can include non-electrochemical bioaffinity detection schemes incorporating the described ternary SAM interfaces, e.g., surface plasmon resonance (SPR) and microbalance characterization techniques.

Exemplary biosensor employing the ternary SAM interfaces SHCP/DTT+MCH, SHCP/PDT+MCH, SHCP/HDT+MCH, SHCP/NDT+MCH, and SHCP/1-hexanethiol (HMT)+MCH are shown in several exemplary implementations to demonstrate its hybridization efficiency and antifouling capability, e.g., including pM target concentrations in undiluted clinical samples. Relations between the structure of these linear dithiols and the analytical performance of the ternary monolayers were evaluated and are described. For example, in undiluted human serum the exemplary HDT-based ternary SAM interface offered 80-fold and 8-fold improvements in the S/N over the binary SAM interfaces and exemplary DTT-based ternary SAM interface, respectively. Exemplary characterizations that include impedance spectroscopy and cyclic voltammetric techniques were performed to characterize surface coverage of these engineered biosensor interfaces. Exemplary materials, apparatuses, and techniques to produce and implement bioaffinity sensors including ternary SAM interfaces of this aspect of the disclosed technology are described herein.

Materials used in the exemplary implementations included 6-mercapto-1-hexanol (MCH, 97%), 1,3-propanedithiol (PDT, 99%), 1,6-hexanedithiol (HDT, 96%), 1-hexanethiol (HMT, 95%), 1,9-nonanedithiol (NDT, 95%), DL-dithiothreitol (DTT), Trizma® hydrochloride (Tris-HCl), ethylenediaminetetraacetic acid (EDTA), human serum (e.g., from human male AB plasma) and bovine serum albumin (BSA), which were obtained from Sigma-Aldrich (St. Louis, Mo.) and used without further purification. The exemplary blocking agent casein was obtained from Pierce (Rockford, Ill.). The exemplary enzyme substrate 3,3',5,5'-tetramethylbenzidine (TMB, Neogen K-blue enhanced activity substrate, containing $H_2O_2$) was obtained from Neogen (Lexington, Ky.). The exemplary conjugated anti-fluorescein-horseradish peroxidase (anti-FITC-HRP, Fab fragments) was acquired from Roche Diagnostics (Mannheim, Germany). The composition of the buffers used in the different exemplary implementations was as follows. For example, the exemplary immobilization buffer (IB) contained 10 mM Tris-HCl, 1 mM EDTA, and 0.3 M NaCl (pH 8.0); the exemplary hybridization buffer (HB) was a 1.0 M phosphate solution containing 2.5% BSA (pH 7.2); and the exemplary binding buffer (BB), e.g., for the incorporation of the conjugated anti-FITC-HRP, included PBS (1×) containing 0.5% casein (pH 7.2).

Synthetic oligonucleotides designed for detecting a characteristic region of E. coli 16S rRNA used in the exemplary implementations were acquired from Integrated DNA Technologies, Inc. (CA, USA), which are listed in Table 4. It is noted, for example, that the exemplary sequence of exemplary 30-mer complementary target EC DNA is a copy of partial region of the E. coli 16S rRNA gene (e.g., position 432-461 according to the 5'→3' nucleotide sequence). For example, the probe pair (e.g., SHCP and FITC-DP) was designed to be fully complementary to both synthetic target DNA and the partial region of the E. coli 16S rRNA targets.

TABLE 4

| Oligonucleotide | SEQ ID NO | Sequence (5'→3') |
|---|---|---|
| Thiolated capture probe, | 1 | Thiol-TAT TAA CTT TAC TCC |
| Detector probe, FITC-DP | 3 | CTT CCT CCC CGC TGA-FITC |
| Complementary target | 5 | TCA GCG GGG AGG AAG GGA |

Chronoamperometric measurements performed in the exemplary implementations used, for example, disposable 16-sensor Au electrode arrays (GeneFluidics Inc. Monterey Park, Calif., USA). Each exemplary sensor included a 2.5 mm diameter central gold working electrode, surrounded by a gold counter electrode and a gold pseudo-reference electrode. For example, the sensor chip was driven by a computer-controlled PalmSens hand-held potentiostat with an eight-channel PalmSens Multiplexer (Palm Instruments BV, Houten, The Netherlands).

EIS and CV measurements performed in the exemplary implementations are described. For example, CV and EIS were performed with a CHI 660D Electrochemical Analyzer (CH Instruments, Austin, Tex., USA). These exemplary implementations were undertaken using an exemplary three-electrode setup with a 2 mm diameter gold disk (AuE) as working electrode, a Ag/AgCl reference electrode and a Pt wire as auxiliary electrode. Pretreatment was performed to clean the working electrode. Exemplary measurements were carried out in a 0.1 M KCl solution containing 5 mM of $K_3Fe(CN)_6$ and 5 mM of $K_4Fe(CN)_6$. Exemplary electrochemical impedance spectra were obtained at +0.25 V under an AC amplitude of 0.01 V and a frequency range from 0.01 to 10,000 Hz. Exemplary impedance data were analyzed by non-linear least-squares using the EQUIVCTR.PAS (EQU) program.

Preparation of the DNA recognition interfaces performed in the exemplary implementations is described. For example, co-assembled SHCP/dithiol+short chain thiol based ternary surfaces can be produced by the following steps. For example, a mixture of EC SHCP and a freshly prepared dithiol, with appropriate concentrations, was prepared in IB buffer and allowed to stand for 10 min. Aliquots of 6 µL of this mixture were cast over each exemplary Au working electrode in the 16-sensor array and incubated overnight at 4° C., e.g., in a humidified chamber. For example, after washing with water and drying with nitrogen, the mixed monolayer-modified Au sensors were subsequently treated with 6 µL of 1 mM MCH aqueous solution (in IB buffer) for 50 min to obtain the ternary SAM interfaces. The ternary SAM interface biosensors were thoroughly rinsed with water and dried under nitrogen.

Exemplary experimental implementation procedures of DNA hybridization assays in HB are described. In one example, the exemplary ternary SAM based sensor response was evaluated with a sandwich-type hybridization assay, e.g., using fluorescein as a tracer in the detection probe and anti-fluorescein-HRP as the reporter molecule. For example, TMB was the selected substrate for the electrochemical measurement of the activity of the captured HRP reporter. For example, different concentrations of the target EC DNA were mixed with FITC-DP (0.25 µM) in HB and allowed to react, e.g., for 15 min for homogeneous hybridization. For example, aliquots of 4 µL of the preformed hybrid solution were cast on each of the SAM-modified gold sensors and incubated, e.g., for 15 min. After hybridization, the exemplary array was washed and dried and each working electrode in the array was incubated with 4 µL of a 0.5 U mL$^{-1}$ anti-FITC-HRP solution in BB, e.g., for 15 min. Subsequently, the exemplary array was washed and dried, and a prefabricated plastic 16-well manifold (GeneFluidics, Monterey Park, Calif., USA) was bonded to the sensor array. For example, to perform the chronoamperometric detection, 50 µL of the TMB-H$_2$O$_2$ K-Blue reagent solution were placed sequentially on each of the sensors in the array, covering the three electrodes area. After a period of time (e.g., 30 s), the potential was stepped to −200 mV (vs. the gold pseudo-reference electrode) and the current was sampled, e.g., during 60 s.

Exemplary experimental implementation procedures of DNA hybridization assays in clinical samples are described. In one example, target EC DNA and EC FITC-DP (0.25 µM) were prepared either in undiluted commercial human serum or fresh untreated urine. Exemplary homogeneous hybridization between different target concentrations and the detection probe was carried out in the untreated samples. 4 µL of the hybrid solution were cast on each exemplary modified sensor and incubated, e.g., for 15 min. For example, capture of anti-FITC-HRP and electrochemical detection were carried out using according to the exemplary protocol described above for the determination of target EC DNA in HB. Exemplary implementations of DNA hybridization assays in clinical samples were carried out at room temperature (e.g., 22-25° C.). For example, evaluation of the non-fouling properties of the new interfaces included casting a 6 µL droplet of the untreated clinical samples over each exemplary SAM-modified working electrode, e.g., which were left overnight at 4° C. in a humidified surrounding. After washing with water and drying with nitrogen, the exemplary sensor array can be used again for other implementations, e.g., determination of target EC DNA in HB (as aforementioned).

Exemplary experimental data is described that demonstrates the disclosed linear dithiol based ternary monolayer interfaces implemented in electrochemical genosensor applications. In one example, different DNA sensing interfaces were prepared in an exemplary two-step procedure by co-assembling the EC SHCP and a linear dithiol (e.g., PDT, HDT or NDT) onto the gold electrode followed by the incorporation of the MCH diluent. The hybridization efficiency of these exemplary interfaces was characterized by chronoamperometric measurements, e.g., using the sandwich hybridization assay.

Figure 14:
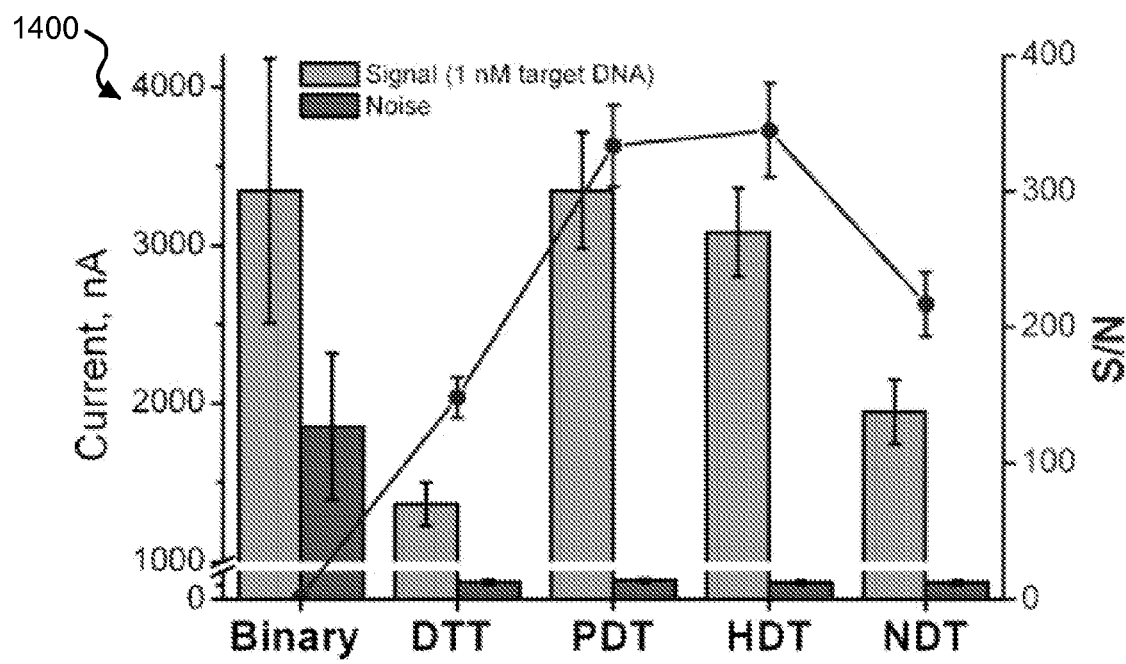
FIG. 14 shows a graph featuring exemplary biosensor characteristic data for detecting target DNA using various nucleic acid recognition interfaces.

FIG. 14 shows a graph 1400 of exemplary biosensor characteristic data for detecting target EC DNA at a 1 nM concentration in HB using the different nucleic acid recognition interfaces. For example, graph 1400 shows hybridization efficiency, background noise and S/N characteristics of the exemplary biosensors having a binary SAM interface and ternary SAM interfaces including EC SHCP/DTT+MCH, EC SHCP/PDT+MCH, EC SHCP/HDT+MCH, EC SHCP/NDT+MCH. As shown in FIG. 14, the exemplary binary layer exhibited a large background current, which can suggest high susceptibility to nonspecific adsorption. The exemplary binary layer also exhibited a low S/N ratio. Considerably higher S/N ratios were obtained for the exemplary ternary SAM interfaces. For example, for the same target EC DNA concentration (e.g., 1 nM), the EC SHCP/DTT+MCH ternary layer exhibited a strong S/N ratio, e.g., due to greatly suppressed background current. However, co-immobilization of DTT was also shown to exhibit ~2.5 fold decrease of the resulting signal as compared to binary layer (e.g., 3344.4 vs. 1364.1 nA, as shown in Table 5). For example, when PDT and HDT were used as backfillers, the current response of 1 nM target DNA exhibited substantially large values while also suppressing the noise at a level similar to the exemplary DTT ternary interface. For example, S/N values reached 333.6 and 344.9 for EC SHCP/PDT+MCH and EC SHCP/HDT+MCH ternary layers, respectively, as shown in Table 5. Exemplary sensor interfaces using a NDT ternary assembly as a backfiller was shown to attain a large S/N value (e.g., 217.1), although to a somewhat lesser degree than the exemplary PDT and HDT interfaces.

Table 5 shows exemplary data demonstrating the effect of different SAMs on DNA hybridization discrimination effects using different SAM based interfaces, e.g., for data obtained with (signal) and without (noise) 1 nM target EC DNA in HB using the described HRP/TMB system. Chemical schemes denoting A/B refers to a simultaneous co-immobilization of A and B, and A+B refers to a sequential immobilization of A and B.

TABLE 5

| | Monolayer composition | Signal, nA | Noise, nA | S/N |
|---|---|---|---|---|
| Binary | EC SHCP + MCH | 3344.4 | 1854.0 | 1.8 |
| | EC SHCP/HDT | 253.7 | 10.4 | 24.4 |
| | EC SHCP/DTT | 2904 | 52.8 | 55.0 |
| Ternary | EC SHCP/DTT + MCH | 1364.1 | 9.2 | 148.3 |
| | EC SHCP/PDT + MCH | 3346.2 | 10.0 | 333.6 |
| | EC SHCP/HDT + MCH | 3081.6 | 8.9 | 344.9 |
| | EC SHCP/NDT + MCH | 1945.6 | 9.0 | 217.1 |
| | EC SHCP/HMT + MCH | 3965.0 | 1776.3 | 2.5 |

For example, the exemplary results of PDT- and HDT-based ternary surfaces exhibiting larger signal and S/N ratio values as compared to DTT-based ternary surfaces can be attributed to the preferential lying-down orientation adopted by these exemplary linear dithiols. For example, under the exemplary experimental conditions used, nonspecific adsorption of proteins and other biomolecules was minimized and noise values were greatly suppressed (e.g., for DTT-, PDT-, HDT-, and NDT-based ternary surfaces). For example, linear dithiols PDT- and HDT-based ternary interfaces exhibited large signal values, e.g., by maintaining a favorable orientation of the capture probe (e.g., EC SHCP) and good permeability of small molecules, e.g., the TMB signaling one. For example, the large signals obtained by PDT- and HDT-based sensors may be attributed to the binding orientations of these linear dithiols to the gold electrode surface. For example, as illustratively shown in FIGS. 11A and 11B, the exemplary linear dithiols (e.g., dithiol 1113 in FIG. 11A and dithiol 1123 in FIG. 11B) are oriented flat on the gold surface (e.g., gold surface 1114 in FIG. 11A and gold surface 1124 in FIG. 11B), with the two thiol groups chemisorbed onto the gold. For example, in this way, these exemplary linear dithiol molecules can act as bridges over certain surface irregularities, e.g., leading to monolayers with high stiffness and directionality. For example, ternary monolayers using HMT exhibited a similar noise response to that of binary monolayers, e.g., a higher noise level and lower S/N ratio, as shown in Table 5. For example, as shown in Table 5, a binary monolayer of EC SHCP/HDT exhibited a low noise but also a very low signal. For example, binary EC SHCP/DTT monolayers exhibited a relatively high signal, but also high noise. This exemplary binary interface data can indicate that DTT is capable to orient the EC SHCP in a position favorable for the hybridization, but not reduce the noise.

Figure 15A:
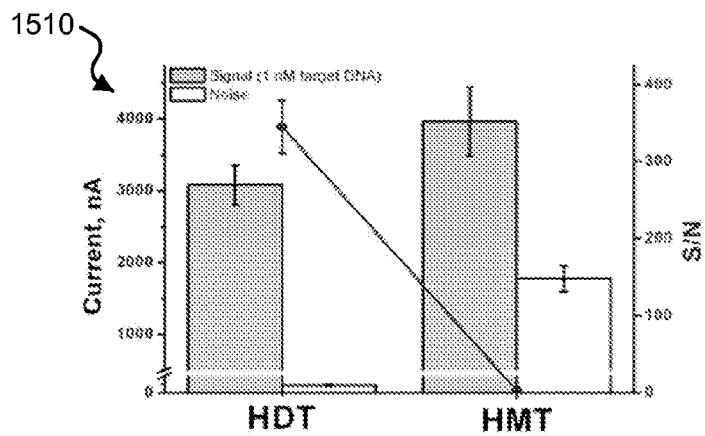
FIGS. 15A-15C show data plots comparing hybridization efficiency and electrochemical characterizations for ternary SAM interfaces prepared with HDT and HMT.
Figure 15B:
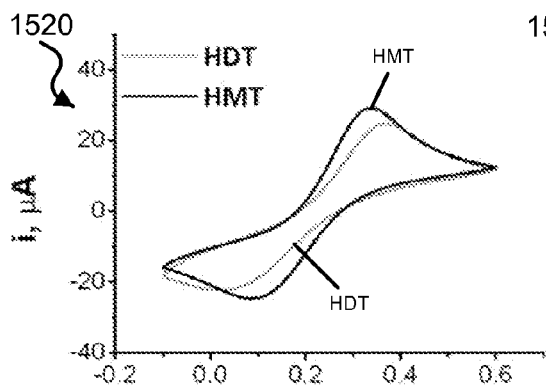
Figure 15C:
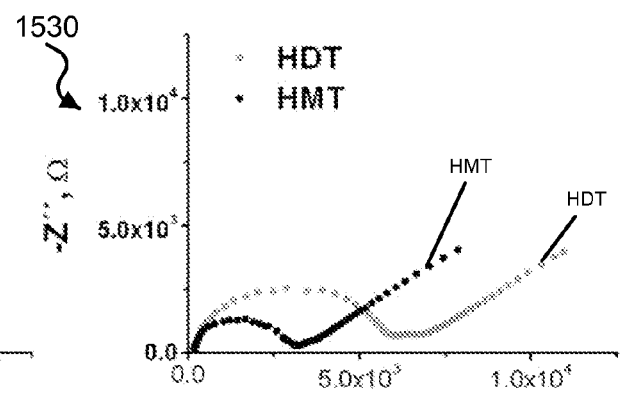

Data plots 1510, 1520, and 1530 of FIGS. 15A-15C, respectively, and Table 5 show exemplary data of hybridization efficiency (FIG. 15A) and electrochemical response characterization (FIGS. 15B and 15C) for 1 nM target EC DNA detected by exemplary ternary HDT- and HMT-based monolayer interfaces.

For example, in the ternary surfaces of the disclosed technology, the short chain thiol MCH can provide a standing-up configuration of the EC SHCP, e.g., resulting in improved orientation and hybridization efficiency of the SHCP. For example, these exemplary results can indicate that cyclic dithiols, e.g., DTT, can orient a SHCP, but can benefit from a short chain thiol like MCH to minimize background current. For example, these exemplary results can indicate that linear dithiols, e.g., HDT, can minimize background current, but can benefit from a short chain MCH to optimally orient a SHCP.

Figure 16:
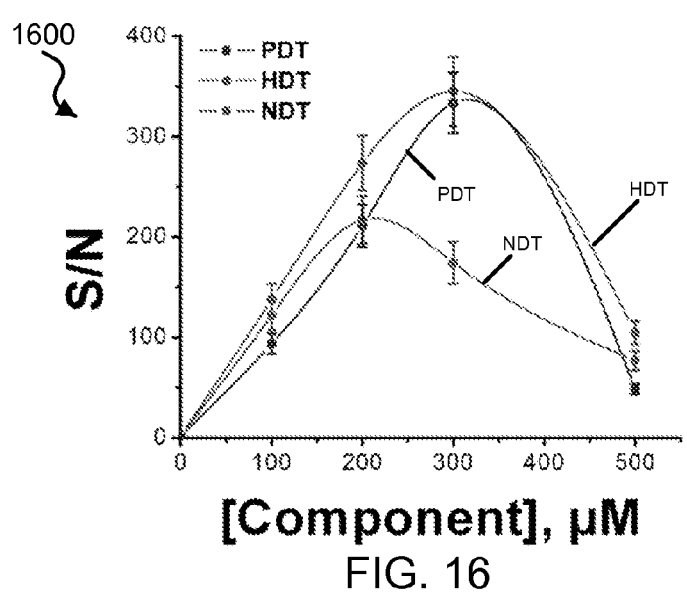
FIG. 16 shows a data plot of S/N characteristics versus concentration of the dithiol components of the ternary SAM interfaces.

Surface coverage and spacing of the SHCP molecules can be considered important factors in the efficacy of bioaffinity sensors. For example, surface coverage and spacing can be influenced by the concentration of the co-immobilized dithiol component. For example, in some instances, a dynamic competition between —SH groups of the SHCP and the dithiol backfillers can occur, e.g., until an equilibrium governed by the concentrations of the competing molecules is established. For example, under an exemplary dithiol concentration can be configured to engineer an optimum surface density, e.g., brought about by addition of the dithiols, and hybridization efficiency (e.g., related to the SHCP surface coverage) to achieve the largest possible S/N characteristics. The disclosed technology includes multiple engineered ternary monolayer interfaces that achieve the largest S/N characteristics based on concentration optimization of the monolayer components. FIG. 16 shows data plot 1600 of S/N values versus concentration of linear alkanedithiol backfiller components including PDT, HDT, and NDT. For example, at low concentrations of exemplary linear alkanedithiol backfiller components (e.g., PDT, HDT and NDT), higher noise and lower S/N values were obtained, which may be attributed to high nonspecific adsorption and incomplete surface coverage. Also, for example, at high concentrations of the exemplary linear alkanedithiol backfiller components (e.g., >300 µM), lower signal and S/N values were obtained, which may be attributed to the backfillers displacing some of the capture probe molecules, thereby decreasing the hybridization efficiency. For example, for NDT, the optimum concentration was shown to be around 200 µM, whereas for PDT and HDT the optimum concentration was shown to be around 300 µM. It is noted that the exemplary experimental implementation conditions included a 0.05 µM concentration of EC SHCP and 1 mM concentration of MCH in preparing exemplary biosensors having the ternary SAM interfaces.

Figure 17A:
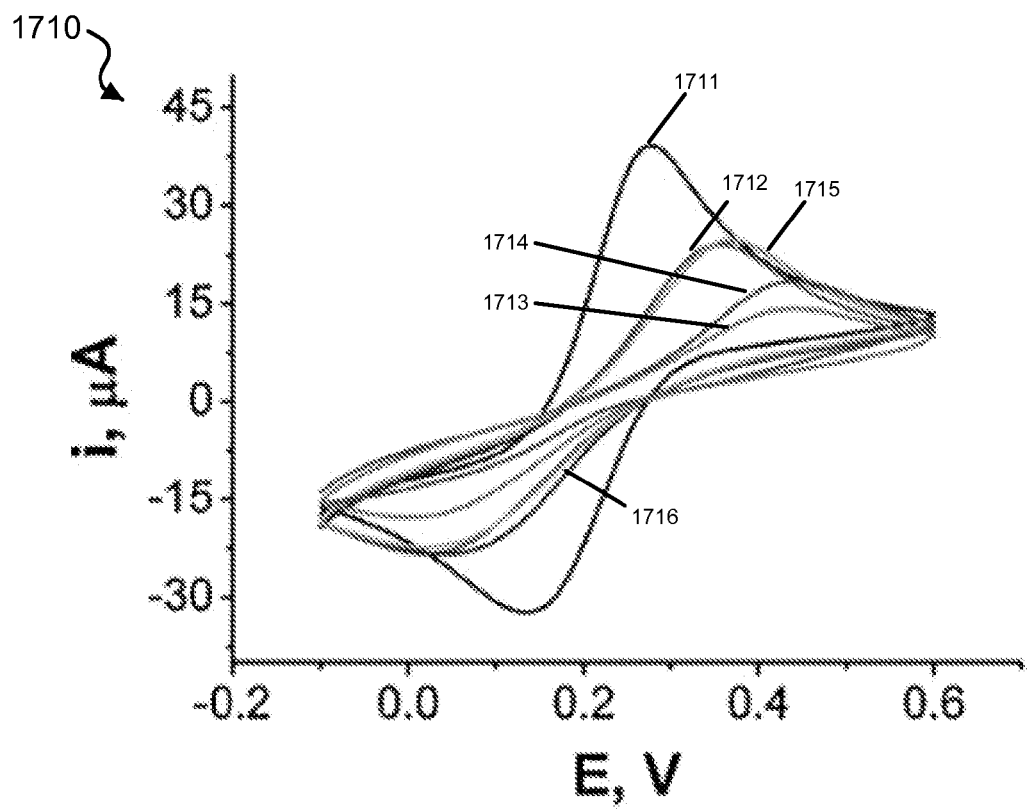
FIGS. 17A and 17B show data plots of electrochemical detection response data for binary and ternary SAM interfaces.
Figure 17B:
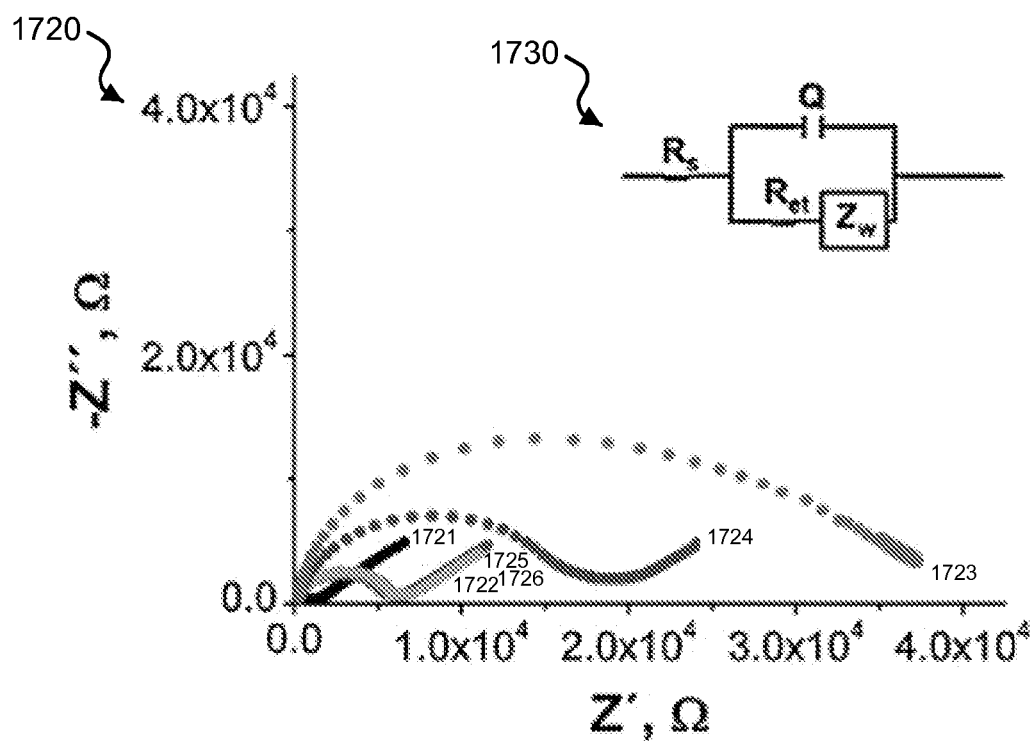

Exemplary implementations were performed to evaluate compactness and surface coverage of the disclosed linear dithiol-based ternary SAM monolayers, e.g., by CV and EIS characterizations. Exemplary electrochemical response characteristics of the dithiol-based ternary SAM monolayers and binary monolayers are shown in FIGS. 17A and 17B. For example, the blocking effects of SAMs were examined by CV using $[Fe(CN)_6]^{3-/4-}$, e.g., as a redox probe. FIG. 17A shows a data plot 1710 of cyclic voltammogram data obtained with a bare Au surface (data 1711) and with a AuE electrode modified with a binary SAM interface EC SHCP+MCH (data 1712), and ternary SAM interfaces EC SHCP/

DTT+MCH (data 1713), EC SHCP/PDT+MCH (data 1714), EC SHCP/HDT+MCH (data 1715) and EC SHCP/NDT+MCH (data 1716). FIG. 17B shows a Nyquist data plot 1720 of (Z" vs. Z') for the faradaic impedance measurements obtained with a bare Au surface (data 1721) and with a AuE electrode modified with a binary SAM interface EC SHCP+MCH (data 1722), and ternary SAM interfaces EC SHCP/DTT+MCH (data 1723), EC SHCP/PDT+MCH (data 1724), EC SHCP/HDT+MCH (data 1725) and EC SHCP/NDT+MCH (data 1726). The exemplary inset in FIG. 17B shows a Randles equivalent circuit used to fit the electrochemical impedance spectroscopy data (shown as schematic 1730). Parameters used in the exemplary implementations shown in FIGS. 17A and 17B included, for example, 5 mM [Fe(CN)$_6$]$^{3-/4-}$(1:1) in 0.1 M KCl, 0.01-10,000 Hz frequency range with a 0.01 V. signal at +0.25 V (vs. Ag/AgCl) for EIS implementations and v=100 mV s$^{-1}$ for CV implementations.

The exemplary CV data of modified surfaces (data 1712-1716) can be attributed with a decrease in the anodic and cathodic peak currents and an increase in the peak potential separation ($\Delta E_p$), e.g., compared with the voltammetric behavior of bare Au surfaces (data 1711). For example, the interfacial electron-transfer between gold and bulk solution can be blocked by the self-assembled ternary layer by different extents, e.g., which can be attributed to the structure of the backfiller, e.g., following the order: DTT>PDT>HDT≈NDT. It should be noted that ternary layers prepared with HDT and NDT show a blocking effect similar to the binary monolayer. The exemplary EIS data of bare electrodes (data 1721) can be attributed with a diffusion-limited electrode process. The exemplary EIS data of monolayer modified electrodes (data 1722-1725) showed a semicircular portion in the higher frequency range of the spectra, e.g., which can correspond to an electron transfer limited process. For example, the exemplary results of FIG. 17B can be attributed with increasing barrier properties of the ternary monolayer interface, e.g., in the order DTT>PDT>HDT≈NDT, which were in accordance with the results obtained by CV characterization in FIG. 17A.

The modified Randles equivalent circuit schematic 1730 shown in FIG. 17B was used to fit the EIS data and to determine values of the circuit components, e.g., electrolyte resistance ($R_s$), electron transfer resistance ($R_{et}$), Warburg impedance ($Z_W$) (e.g., associated to mass-transport of the redox species to the electrode surface), and double layer capacitance (Q). For example, a constant phase element was used in this exemplary implementation to calculate the double layer capacitance, e.g., to take into account the phenomenon of frequency dispersion of capacitance, which can be associated with microscopic roughness of the electrode surface. Table 6 shows exemplary electrochemical impedance data for different SAMs. For example, the exemplary data were calculated using Randles equivalent circuit (e.g., shown in schematic 1730).

TABLE 6

| Surface | Q (µF) | $Z_W$ (Ω · s$^{-1/2}$) | $R_{et}$ (Ω) | $\theta_{IS}^R$ |
|---|---|---|---|---|
| Bare | 4.96 | 4.79 × 10$^{-4}$ | 1,029.6 | — |
| EC SHCP + MCH | 0.398 | 4.43 × 10$^{-4}$ | 5,562.8 | 0.8149 |
| EC SHCP/DTT + MCH | 0.637 | 4.03 × 10$^{-4}$ | 32,595.9 | 0.9684 |
| EC SHCP/PDT + MCH | 0.396 | 3.77 × 10$^{-4}$ | 17,268.2 | 0.9404 |
| EC SHCP/HDT + MCH | 0.335 | 5.30 × 10$^{-4}$ | 5,914.6 | 0.8259 |
| EC SHCP/NDT + MCH | 0.332 | 5.40 × 10$^{-4}$ | 5,764.6 | 0.8234 |
| EC SHCP/HMT | 0.162 | 5.56 × 10$^{-4}$ | 2,847.9 | 0.6385 |
| EC SHCP/HDT | 0.234 | 6.15 × 10$^{-4}$ | 1,599.8 | 0.6436 |

The apparent fractional coverage of the electrode ($\theta_{IS}^R$) can be estimated, e.g., according to Eq. (1), from the magnitude of the charge-transfer resistance of the modified electrode ($R_{et}^{SAM}$) and the charge transfer resistance of the uncoated electrode ($R_{et}^{AuE}$), assuming that the electron transfer reaction occurs only at bare surface spots and that diffusion to these defect sites is planar. As shown in Table 6, the calculated surface coverage ($\theta_{IS}^R$) follows the order: EC SHCP/DTT+MCH>EC SHCP/PDT+MCH>EC SHCP/HDT+MCH≈EC SHCP/NDT+MCH≈EC SHCP+MCH.

Exemplary implementations of the disclosed technology for electrochemical detection of target EC DNA hybridization in complex biological samples were performed. For example, serum and urine are complex biological samples with multiple components that can be adsorbed nonspecifically onto a sensing interface, e.g., which can interfere with the binding of the target DNA (e.g., target EC DNA) and/or increase the background signal. The ternary recognition interfaces of the disclosed technology can allow the direct detection of trace target DNA in a complex biological matrix, e.g., such as pure human serum and urine.

FIGS. 18A-18D show data plots of exemplary chronoamperometric signal responses of binary and ternary SAM interfaces to target DNA in clinical samples. For example, the exemplary SAM interfaces shown in these figures includes binary SAM interface EC SHCP+MCH (black solid line), ternary SAM interface EC SHCP/DTT+MCH (red solid line) and ternary SAM interface EC SHCP/HDT+MCH (green solid line). FIGS. 18A and 18B show exemplary performance analysis of the binary and ternary SAM interfaces to 100% clinical biological samples. Data plot 1810 in FIG. 18A shows chronoamperometric signal data for binary, HDT-based ternary, and DTT-based ternary SAM interfaces obtained for 1 nM concentrations of target EC DNA (e.g., shown by solid lines) and 0 M blank target (e.g., shown by the dotted line) in 100% human serum. FIG. 18A includes an inset graph 1811 showing exemplary S/N data of the binary and ternary SAM interfaces obtained from implementation with the 1 nM target EC DNA. Data plot 1820 in FIG. 18B shows chronoamperometric signal data for binary, HDT-based ternary, and DTT-based ternary SAM interfaces obtained for 1 nM concentrations of target EC DNA (e.g., shown by solid lines) and 0 M blank target (e.g., shown by the dotted line) in 100% human urine. FIG. 18B includes an inset graph 1821 showing exemplary S/N data of the binary and ternary SAM interfaces obtained from implementation with the 1 nM target EC DNA. FIGS. 18C and 18D show exemplary non-fouling properties of the binary and ternary SAM interfaces to 100% clinical biological samples. Data plot 1830 in FIG. 18C shows chronoamperometric signal data for binary, HDT-based ternary, and DTT-based ternary SAM interfaces obtained for 1 nM concentrations of target EC DNA (e.g., shown by solid lines) and 0 M blank target (e.g., shown by the dotted line) in 100% human serum. FIG. 18C includes an inset graph 1831 showing exemplary S/N data of the binary and ternary SAM interfaces obtained from implementation with the 1 nM target EC DNA. Data plot 1840 in FIG. 18D shows chronoamperometric signal data for binary, HDT-based ternary, and DTT-based ternary SAM interfaces obtained for 1 nM concentrations of target EC DNA (e.g., shown by solid lines) and 0 M blank target (e.g., shown by the dotted line) in 100% human urine. FIG. 18D includes an inset graph 1841 showing exemplary S/N data of the binary and ternary SAM interfaces obtained from implementation with the 1 nM target EC DNA.

Detected noise level observed in these exemplary implementations using human serum and urine were shown to be lower than in HB when employing the disclosed ternary monolayers interfaces. The exemplary EC SHCP/HDT+MCH interface was shown to yield the highest S/N values for the 1 nM target EC DNA in both biological media. The exemplary binary monolayer interface implemented was shown to have a substantially large background signal such that it was not possible to measure even a 1 nM target EC DNA in these matrices.

Figure 19:
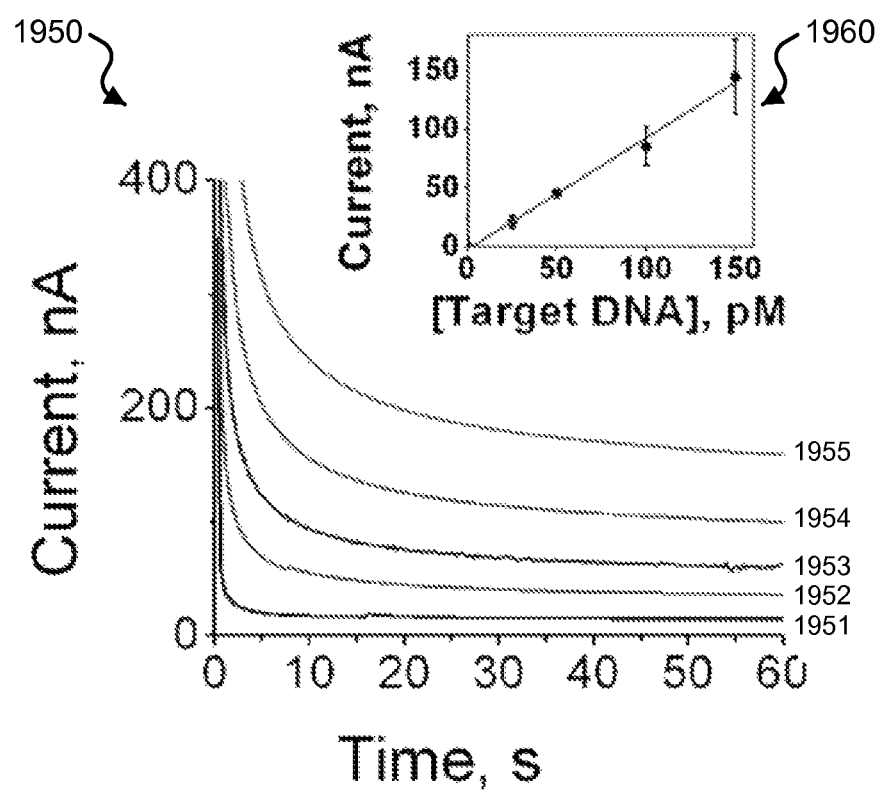
FIG. 19 shows a data plot exhibiting chronoamperometric responses of an exemplary ternary SAM interface for different concentrations of E. coli target DNA in human serum.

In other exemplary implementations to evaluate the detection limit of the disclosed bioaffinity sensors including ternary-based SAM interfaces, an exemplary ternary interface EC SHCP/HDT+MCH was exposed to various picomolar levels of a target EC DNA in 100% human serum (previously shown in FIG. 13) and urine (FIG. 19).

FIG. 19 shows a data plot 1950 of exemplary chronoamperometric response data for different target concentrations obtained from an exemplary biosensor of the disclosed technology to detect target *E. coli* DNA hybridization in untreated and undiluted human urine. For example, biosensor chips were modified with a linear dithiol based ternary monolayer, e.g., EC SHCP/HDT+MCH. For example, FIG. 19 shows a data plot 1950 exhibiting exemplary chronoamperometric responses of data 1951, 1952, 1953, 1954, and 1955 for different concentrations of the target EC DNA over a time course. Data line 1951 corresponds to 0 M of the target EC DNA. Data line 1952 corresponds to 25 pM of the target EC DNA. Data line 1953 corresponds to 50 pM of the target EC DNA. Data line 1954 corresponds to 100 pM of the target EC DNA. Data line 1955 corresponds to 150 pM of the target EC DNA. The inset of FIG. 19 shows calibration data plot 1960 obtained in the same range of concentrations. The exemplary calibration plot 1960 indicates a linear dependence between the output signal and the target EC DNA concentration over the picomolar range. For example, the lowest detectable concentration in this exemplary implementation, 17 pM, corresponds to 68 attomoles in the 4 µL sample analyzed.

Only a few embodiments have been described for this aspect of the disclosed technology. For example, ternary self-assembled monolayer interfaces that include SHCP/HDT+MCH was shown to facilitate direct measurement of target DNA in undiluted and untreated biological fluid samples, e.g., containing non-complimentary DNA. Exemplary SHCP/HDT+MCH interfaces and devices employing these interfaces were shown to exhibit excellent hybridization efficiency, e.g., which can be attributed to a favorable surface architecture. For example, HDT can be configured in a horizontal configuration, e.g., acting as a bridge over certain surface irregularities and thus providing significantly higher resistance to nonspecific adsorption of target molecules, e.g., nucleic acids and proteins. The exemplary ternary SAM interface technology can provide direct measurement of attomole and zeptomolar levels of target molecules, e.g., specific DNA for *E. coli* pathogenic bacteria. The exemplary ternary SAM interface technology can provide excellent antifouling properties and reproducible results.

In another aspect of the disclosed technology, bioaffinity sensor devices, systems, and sensing techniques can include ternary SAM interface on a screen printed surface for detection of a target molecule. For example, a thiolated capture probe can be co-immobilized with an alkanedithiol on a screen printed thiol reactive surface, also with subsequent incorporation of a short chain alkanethiol, to form a ternary SAM interface for detection of a target molecule. For example, a linear alkanedithiol, e.g., HDT, can be co-immobilized with a single-stranded nucleic acid oligonucleotide capture probe with a subsequently assembled short chain alkanethiol to produce the ternary SAM interface on a gold screen printed electrode (Au/SPE), e.g., SHCP/HDT+MCH on Au/SPE of bioaffinity sensors with excellent analytical performance.

For example, the exemplary bioaffinity sensors employing the disclosed ternary SAM interface on Au/SPEs can be configured as genosensors. The exemplary genosensors can provide direct and sensitive detection of nucleic acid hybridization events in untreated raw biological samples (e.g., serum, urine and crude bacterial lysate solutions).

The exemplary screen-printed electrodes (SPEs) described herein can be incorporated into the disclosed bioaffinity sensor devices, systems, and techniques and provide several advantages. For example, SPEs can be produced with low cost and mass quantity. SPEs can enhance the disclosed biosensor devices by facilitating minimal sample volume and reducing cross contamination. Au/SPEs can enhance the disclosed biosensor devices by enabling measurement reproducibility, e.g., without requirement for surface regeneration after each measurement. Implementations of the disclosed technology are described for mass-produced disposable bioaffinity sensors employing SHCP/dithiol+alkanethiol ternary interfaces on exemplary Au/SPEs, e.g., by modifying their surfaces with different nanomaterials (e.g., metal nanoparticles, CNTs). For example, the ternary monolayer interface can be assembled on the surface of disposable electrode strips by co-immobilizing a linear dithiol component (e.g., HDT) with the SHCP, followed by sequential confinement of a short chain thiol (e.g., MCH). For example, the disposable Au/SPEs coated with ternary SAM interfaces implemented for direct nucleic acid hybridization detection in raw biological fluids demonstrated large S/N characteristics and rapid measurements.

Exemplary implementations were performed that demonstrate the disposable bioaffinity sensors employing ternary SAM interfaces on Au/SPEs in biosensing applications. Implementation techniques and results of these exemplary implementations are described herein. Some materials used in the exemplary implementations are previously described, and other materials included KCl, NaCl, $Na_2HPO_4$, $KH_2PO_4$, $K_2HPO_4 \cdot 3H_2O$, $NaH_2PO_4$, and hydrogen tetrachloroaurate (III) hydrate ($HAuCl_4 \cdot 3H_2O$), acquired from Sigma-Aldrich (St. Louis, Mo.) and used without further purification. 2M KOH (Panreac), prepared in deionised water, was used for exemplary pretreatment of the gold disk electrode. A 0.5 M $H_2SO_4$ solution containing or not 10 mM KCl prepared in deionised water was used for exemplary pretreatment of the Au/SPEs. An $AuCl_4^-$ 1 mM solution, prepared in 0.1 M HCl, was used for the nanostructuration of the SPEs.

Exemplary implementations include chronoamperometric measurements that were carried out with a µ-AUTOLAB type III potentiostat, e.g., using the GPEs 4.9006 software (Eco Chemie, The Netherlands). A XBAS-NS-Au gold disk electrode (φ~3 mm), Au/SPEs (DropSens-220BT and DropSens-220AT), screen-printed carbon electrodes (SPCEs) (DropSens-110), and commercial gold nanoparticles (AuNPs)-modified SPCEs (DropSens-110GNP) were acquired (DropSens Inc., Oviedo-Austrias, Spain) and were used as the working electrodes. Exemplary design and inks were the same in the two different types of screen-printed gold electrodes, e.g., BT-Au/SPEs and AT-Au/SPEs; a difference between them was in the printing process. For example, AT-Au/SPEs were cured at high temperature (800-900° C.), and BT-Au/SPEs were cured a low temperature curing (90-100° C.). The average roughness (Ra) values of the AT-Au/SPEs and BT-Au/SPEs are 0.695 and 2.10 μm, respectively. The exemplary layout of the disposable planar screen-printed gold electrodes (ϕ~4 mm) includes a gold disk-shaped (12.6 mm$^2$) working electrode, a Ag pseudo-reference electrode and a gold counter electrode, all of them screen-printed on a ceramic substrate (3.4 cm×1.0 cm). An insulating layer was printed over the exemplary electrode system, e.g., leaving the electric contacts and a working area uncovered. For example, the working area can constitute the reservoir of the electrochemical cell, e.g., with a volume of 50 L. The format of the exemplary SPCEs and AuNPs-SPCEs was similar (and with a carbon counter electrode). An exemplary cable connector acted as an interface between the exemplary SPEs and the potentiostat.

Exemplary working electrodes were pretreated, for example by placing a 50 μL drop of a 0.5 M $H_2SO_4$ solution either containing (AT electrodes) or not containing (BT electrodes) 10 mM KCl onto and covering the surface of the three electrodes. Ten cyclic voltammograms from 0.00 to 1.25 V were recorded at a scan rate of 100 mVs$^{-1}$, and the electrodes were washed with deionised water and dried with nitrogen. For example, for comparison in exemplary experimental implementations, a three-electrode setup with a gold disk (AuE) as working electrode, a BAS MF-2052 Ag/AgCl/KCl (3 M) reference electrode, and a Pt wire counter electrode were employed for the comparison of the performance of the ternary monolayers assembled on Au/SPEs vs. AuE. The AuEs were also pretreated.

Exemplary AuNPs-SPCEs and AuNPs-BT-Au/SPEs were prepared by electrodeposition from a $HAuCl_4$ solution. For example, gold nanostructuring of these surfaces was achieved placing a 50 μL drop of 1 mM $AuCl_4^-$ acidic solution on the electrode surfaces and applying a constant potential of −200 mV vs. the pseudo-reference electrodes for a time course, e.g., 2 min. The modified electrodes were rinsed with water and dried under a nitrogen flow.

A mixture of the SHCP with or without the freshly prepared dithiol compound to be examined (e.g., HDT or DTT), was prepared in IB buffer solution and allowed to stand for a time course, e.g, 10 min. The exemplary mixture (10 μL) was cast on the working electrode (e.g., AT-Au/SPEs or BT-Au/SPEs, commercial GNP-SPCEs, AuNPs-SPCEs, AuNPs-BTAu/SPEs or AuE). For example, the chemisorption process was allowed to proceed overnight, e.g., in a humidified chamber. After washing with water and drying with nitrogen, for example, the modified sensors were subsequently treated with 10 μL of 1 mM MCH aqueous solution (e.g., in IB buffer) for 50 min to obtain the final SAM interfaces. For example, the sensors were thoroughly rinsed with water and dried under nitrogen. Exemplary implementations were done using 5 μM of SHCP, 600 μM of HDT and 400 μM of DTT.

Exemplary electrochemical characterizations were performed using cyclic voltammetry and electrochemical impedance spectroscopy techniques: For example, CV and EIS techniques were performed with a CHI 660D Electrochemical Analyzer (CH Instruments, Austin, Tex., USA). Exemplary measurements were carried out by placing a 50 μL drop of a 0.1 M KCl solution containing 5 mM of $K_3Fe(CN)_6$ and 5 mM of $K_4Fe(CN)_6$ onto the electrode surfaces. For example, electrochemical impedance spectra were obtained at +0.25 V under an AC amplitude of 0.01 V and a frequency range from 0.01 to 10,000 Hz. Exemplary impedance data were analyzed by non-linear least squares using the EQUIVCTR.PAS (EQU).

Exemplary implementations were performed for DNA hybridization, e.g, in HB and raw biofluid samples. For example, the electrochemical response of the prepared exemplary working electrodes was evaluated using a sandwich-type hybridization assay. In these exemplary experiments, fluorescein (FITC) and anti-FITC-HRP were used as the tracer and the reporter molecules, respectively. For example, TMB substrate was used for the electrochemical measurement of the activity of the HRP reporter. For example, target DNA at different concentrations were mixed with FITC-DP (0.25 mM) in HB and left for 15 min to obtain homogeneous hybridization. 10 μL of this solution was cast on the SAM-modified working electrode. After 15 min of incubation, the exemplary electrode was washed and dried under nitrogen. An exemplary 10 μL of a 0.5 U mL$^{-1}$ anti-FITC-HRP solution (prepared in BB) was applied to the working electrode and incubated, e.g., for an additional 15 min. The prepared electrode was washed and dried under nitrogen. For example, for electrochemical detection, a 50 μL of the TMB-$H_2O_2$ K-Blue reagent solution was placed on the modified Au/SPEs, covering the three electrodes area or by immersion of the AuE in a glass electrochemical cell containing 1.5 mL of the enzymatic substrate. Chrono-amperometric measurements were performed, e.g., after 30 s and at −200 mV vs. Ag pseudo-reference (SPEs) or Ag/AgCl reference electrodes (AuE), and the current was sampled for 60 s. For example, a working potential of −200 mV was used in these exemplary experimental implementations.

Exemplary hybridization implementations were performed in raw clinical samples. For example, HB was substituted for a clinical sample (e.g., serum and urine). Exemplary target DNA and FITC-DP (0.25 μM) were prepared directly, e.g., either in undiluted human serum or fresh untreated urine. The homogeneous hybridization between different target concentrations and the detection probe was carried out in the untreated samples. For example, 100 μL of the hybrid solution was applied to each modified sensor and incubated, e.g., for 15 min. The capture of anti-FITC-HRP and electrochemical detection were carried out using the protocol described above for the determination of target DNA in HB. For example, exemplary procedures were carried out at ambient temperature (22-25° C.).

For example, non-fouling properties of the modified surfaces were also characterized. For example, exemplary SHCP/HDT+MCH- and SHCP/MCH-modified BT-Au/SPEs received a 10 μL droplet of the untreated biological samples, e.g., applied to a SAM-modified gold working electrode and left overnight, e.g., at 4° C. in a humidified chamber. The exemplary electrode was washed with deionised water and dried with nitrogen and the protocol described above was used for the determination of target DNA in HB. For comparison purposes, a control experiment was also performed by applying 10 μL of HB on SAM-modified gold working electrode and left overnight at 4° C. in a humidified chamber.

Exemplary implementations for hybridization with bacterial rRNA in raw lysate solutions were performed. For example, bacteria were lysed by resuspension of the appropriate pellet containing ~10$^7$ CFU bacteria in 10 μL of 1 M NaOH and incubation, e.g., for 5 min. For example, 50 μL aliquot of FITC-DP (0.25 μM) in HB was added to this 10 μL bacterial lysate, e.g., yielding a concentration of nucleic acids corresponding to ~10$^7$ CFU per 60 μL. This solution was serially diluted in the FITC-DP (0.25 μM), e.g., to provide different concentrations of bacterial nucleic acids (including 16S rRNA). For example, aliquots (10 μL) of this raw bacterial lysate target solution were applied to each exemplary capture probe-modified sensor and incubated for 15 min, followed by the same volume of anti-FITC-HRP and the electrochemical detection steps (e.g., described earlier) for the synthetic target DNA. The exemplary procedures were carried out at room temperature.

The disclosed technology can include a "sandwich" hybridization technique of target DNA to a capture probe and a detector probe on a bioaffinity sensor employing the ternary interface. For example, a capture probe can be attached to the surface of the Au/SPEs and the detector probe can be FITC-linked to allow binding of a HRP labeled anti-FITC antibody. For example, application of an HRP substrate ($H_2O_2$) and its cofactor and of a measurement potential can allow chronoamperometric detection of probe-target-enzyme complexes on the working electrode surface. An schematic illustration of a biosensor device utilizing the described Au/SPEs with ternary SAM interfaces that implement the exemplary sandwich hybridization technique are shown in FIG. 20.

Figure 20:
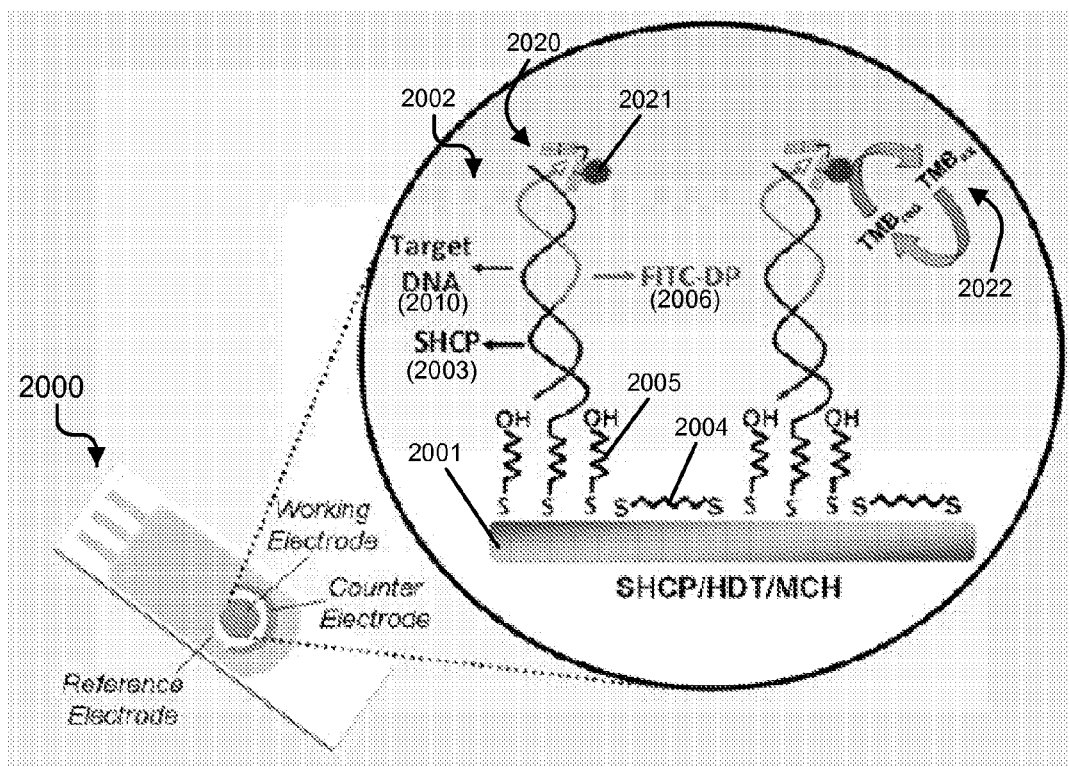
FIG. 20 shows a schematic illustration of an exemplary biosensor to detect a target substance using a sandwich hybridization detection technique.

FIG. 20 shows an exemplary schematic illustration of a biosensor device 2000 that includes a reference electrode, a counter electrode, and a working electrode. The inset of FIG. 20 shows an enlarged schematic of the working electrode. For example, the working electrode can be a screen printed electrode (e.g., Au/SPE) 2001 having a dithiol-based ternary SAM interface 2002 (e.g., SHCP/HDT+MCH), which can include exemplary components to implement the sandwich hybridization technique.

As shown in FIG. 20, the exemplary ternary SAM interface 2002 includes a thiolated molecular capture probe 2003, an alkanedithiol 2004 (e.g., a linear dithiol HDT, PDT, or NDT or a cyclic dithiol DTT), and a linear single-thiol alkane chain 2005 (e.g., MCH) on a thiol reactive surface of the Au/SPE 2001. The immobilized capture probe 2003 can detect and bind a target 2010 (e.g., a target DNA oligonucleotide) to the biosensor 2000. For example, a detector probe 2006 (e.g., FITC-DP) can be incorporated in the detection scheme to signal the presence of the target 2010, e.g., previously exemplified in FIG. 12B. For example, a reporter molecule 2020 can be attached to the detector probe 2006, e.g., actuating a signal upon coupling of the exemplary target 2010 to the detector probe 2006. For example, binding of the detector probe 2006 to the target 2010 with the capture probe 2003 can create a three-component "sandwich" complex on the sensor surface. In some examples, ternary SAM interface 2002 can include a fluorophore-modified detector probe. For example, the fluorophore-modified detector probe can be a FITC-DP that can enable binding of an anti-fluorescein-conjugated molecule 2021, e.g., horseradish peroxidase (anti-HRP) reporter enzyme, to the target probe "sandwich" complex. For example, ternary SAM interface 2002 can also include a redox enzyme co-substrate 2022, e.g., 3,3',5,5' tetramethylbenzidine (TMB). The exemplary biosensor 2000 can include an application of a fixed potential between a working electrode (e.g., Au/SPE 2001) and a reference electrode, thereby creating a horseradish peroxidase-mediated redox cycle that generates a detectable signal, e.g., as a current signal.

Exemplary experiments were implemented to obtain data, e.g., that can compare a binary interface SHCP/MCH and an exemplary ternary interface SHCP/HDT+MCH formed on different gold substrates. For example, rough BT-Au/SPEs, smooth AT-Au/SPEs and gold disk electrodes were used.

Figure 21:
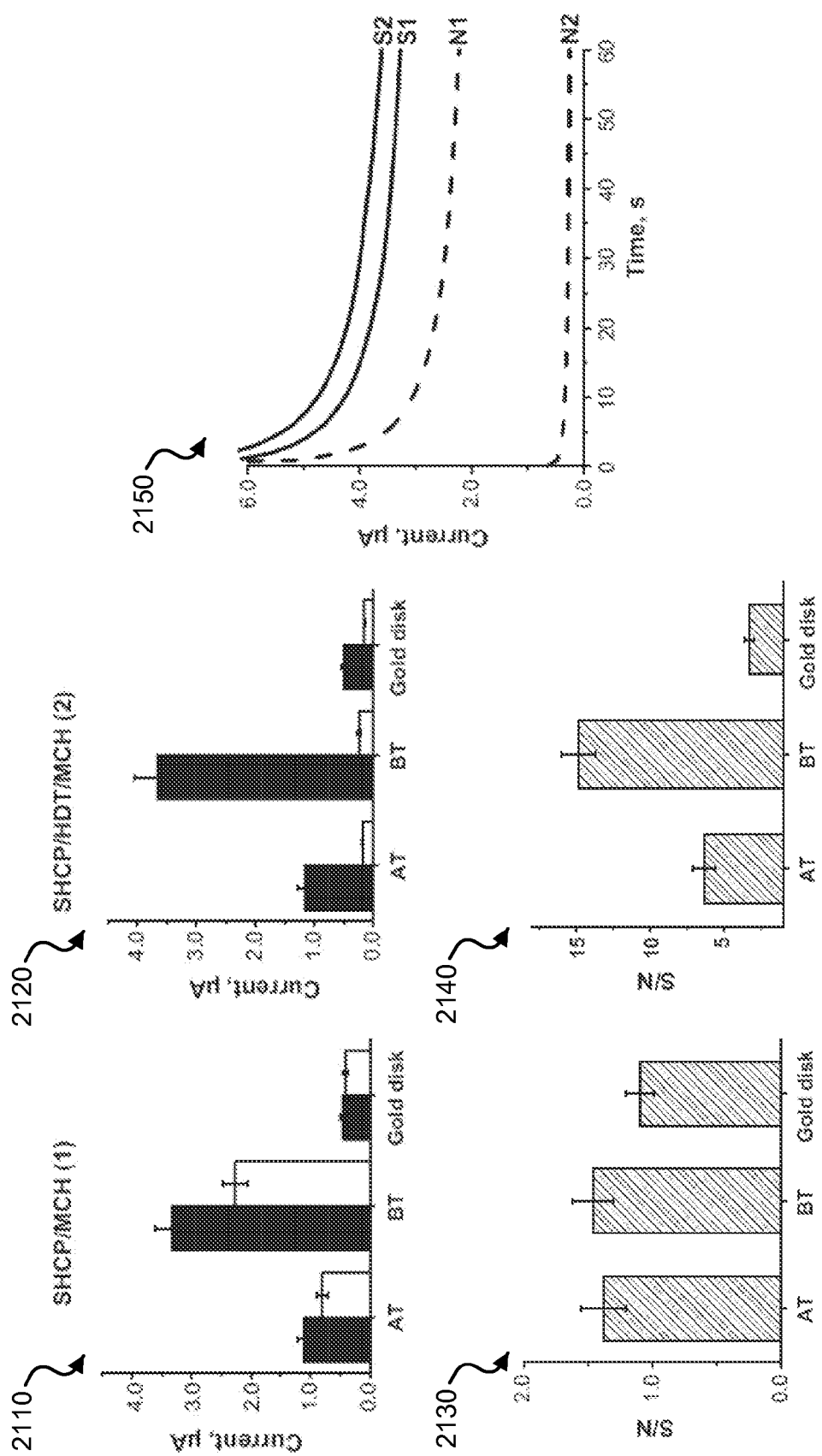
FIG. 21 shows data plots of exemplary experimental chronoamperometric response data and S/N characteristics from binary and ternary interfaces on different electrode substrates.

FIG. 21 shows data plots featuring experimental data that includes signal (S) and noise (N) values and resulting S/N ratios obtained for 1 nM (fill columns) and 0 M (empty columns) target DNA in HB obtained with different electrode substrates (e.g., BT-Au/SPEs, AT-Au/SPEs, and gold disk electrodes) having the binary SHCP/MCH SAM interface (shown in data plot 2110 and 2130) and ternary SHCP/HDT+MCH SAM interface (shown in data plot 2120 and 2140). Data plot 2150 shows chronoamperometric response data obtained for 1 nM (solid lines S1 and S2) and 0 nM of target DNA (dashed lines N1 and N2) using BT-Au/SPEs modified with the SHCP/MCH and SHCP/HDT+MCH SAMs.

Table 7 includes exemplary data showing the influence of the interface (SHCP/MCH, SHCP/HDT+MCH and SHCP/DTT+MCH) and the electrode substrate (AT-Au/SPE, BT-Au/SPE and AuE) on the DNA hybridization obtained with (signal) and without (noise) 1 nM target DNA in HB using the HRP/TMB system.

TABLE 7

| Monolayer composition | | Signal, μA | Noise, μA | S/N |
| --- | --- | --- | --- | --- |
| SHCP/MCH | AT-Au/SPE | 1.1128 | 0.8051 | 1.38 |
| | BT-Au/SPE | 3.3127 | 2.2664 | 1.46 |
| | AuE | 0.4480 | 0.4075 | 1.10 |
| SHCP/HDT + MCH | AT-Au/SPE | 1.1620 | 0.1829 | 6.35 |
| | BT-Au/SPE | 3.6668 | 0.2468 | 14.85 |
| | AuE | 0.4933 | 0.1488 | 3.31 |
| SHCP/DTT + MCH | AT-Au/SPE | 0.6309 | 0.1934 | 3.26 |
| | BT-Au/SPE | 0.7378 | 0.2021 | 3.65 |
| | AuE | 0.3756 | 0.1332 | 2.81 |

As shown in FIG. 21 and Table 7, the exemplary comparisons of the different gold surfaces show that BT-Au/SPEs provided higher signals than the AT-Au/SPEs and the gold disk electrode. The excellent sensitivity of BT-Au/SPE-based sensors (e.g., modified with a ternary SAM interface) can be attributed to the high surface area of the rough BT-Au/SPEs, e.g., which can indicate a higher number of capture-probe sites and display of SHCP that enhances the probe accessibility and lead to a faster and more efficient target hybridization.

The performance of the ternary interfaces were evaluated, e.g., a cyclic dithiol-based ternary SAM interface (SHCP/DTT+MCH) and a linear dithiol-based ternary SAM interface (SHCP/HDT+MCH). The exemplary results, shown in Table 7, can indicate that while the presence of DTT keeps the noise at the level of the HDT-based ternary layer, SHCP/DTT+MCH exhibited a reduced resulting signal as compared to SHCP/HDT+MCH.

Figure 22:
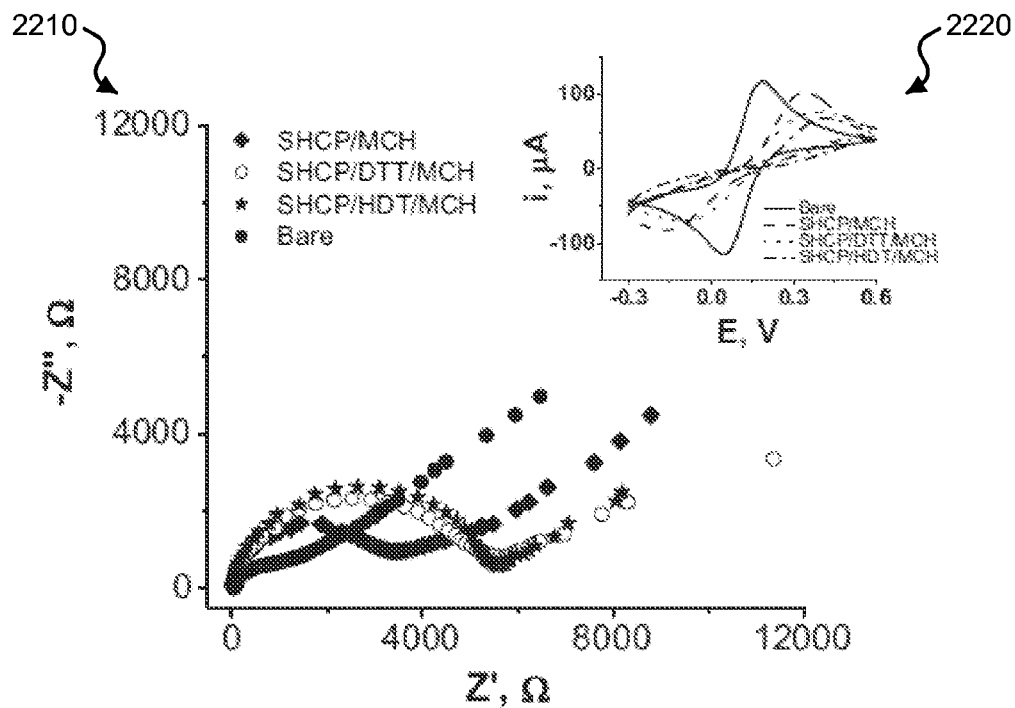
FIG. 22 shows data plots of electrochemical detection response data for binary and ternary SAM interfaces.

Exemplary BT-Au/SPEs modified with the binary and the dithiol-based ternary layers were characterized using CV and EIS. FIG. 22 shows Nyquist plot 2210 (−Z" vs. Z') for the faradaic impedance measurements and the corresponding cyclic voltammogram plot 2220 (in the inset of FIG. 22) of data obtained with a bare BT-Au/SPE surface and BT-Au/SPEs modified with SHCP/MCH, SHCP/DTT+MCH, and SHCP/HDT+MCH interfaces. Exemplary parameters in EIS implementations included 5 mM $[Fe(CN)_6]^{3-/4-}$ (1:1) in 0.1 M KCl, 0.01-10,000 Hz frequency range with a 0.01 $V_{rms}$ signal at +0.25 V (vs. Ag/AgCl), and exemplary parameters in CV implementations included $v=100$ mVs$^{-1}$.

Charge-transfer resistance values were obtained after modeling the exemplary experimental EIS data, e.g., using the Randles equivalent circuit (previously shown). Table 8 shows the exemplary SAM-modified BTAu/SPEs electrical impedance and surface coverage values. These exemplary results may suggest that the presence of the dithiol (e.g., DTT or HDT) ternary SAM component can lead to the assembly of more dense monolayers with fewer pinholes. This can be implemented on modified printed surfaces, which can further include lower background currents and attractive anti-fouling properties. Lower coverage values are calculated for the BT-Au/SPEs, as compared with the exemplary gold disk electrodes, which can demonstrate the influence of the surface roughness upon the fractional surface coverage of the monolayers.

TABLE 8

| Surface | $i_{ap}$ (µF) | $\theta_{CV}^{i}$ | Q (µF) | $R_{et}$ (Ω) | $\theta_{IS}^{R}$ |
|---|---|---|---|---|---|
| AuE | | | | | |
| Bare | 39.83 | | 4.96 | 1029.6 | |
| SHCP/MCH | 21.71 | 0.4549 | 0.398 | 5562.8 | 0.8149 |
| SHCP/DTT/MCH | 8.757 | 0.7801 | 0.637 | 32,595.9 | 0.9684 |
| SHCP/HDT/MCH | 21.12 | 0.4697 | 0.335 | 5914.6 | 0.8259 |
| BT-Au/SPEs | | | | | |
| Bare | 120.3 | | 1.95 | 1153.8 | |
| SHCP/MCH | 59.13 | 0.5085 | 0.375 | 3500.2 | 0.6704 |
| SHCP/DTT/MCH | 48.68 | 0.5953 | 0.664 | 5103.7 | 0.7739 |
| SHCP/HDT/MCH | 39.82 | 0.6690 | 0.382 | 5019.3 | 0.7701 |

Exemplary performance analysis of the SHCP/HDT+MCH layer on BT-Au/SPEs was also evaluated for different AuNPs-modified SPEs, e.g., commercially available AuNPs-modified SPCEs (GNP-SPCEs), SPCEs modified with AuNPs (AuNPs-SPCEs), and BT-Au/SPEs modified with AuNPs (AuNPs-BT-Au/SPE). For example, exemplary implementations were performed using 1 nM target DNA in HB for these exemplary SPEs. Table 9 includes exemplary data showing the influence of modification with AuNPs for the electrode substrates (e.g., GNP-SPCE, AuNPs-SPCE, AuNPs-BT-Au/SPE, and BT-Au/SPE) on the DNA hybridization obtained with (signal) and without (noise) 1 nM target DNA in HB using the exemplary HRP/TMB system.

TABLE 9

| | | Signal, µA | Noise, µA | S/N |
|---|---|---|---|---|
| SHCP/HDT + MCH | GNP-SPCE | 1.8396 | 1.1421 | 1.61 |
| | AuNPs-SPCE | 0.5734 | 0.4698 | 1.22 |
| | AuNPs-BT-Au/SPE | 2.1132 | 0.3921 | 5.39 |

FIGS. 23A and 23B show data plots demonstrating the dependence of the S/N ratio with the concentration of the molecular capture probe and the dithiol of the ternary interface on rough gold surface printed electrodes. For example, an exemplary SHCP/HDT+MCH interface was assembled on the surface of BT-Au/SPEs, and the concentration effects of the capture probe and the dithiol components upon the S/N ratio obtained for 1 nM target DNA were analyzed. FIG. 23A shows data plot 2310 demonstrating the relationship of the S/N ratio on the concentration of the SHCP of the ternary interface (e.g., prepared with a fixed HDT concentration of 300 µM). These data illustrate that the S/N ratio increased with the SHCP concentration up to 5 µM and decreased until 10 µM of SHCP, leveling off thereafter. This profile can indicate hybridization efficiency is affected by SHCP surface coverage. FIG. 23B shows data plot 2320 demonstrating the relationship of the S/N ratio on the concentration of the HDT of the ternary interface (e.g., prepared with a fixed SHCP concentration of 5 µM, along with 1 mM MCH). The concentration of the dithiol component can affect the surface coverage and the spacing of the co-assembled SHCP molecules.

Exemplary implementations were performed for electrochemical detection of DNA hybridization in raw biological samples, e.g., serum and urine. Chronoamperometric response data of a 1 nM concentration of target DNA in 100% human serum and 100% human urine were acquired using a binary interface (e.g., SHCP/MCH) and an HDT-based ternary SAM interface, which are shown in FIG. 24 and Table 10. Table 10 includes exemplary data showing the performance of the SHCP/HDT+MCH on BT-Au/SPEs in HB and 100% human undiluted and untreated clinical samples (e.g., serum and urine).

TABLE 10

| | Media | Signal, µA | Noise, µA | S/N |
|---|---|---|---|---|
| SHCP/MCH | HB | 3.3127 | 2.2664 | 1.46 |
| | 100% serum | 1.5024 | 0.7756 | 1.94 |
| | 100% urine | 2.3124 | 0.8949 | 2.58 |
| SHCP/HDT/MCH | HB | 3.6668 | 0.2469 | 14.85 |
| | 100% serum | 1.3348 | 0.2325 | 5.74 |
| | 100% urine | 1.6037 | 0.2445 | 6.56 |

FIG. 24 shows data plots of chronoamperometric response data obtained of target DNA on ternary interface-based biosensors after hybridization in 100% of human serum or urine. For example, data plot 2401 shows the chronoamperometric response of target DNA at 0 M and 25 pM concentrations in human serum after hybridization using an exemplary SHCP/HDT+MCH ternary SAM interface-modified BT-Au/SPEs. Calibration plot 2402 shows different target DNA concentrations in the untreated and undiluted human serum obtained after hybridization (and background subtraction). For example, data plot 2403 shows the chronoamperometric response of target DNA at 0 M and 250 pM concentrations in human urine after hybridization using an exemplary SHCP/HDT+MCH ternary SAM interface-modified BT-Au/SPEs. Calibration plot 2404 shows different target DNA concentrations in the untreated and undiluted human using obtained after hybridization (and background subtraction). As shown in FIG. 24, the chronoamperometric signal increased linearly with the target DNA concentration up to 1 nM, e.g., with a detection limit of 25 pM (0.25 fmol) in human serum (data plot 2402) and 100 pM (1 fmol) in urine (data plot 2404).

Resistance to biofouling of the exemplary screen-printed electrodes modified with ternary and binary monolayers was examined by exposing them to undiluted human serum and untreated urine. For example, these complex physiological samples have components that can be nonspecifically absorbed onto the interface, thus interfering with the binding of the target DNA and/or increasing the background signal. Exemplary implementations were performed to obtain data for comparison of the signal and noise values after hybridization with 1 nM and 0 nM target DNA over BTAu/SPEs modified with SHCP/MCH and SHCP/HDT+MCH interfaces. Exemplary data is shown in FIG. 25 and Table 11.

Figure 25:
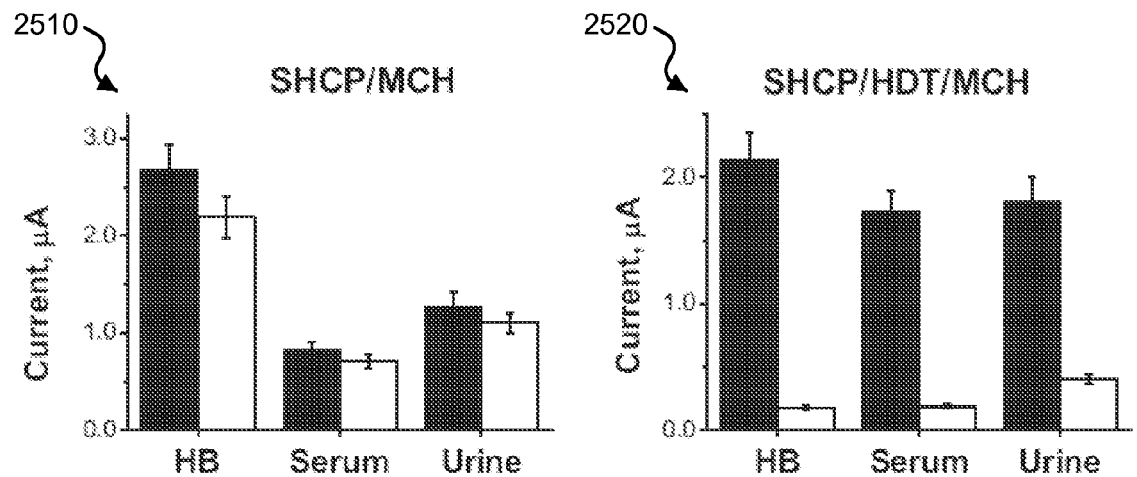
FIG. 25 shows data plots demonstrating the non-fouling properties of binary and ternary SAM interfaces on BT-Au/SPEs.

FIG. 25 shows data plots demonstrating the non-fouling properties of the SHCP/MCH interface on BT-Au/SPEs (data plot 2510) and SHCP/HDT+MCH interface on BT-Au/SPEs (data plot 2520) after 24 hr exposure in HB and biological samples of human serum and urine. Signal and noise values were obtained after hybridization with 1 nM (solid columns) and 0 M (empty columns) of target DNA in HB. Table 11 features exemplary data showing the effect of the prolonged dipping of the exemplary modified BT-Au/SPEs in undiluted clinical samples on the DNA hybridization obtained with (signal) and without (noise) 1 nM target DNA in HB using the HRP/TMB system.

TABLE 11

| | Media | Signal, μA | Noise, μA | S/N |
|---|---|---|---|---|
| SHCP/MCH | HB | 2.6730 | 2.1929 | 1.22 |
| | 100% serum | 0.8298 | 0.7080 | 1.17 |
| | 100% urine | 1.2780 | 1.1024 | 1.16 |
| SHCP/HDT + MCH | HB | 2.1364 | 0.1794 | 11.9 |
| | 100% serum | 1.7211 | 0.1874 | 9.18 |
| | 100% urine | 1.8096 | 0.4016 | 4.51 |

Figure 26A:
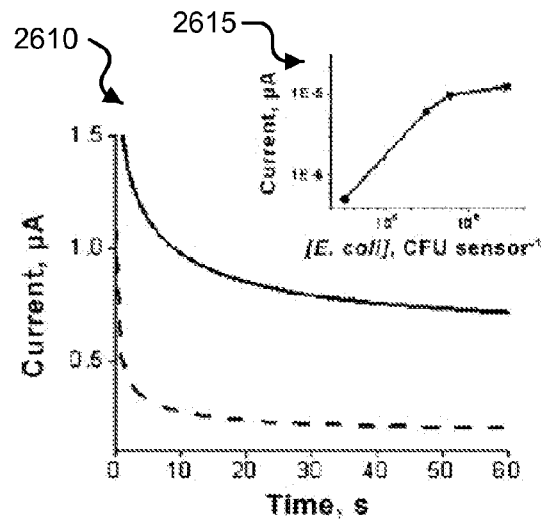
FIGS. 26A and 26B show plots and graphs of chronoamperometric signal and response data using BT-Au/SPEs modified with a ternary SAM interface to detect target DNA, 16S rRNA corresponding to E. coli, and 16S rRNA corresponding to K. pneumoniae.
Figure 26B:
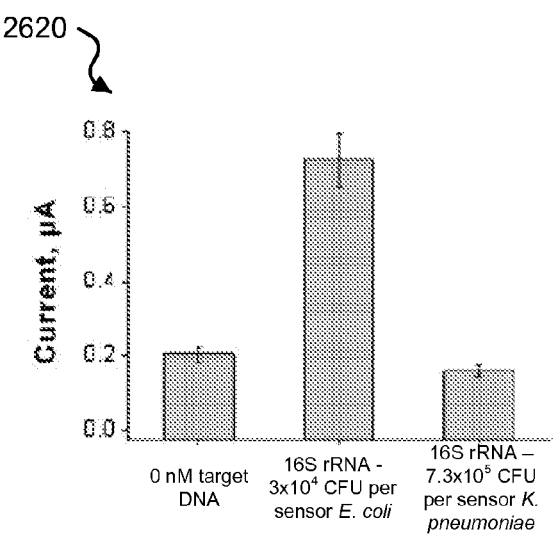

Exemplary implementations were performed for detection of E. coli 16S rRNA in raw bacterial lysate solutions, e.g., without isolation or purification steps. FIG. 26A shows a plot 2610 featuring exemplary data of chronoamperometric signals obtained using BT-Au/SPEs modified with an exemplary ternary interface SHCP/DTT+MCH for 16S rRNA of $3 \times 10^4$ CFU per sensor along with the corresponding blank (0 CFU). The exemplary inset plot 2615 in FIG. 26A shows an exemplary calibration plot for E. coli 16S rRNA corresponding to different pathogen bacterial concentrations after background subtraction. FIG. 26B shows a column bar graph 2620 of data corresponding to the chronoamperometric responses obtained using BT-Au/SPEs modified with an exemplary ternary interface SHCP/DTT+MCH with 0 nM target DNA, 16S rRNA corresponding to $3 \times 10^4$ CFU per sensor E. coli, and 16S rRNA corresponding to $7.3 \times 10^5$ CFU per sensor K. pneumoniae. As can be seen in FIGS. 26A and 26B, the disposable modified electrodes were able to distinguish the signals obtained for a bacterial lysate solution corresponding to $3 \times 10^4$ CFU per sensor from those obtained without the bacterial rRNA target. For example, data plot 2615 can indicate a nonlinear logarithmic relationship between the chronoamperometric signals and the level of E. coli between $3 \times 10^4$ and $3 \times 10^6$ CFU per sensor. For example, considering the 10 μL sample volume, an exemplary detection limit can correspond to 3000 CFU $\mu L^{-1}$. Taking into account that E. coli can contain approximately $2 \times 10^4$ copies of 16S rRNA per cell, the present detection limit of 3000 CFU $\mu L^{-1}$ can be translated to the detection of 250 pM ribosome target copies in these raw bacterial lysate solutions. Also, for example, the specificity of the exemplary disposable Au/SPE biosensor was also tested using control K. pneumoniae, another Gram-negative pathogenic member of Enterobacteriaceae, as the no-target biological control. In contrast to the chronoamperometric signal obtained for E. coli 16S rRNA, for example, the response observed in the presence of a 24-fold excess of K. pneumoniae 16S rRNA was similar to that observed for the negative control without target DNA (FIG. 26B), e.g., reflecting the high specificity and negligible nonspecific adsorption of the detection probe onto the SHCP/HDT+MCH-modified disposable electrodes.

Only a few exemplary embodiments have been described to show the disclosed technology, e.g., the application of disposable Au/SPEs modified with ternary SAM interfaces to the direct measurement of target DNA in undiluted and untreated human serum and urine samples. Despite the rough surface of BT-Au/SPEs, such ternary SAMs form highly packed monolayers with minimal defects that impart significantly higher resistance to nonspecific adsorption. The improved capabilities of the modified disposable electrodes allowed direct, sensitive and rapid (30 min) detection of picomolar levels of target nucleic acids in untreated and undiluted microliter clinical samples or bacterial lysate samples solutions. In addition, this new strip platform displayed excellent antifouling properties during prolonged exposure to raw body fluids. These results demonstrate that a rational design of the surface chemistry of screen-printed electrodes can offer significant analytical improvements and can facilitate direct assays of unprocessed body fluids. As a result, the new SAM-coated Au/SPEs offer excellent prospects for a wide range of applications in diverse environments, including single-use genetic testing in resource-poor settings.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

We claim:

1. A sensor device for detecting a target molecule, comprising:
   a detecting electrode having a surface capable of attaching a thiol;
   a sensor chip substrate on which the detecting electrode is located;
   a reference electrode located on the sensor chip substrate that is electrically coupled to the detecting electrode; and
   a ternary self-assembled monolayer formed on the surface that includes a molecular capture probe having a thiol region, a linear alkanethiol molecule having one thiol region, and a linear alkanedithiol molecule having two thiol regions, wherein each of the molecular capture probe, the linear alkanethiol molecule, and the linear alkanedithiol molecule is immobilized on the surface, and wherein the molecular capture probe includes a region for receiving a target substance having a complimentary region that couples with the region of the molecular capture probe to generate a detectable electrical signal measured between the detecting electrode and the reference electrode during a coupling event.

2. The sensor device of claim 1, wherein the molecular capture probe is at least one of a thiol-derivatized single-stranded oligonucleotide, aptamer, or peptide nucleic acid.

3. The sensor device of claim 1, wherein the linear alkanedithiol molecule is a hexanedithiol.

4. The sensor device of claim 1, wherein the linear alkanedithiol molecule is a propanedithiol.

5. The sensor device of claim 1, wherein the linear alkanethiol molecule is a 6-mercapto-1-hexanol.

6. The sensor device of claim 1, wherein the surface includes gold.

7. The sensor device of claim 1, wherein the linear alkanedithiol molecule includes a structure that self-assembles on the surface at each of the two thiol regions forming a layer that prevents perturbation of the detectable electrical signal.

8. The sensor device of claim 1, wherein the sensor device detects the target substance at concentrations in a range of zeptomoles.

* * * * *